US008168667B2

(12) United States Patent
Nique et al.

(10) Patent No.: US 8,168,667 B2
(45) Date of Patent: May 1, 2012

(54) IMIDAZOLIDINE DERIVATIVES, USES THEREFOR, PREPARATION THEREOF AND COMPOSITIONS COMPRISING SUCH

(75) Inventors: Francois Nique, Le Perreux sur Marne (FR); Catherine Jagerschmidt, Romainville (FR); Philippe Clement-Lacroix, Romainville (FR)

(73) Assignee: Galapagos NV, Mechelen (BE)

( * ) Notice: Subject to any disclaimer, the term of this patent is extended or adjusted under 35 U.S.C. 154(b) by 65 days.

(21) Appl. No.: 12/751,158

(22) Filed: Mar. 31, 2010

(65) Prior Publication Data
US 2010/0210699 A1 Aug. 19, 2010

Related U.S. Application Data

(63) Continuation-in-part of application No. 12/227,776, filed as application No. PCT/EP2007/005145 on May 31, 2007, now abandoned.

(30) Foreign Application Priority Data

May 31, 2006 (GB) ................................ 0610765.0

(51) Int. Cl.
A61K 31/4166 (2006.01)
C07D 233/02 (2006.01)
(52) U.S. Cl. ..................................... 514/389; 548/317.1
(58) Field of Classification Search ............... 548/317.1; 514/389
See application file for complete search history.

(56) References Cited

U.S. PATENT DOCUMENTS

| | | | |
|---|---|---|---|
| 4,753,957 A | 6/1988 | Chan | |
| 4,873,256 A | 10/1989 | Coussediere et al. | |
| 4,977,270 A | 12/1990 | Wee | |
| 4,992,443 A | 2/1991 | Chelen | |
| 5,750,553 A | 5/1998 | Claussner et al. | |
| 5,770,615 A | 6/1998 | Cheng et al. | |
| 6,355,664 B1 | 3/2002 | Kelly et al. | |
| 7,968,581 B2 * | 6/2011 | Nique et al. ................. | 514/391 |
| 2003/0195238 A1 | 10/2003 | Gil et al. | |
| 2004/0202825 A1 | 10/2004 | Malhotra | |
| 2010/0113547 A1 | 5/2010 | Nique | |

FOREIGN PATENT DOCUMENTS

| | | |
|---|---|---|
| DE | 2855770 A1 | 12/1978 |
| EP | 0091596 A2 | 3/1983 |
| EP | 0494819 | 7/1992 |
| EP | 0572191 A1 | 5/1993 |
| EP | 0578516 | 1/1994 |
| EP | 0704448 | 4/1996 |
| EP | 0760239 A2 | 8/1996 |
| EP | 0945441 A2 | 9/1999 |
| EP | 0966447 A1 | 12/1999 |
| JP | 01090114 | 6/1989 |
| JP | 02019363 | 1/1990 |
| JP | 06135937 A | 5/1994 |
| WO | WO 9518794 | 7/1995 |
| WO | 95/29909 | 11/1995 |
| WO | WO 9719064 | 5/1997 |
| WO | WO 9723464 | 7/1997 |
| WO | 98/39303 | 11/1998 |
| WO | 98/57633 | 12/1998 |
| WO | 01/10799 | 2/2001 |
| WO | 01/85685 | 11/2001 |
| WO | 02/14865 | 2/2002 |
| WO | WO 03096980 | 11/2003 |
| WO | 2007/047146 | 4/2007 |
| WO | 2007/137874 | 12/2007 |

OTHER PUBLICATIONS

Kaufman, Jean M. and Vermeulen, Alex, "The Decline of Androgen Levels in Elderly Men and its Clinical and Therapeutic Implications", Endocrine Reviews (2005) 26(6):833-876. Liu, Peter Y., Swerdloff, Ronald S. and Veldhuis, Johannes D., "The Rationale, Efficacy and Safety of Androgen Therapy in Older Men: Future Research and Current Practice Recommendations", The Journal of Clinical Endrocrinology & Metabolism (2004) 89(10):4789-4796.

(Continued)

Primary Examiner — Kamal Saeed
Assistant Examiner — Janet L Coppins
(74) Attorney, Agent, or Firm — Klauber & Jackson LLC

(57) ABSTRACT

Compounds of formula (I):

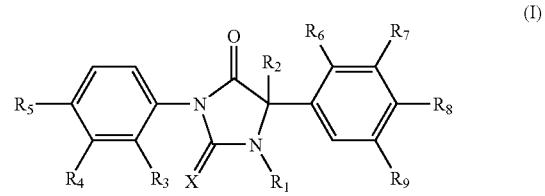

wherein
X is O or S,
$R_1$ is acyl, aldehyde, cycloalkyl, an optionally substituted alkyl, alkenyl or alkynyl,
$R_2$ is H, alkyl, hydroxyalkyl, haloalkyl, alkenyl, or alkynyl; substituted alkyl; alkylcarbonyl;
$R_3$ and $R_4$ are H, halogen, alkyl, alkenyl, alkynyl, alkoxyl, alkylthio, hydroxyalkyl, haloalkyl, haloalkenyl, or haloalkynyl;
or $R_3$ and $R_4$ form an, optionally aromatic or heterocyclic, optionally substituted ring,
$R_5$ is H, halogen, trifluoromethyl, —CN, or —NO$_2$;
not all of $R_3$, $R_4$, and $R_5$ being H,
$R_6$ and $R_9$ are H, halogen, OH; alkyl, hydroxyalkyl, alkoxyl, thioalkyl, haloalkyl, alkenyl, or alkynyl;
$R_7$ and $R_8$ are H, halogen, OH, SH; alkoxyl or alkylthio optionally substituted by OH and/or halogen; one of $R_7$ and $R_8$ not being H or halogen; or one of $R_7$ and $R_8$ is a pharmaceutically acceptable ester or thioester grouping,
or $R_6$ is $C_{1-3}$-alkyl or, together with either $R_1$ or $R_2$, represents $C_{1-3}$ alkylene or alkenylene linking group, optionally substituted by methyl, trifluoromethyl, OH, or halogen,
and pharmaceutically acceptable salts and esters thereof, are useful as selective androgen modulators.

19 Claims, No Drawings

OTHER PUBLICATIONS

Heinlein, Cynthia A. and Chang, Chawnshang, "Androgen Receptor in Prostate Cancer", Endocrine Reviews (2004) 25 (2):276-308.

Greenspan, Susan L., Coates Penelope, Sereika, Susan M., Nelson, Joel B., Trump, Donald L. and Resnick, Neil M., "Bone Loss after Initiation of Androgen Deprivation Therapy in Patients with Prostrate Cancer", The Journal of Clinical Endocrinology & Metabolism (2005) 90(12):6410-6417.

Davison, Sonia L. and Davis, Susan R., "Androgens in women", The Journal of Steroid Biochemistry & Molecular Biology, 85 (2003) 363-366.

Claessens, Frank, Alen, Philippe, Devos, Ann, Peeters, Ben, Verhoeven, Guido and Rombauts, Wilfried, "The Androgen-specific Probasin Response Element 2 Interacts Differentially with Androgen and Glucocorticoid Receptors", The Journal of Biological Chemistry, vol. 271, No. 32, Issue of Aug. 9, pp. 19013-19016 (1996).

Sims, Natalie A., Clement-Lacrois, Philippe, Minet, Dominique, Fraslon-Vanhulle, Caroline, Gaillard-Kelly, Martine, Resche-Rigon, Michele and Baron, Roland, "A functional androgen receptor is not sufficient to allow estradiol to protect bone after gonadectomy in estradiol receptor-deficient mice", The Journal of Clinical Investigation, May 2003, vol. 111, No. 9, pp. 1319-1327.

Angel, Peter, Baumann, Ina, Stein, Bernd, Delius, Hajo, Rahmsdorf, Hans Jobst and Herrlich, Peter, "12-0-Tetradecanoyl-Phorbol-13-Acetate Induction of the Human Collangenase Gene Is Mediated by an Inducible Enhancer Element Located in the 5'-Flanking Region", Molecular and Cellular Biology, Jun. 1987, pp. 2256-2266.

Washburn, W.N., et al., "BMS-201620: a selective beta 3 agonist", Biorganic & Medicinal Chemistry Letters 14 (2004) 3525-3529.

Elokdah, H., et al., Design, Synthesis, and Biological Evaluation of Thio-Containing Compounds with Serum HDL-Cholesterol-Elevating Properties, J. Med. Chem. 2004, 681.

Hourdé_2008_Acta Physiol_195_471, Androgen replacement therapy improves function in male rat muscles independently of hypertrophy and activation of the Akt/mTOR pathway.

Kun_2003_Am J Physiol Endocrinol Metab_285_E363, Glucocorticoid-induced skeletal muscle atrophy is associated with upregulation of myostatin gene expression.

Tilley_1989_PNAS_86_327, Characterization and expression of a cDNA encoding the human androgen receptor.

Molander_1995_J Org Chem_60_872, Stereochemical Investigations of Samarium(I1) Iodide-Promoted 5-Exo and 6-Ex0 Ketyl-Olefin Radical Cyclization Reactions.

* cited by examiner

SEQUENCE LISTING

```
<160> NUMBER OF SEQ ID NOS: 6

<210> SEQ ID NO 1
<211> LENGTH: 104
<212> TYPE: DNA
<213> ORGANISM: artificial
<220> FEATURE:
<223> OTHER INFORMATION: coll-sense oligonucleotide

<400> SEQUENCE: 1
```

```
cactgtgtcg acgcgtgcaa ggactctata tatacagagg gagcttccta gctgggatat    60
tggagcagca agaggctggg aagccatcac ttaccttgca ctga                     104

<210> SEQ ID NO 2
<211> LENGTH: 112
<212> TYPE: DNA
<213> ORGANISM: artificial
<220> FEATURE:
<223> OTHER INFORMATION: coll-rev oligonucleotide

<400> SEQUENCE: 2
tcgagtgaca cagctgcgca cgttcctgag atatatatgt ctccctcgaa ggatcgaccc    60
tataacctcg tcgttctccg acccttcggt agtgaatgga acgtgactct ag           112

<210> SEQ ID NO 3
<211> LENGTH: 95
<212> TYPE: DNA
<213> ORGANISM: artificial
<220> FEATURE:
<223> OTHER INFORMATION: 3xpbARE-sense oligonucleotide

<400> SEQUENCE: 3
caaagagctc tagcttaata ggttcttgga gtactttacg tgcttaatag gttcttggag    60
tactttacgt gcttaatagg ttcttggagt acttt                                95

<210> SEQ ID NO 4
<211> LENGTH: 99
<212> TYPE: DNA
<213> ORGANISM: artificial
<220> FEATURE:
<223> OTHER INFORMATION: 3xpbARE-rev oligonucleotide

<400> SEQUENCE: 4
catggtttct cgagatcgaa ttatccaaga acctcatgaa atgcacgaat tatccaagaa    60
cctcatgaaa tgcacgaatt atccaagaac ctcatgaaa                            99

<210> SEQ ID NO 5
<211> LENGTH: 30
<212> TYPE: DNA
<213> ORGANISM: artificial
<220> FEATURE:
<223> OTHER INFORMATION: pPUR-sense oligonucleotide

<400> SEQUENCE: 5
taaggatccg ctgtggaatg tgtgtcagtt                                      30

<210> SEQ ID NO 6
<211> LENGTH: 30
<212> TYPE: DNA
<213> ORGANISM: artificial
<220> FEATURE:
<223> OTHER INFORMATION: pPUR-rev oligonucleotide

<400> SEQUENCE: 6
agttacatag aatagtacag acctaggcag                                      30
```

IMIDAZOLIDINE DERIVATIVES, USES THEREFOR, PREPARATION THEREOF AND COMPOSITIONS COMPRISING SUCH

RELATED APPLICATIONS

The present application is a Continuation In Part of co-pending U.S. Non-Provisional application Ser. No. 12/227,776, filed Oct. 8, 2009 now abandoned, which, in turn, is a National Stage Application claiming the priority of PCT Application No. PCT/EP2007/005145 filed May 31, 2007, which in turn, claims priority from G.B. Application No. 0610765.0 filed May 31, 2006. Applicants claim the benefits of 35 U.S.C. §120 as to the U.S. Non-Provisional application and the PCT application, and priority under 35 U.S.C. §119 as to the said G.B. application, and the entire disclosures of all applications are incorporated herein by reference in their entireties.

BACKGROUND OF THE INVENTION

The present invention relates to imidazolidine derivatives, their use in therapy, their preparation, and compositions comprising them.

In men, androgens are associated with the development and maintenance of the primary male characteristics (epididymis, vas deferens, prostate, external genitalia) and secondary male characteristics (development of hair, musculature of the larynx, distribution of fatty tissue, behaviour and libido). In addition, they contribute to muscle and bone development, and also act on the hematopoiesis, the central nervous system and sexual function.

In women, androgens have been involved inter alia in the development and maintenance of bone tissue and libido.

Progressive reduction in levels of circulating androgens in aging men (PADAM—partial androgen decline in aging men) contributes to a specific number of clinical manifestations, including osteoporosis, loss of muscle mass and strength, reduction in libido and sexual dysfunction, anaemia and a change in cognition, mood swings, depression (see Review in: Kaufman J M and Vermeulen A 2005 The decline of androgen levels in elderly men and its clinical and therapeutic implications Endocr Rev. 2005 26:833-76). However, the clinical safety of androgen therapy for cardiovascular and prostate diseases is uncertain. Therefore, androgen supplementation is not recommended for healthy, elderly men (Liu PY et al. 2004 Clinical review 171: The rationale, efficacy and safety of androgen therapy in older men: future research and current practice recommendations. J. Clin. Endocrinol. Metab. 89:4789-96).

Normal development and functioning of the prostate depend on the androgens and their receptor. Androgens play a significant part in the development and progression of prostate cancers (Heinlein C A and Chang C 2004 Androgen receptor in prostate cancer. Endocr. Rev. 25:276-308). Men affected by prostate cancer and treated by chemical castration suffer bone loss which is 5 to 10 times greater than in patients not treated by chemical castration. This leads to a greater risk of bone fracture (Greenspan S L et al. 2005 Bone loss after initiation of androgen deprivation therapy in patients with prostate cancer. J. Clin. Endocrinol. Metab. 90:6410-7).

A syndrome associated with the reduction in levels of circulating androgens (ADIF—androgen decline in female) has also been described in women. It can have various causes, including aging, chemotherapy and infection by the AIDS virus. Associated symptoms include: osteoporosis/osteopenia, sarcopenia and muscle weakness, reduction in libido, sexual dysfunction, change of cognition, mood swings, depression. Endometriosis and an increased risk of breast, uterine and ovarian cancers have also been described (Davison S L and Davis S R 2003 Androgens in women. J. Steroid Biochem. Mol. Biol. 85:363-366). The administration of high doses of androgens to women can lead to the appearance of signs of masculinisation, mood swings and acne. These risks must be taken into consideration when administering androgens to women.

Selective modulators of the androgen receptor (SARMs—selective androgen receptor modulators) of non-steroidal structure are molecules which act as ligands of the androgen receptor with a degree of tissue specificity. Substances which are selective modulators of the androgen receptor are particularly desired because they allow the beneficial effects of testosterone on specific organs (bone and muscle tissue) and on the libido to be maintained, and are less likely to lead to secondary effects in specific tissues, such as the prostate in men and the uterus in women. They represent a safer alternative to conventional therapies in any pathologies linked with an androgen deficit, including osteoporosis or sarcopenia, and decline in libido associated with syndromes of the PADAM and ADIF type. They may also be used in the treatment of cachexia induced by specific diseases, such as cancer or AIDS, or in the treatment of muscle loss induced by long-term treatment with glucocorticoids. They may also be used for male contraception and the treatment of hormone-dependent cancers of the prostate and benign hyperplasia of the prostate.

EP-A-704448 discloses imidazolidine derivatives having the structure:

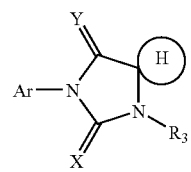

wherein Ar represents aryl optionally substituted by cyano, halogen, trifluoromethyl or an acid or ester radical, X and Y represent O or S, and the encircled H represents an optionally substituted saturated heterocycle comprising oxygen, nitrogen or sulphur atoms. These derivatives are described as having anti-androgen activity.

EP-A-494819 discloses derivatives having the structure:

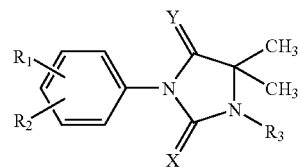

in which $R_1$ and $R_2$ are cyano, nitro, halogen or trifluoromethyl and X and Y are O or S. These derivatives are described as having anti-androgen activity.

EP-A-578516, WO 95/18794, WO 97/19064 and WO 97/23464 all disclose derivatives having the structure:

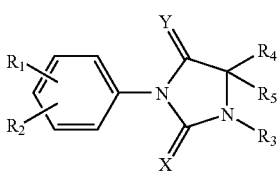

in which $R_1$ and $R_2$ are cyano, nitro, halogen or trifluoromethyl, $R_4$ and $R_5$ represent optionally substituted alkyl radicals or form a cycle having from 3 to 7 members optionally containing 1 or more heteroatoms and X and Y are O or S. These derivatives are described as binding to the androgen receptor and as having anti-androgen activity.

WO 03/096980 discloses derivatives having the structure:

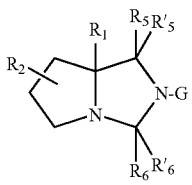

in which the radicals $R_5$, $R'_5$, $R_6$, $R'_6$ can respectively form together oxo or thioxo radicals, and G is an optionally substituted aryl radical. These derivatives are described as modulators of the androgen receptor.

Nothing in the art suggests that monocyclic hydantoin derivatives disubstituted by aryl radicals might have SARM activity, owing to the highly conserved nature of the androgen receptors.

Other imidazolidine derivatives having a similar structure have been described in the phytosanitary field. Hence, U.S. Pat. No. 4,977,270 discloses compounds having the structure:

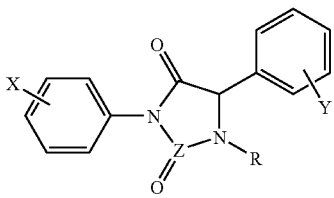

in which R is a lower alkyl, X and Y can be H, halogen, lower alkyl, trifluoromethyl or lower alkoxy, and Z is a carbon or sulphur atom. These derivatives may be used as herbicides.

There is nothing to indicate that such substances might have therapeutic activity.

Aryl-thiohydantoins having the structure:

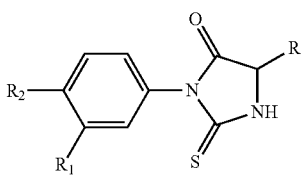

in which R is an amino-acid radical, $R_1$ can be Cl or $CF_3$ and $R_2$ can be H or Cl are described as anti-nociceptive compounds which act as enkephalinase inhibitors [J. Zhou, Z. Yu and M. Li, Zhongguo Yaoke Daxue Xuebao, 22(6), 330-333, (1991)].

SUMMARY OF THE INVENTION

Surprisingly, it has now been found that diaryl substituted imidazolidine derivatives have excellent activity at androgen receptors.

Thus, in a first aspect, the present invention provides the use of a compound of formula (I):

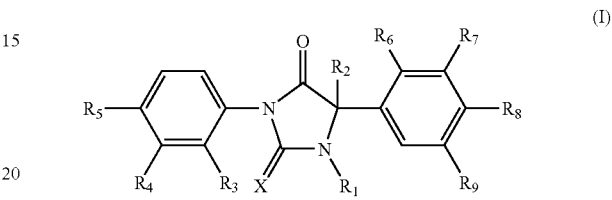

(I)

wherein
X is O or S,
$R_1$ represents acyl, aldehyde, cycloalkyl group or is a straight or branched alkyl, alkenyl, alkynyl, hydroxyalkyl, hydroxyalkenyl, hydroxyalkynyl, haloalkyl, haloalkenyl, or haloalkynyl group; alkylsulphonyl; arylsulphonyl optionally substituted by one or more substituents, which may be the same or different, selected from the group b as defined below; alkylenedioxy groups; alkoxycarbonyl; aralkoxycarbonyl; aryloxycarbonyl; alkoxycarbonylalkyl; aralkoxycarbonylalkyl; aryloxycarbonylalkyl; trifluoromethyl; a straight or branched alkyl group substituted with an aryl group, a cycloalkyl or heterocyclyl group, alkoxy, alkoxy-substituted alkyl, alkylthio and the oxidised sulphoxide and sulphone forms thereof, alkylenedioxy groups; cyano, amino, alkylamino, aralkylamino, arylamino, dialkylamino, diaralkylamino, diarylamino, acylamino, trifluoromethylcarbonylamino, fluoroalkylcarbonylamino, diacylamino, aminocarbonyl, alkylaminocarbonyl, dialkylaminocarbonyl, or oxo group; and wherein any cycloalkyl or heterocyclyl groups or any aryl component is mono- or bi-cyclic and is optionally substituted by one or more substituents, which may be the same or different, selected from the group b, wherein the group b consists of: halogen atoms; hydroxyl; aldehyde groups; straight and branched alkyl, alkenyl, alkynyl, hydroxyalkyl, hydroxyalkenyl, hydroxyalkynyl, haloalkyl, haloalkenyl, and haloalkynyl groups; straight and branched alkoxyl groups; straight and branched thioalkyl and alkylthio groups; alkoxycarbonyl; hydroxycarbonylalkyl; alkoxycarbonylalkyl; perfluoroalkyl; perfluoroalkoxy; —CN; acyl; amino, alkylamino, dialkylamino, acylamino groups; alkyl groups substituted with an amino, alkylamino, dialkylamino, acylamino, or diacylamino group; $CONH_2$; alkylamido groups; alkylthio and the oxidised sulphoxide and sulphone forms thereof; alkylenedioxy groups; and sulphonamide or alkylsulphonamide groups;

$R_2$ represents a hydrogen atom, a straight or branched alkyl group, hydroxyalkyl, haloalkyl, alkenyl, or alkynyl group; alkoxy- or alkenyloxy-substituted alkyl; alkylcarbonyl; alkoxycarbonylalkyl; or trifluoromethyl group;

$R_3$ and $R_4$, which may be the same or different, each represents a hydrogen atom, a halogen atom, a hydroxyl group, trifluoromethyl, a straight or branched alkyl, alkenyl, alkynyl, hydroxyalkyl, haloalkyl, haloalkenyl, or haloalkynyl group; a straight or branched alkoxyl group; or a straight or branched alkylthio group, or $R_3$ and $R_4$, together, represent an, optionally aromatic or heterocyclic, ring having the carbons to which they are attached forming a part of said ring, and being optionally further substituted by substituents b, $R_5$ represents a hydrogen atom, a halogen atom, trifluoromethyl, —CN, or an —$NO_2$ group;

provided that not all of $R_3$, $R_4$, and $R_5$ represents H, $R_6$ and $R_9$ are the same or different, and each represents hydrogen, halogen, hydroxyl; a straight or branched alkyl group, hydroxyalkyl, haloalkyl, alkenyl, or alkynyl group; a straight or branched alkoxyl group; or a straight or branched thioalkyl group;

$R_7$ and $R_8$ are the same or different, and each represents hydrogen, halogen, hydroxyl, sulphydryl; a straight and branched alkoxyl group optionally substituted by one or more hydroxyl groups and/or halogen atoms; a straight or branched alkylthio group optionally substituted by one or more hydroxyl groups and/or halogen atoms; and wherein at least one of $R_7$ and $R_8$ is a hydroxyl; a straight or branched alkoxyl group; a straight or branched alkylthio group;

or $R_7$, $R_8$ and $R_9$ are as defined, and $R_6$ is $C_{1-3}$-alkyl or, together with either $R_1$ or $R_2$, represents a methylene, ethylene, ethenylene, propylene, or propenylene linking group, optionally substituted by one or more methyl, trifluoromethyl, hydroxyl or halogen atoms, and wherein any alkyl components contain from 1 to 6 carbon atoms, unless otherwise specified, and any alkenyl or alkynyl components contain from 2 to 6 carbon atoms, and are optionally substituted by at least one halogen atom or hydroxy group, and wherein any aryl component is optionally a heteroaryl group, and pharmaceutically acceptable salts and esters thereof, in the manufacture of a medicament for the modulation of one or more androgen receptors.

A preferred meaning for $R_1$ is acyl, aldehyde, cycloalkyl group or is a straight or branched alkyl, alkenyl, alkynyl, hydroxyalkyl, hydroxyalkenyl, hydroxyalkynyl, haloalkyl, haloalkenyl, or haloalkynyl group; alkoxycarbonyl; aralkoxycarbonyl; aryloxycarbonyl; alkoxycarbonylalkyl; aralkoxycarbonylalkyl; aryloxycarbonylalkyl; trifluoromethyl; a straight or branched alkyl group substituted with an aryl group, a cycloalkyl or heterocyclyl group, alkoxy, alkoxy-substituted alkoxy, alkylthio, cyano, amino, alkylamino, aralkylamino, arylamino, dialkylamino, diaralkylamino, diarylamino, acylamino, trifluoromethylcarbonylamino, fluoroalkylcarbonylamino, diacylamino, aminocarbonyl, alkylaminocarbonyl, dialkylaminocarbonyl, or oxo group; and wherein any cycloalkyl or heterocyclyl groups or any aryl component is mono- or bi-cyclic and is optionally substituted by one or more substituents, which may be the same or different, selected from the group b.

It is also preferred that $R_3$ and $R_4$, which may be the same or different, each represents a hydrogen atom, a halogen atom, trifluoromethyl, a straight or branched alkyl, alkenyl, alkynyl, hydroxyalkyl, haloalkyl, haloalkenyl, or haloalkynyl group; a straight or branched alkoxyl group; or a straight or branched alkylthio group, or $R_3$ and $R_4$, together, represent an, optionally aromatic or heterocyclic, ring having the carbons to which they are attached forming a part of said ring, and being optionally further substituted by substituents b.

DETAILED DESCRIPTION OF THE INVENTION

Where compounds of the invention are referred to, this includes reference to all compounds for use in the present invention, as defined above and elsewhere herein, whether novel or otherwise, and includes reference to the salts and esters of the compounds of formula (I).

Novel compounds, as provided by the present invention, are as defined above, provided that, when X is O, $R_1$ is alkyl, and $R_2$ is hydrogen, then at least one of $R_7$ and $R_8$ is a hydroxyl, or a sulphydryl.

Compounds wherein at least one of $R_7$ and $R_8$ is a hydroxyl, or a sulphydryl are generally preferred, and especially those wherein one of $R_7$ and $R_8$ is a hydroxyl.

Esters of the compounds of the invention have been found to be useful and, without being bound by theory, it is likely that these serve as prodrugs. Thus, compounds wherein at least one —OH group is present and is in the form of an ester form a preferred aspect of the invention.

Preferred esters are acyl esters, carbonates, and carbamates.

Preferred acyl esters and carbonates take the form —(CO)$R_{11}$, wherein $R_{11}$ represents cycloalkyl, or a straight or branched alkyl, alkenyl, alkynyl, alkoxyl, hydroxyalkyl, hydroxyalkenyl, hydroxyalkynyl, haloalkyl, haloalkenyl, or haloalkynyl group; aralkyl; heteroaralkyl; aryl; heteroaryl; heterocyclyl; trifluoromethyl; a straight or branched alkyl group substituted with an aryl group, a heteroaryl group, a cycloalkyl or heterocyclyl group, alkoxy, or alkylthio; and wherein any cycloalkyl or heterocyclyl groups or any aryl component is mono- or bi-cyclic and is optionally substituted by one or more substituents, which may be the same or different, selected from the group b.

Particularly preferred carbonates include the alkyl carbonates, such as methyl carbonate, ethyl carbonate, propyl carbonate, butyl carbonate and t-butyl carbonate.

Particularly preferred acyl esters include alkylcarbonyl esters, such as the acetic, propionic, methylpropionic, hexanoic and methyl-substituted hexanoic esters, cycloalkylcarbonyl esters, such as cyclopropylcarbonyloxy and cyclohexylcarbonyloxy, benzoic and substituted benzoic esters, such as alkyl- and alkoxy-substituted benzoyl, and heteroarylcarbonyl groups, such as furoyl and nicotinoyl groups.

Preferred carbamates are unsubstituted or substituted by one or two groups selected from: cycloalkyl; a straight or branched alkyl, alkoxyl, hydroxyalkyl, or haloalkyl group; aralkyl; heteroaralkyl; aryl; heteroaryl; heterocyclyl; trifluoromethyl; and straight or branched alkyl groups substituted with an aryl group, a heteroaryl group, a cycloalkyl or heterocyclyl group, alkoxy, or alkylthio. Particularly preferred carbamates are N-alkyl- and N,N-dialkyl-carbamates, including methylcarbamate, dimethylcarbamate, ethylcarbamate, diethylcarbamate, dimethylethylcarbamate, propylcarbamate, butylcarbamate and t-butylcarbamate.

Preferred substituent for esterification is $R_1$.

Any cycloalkyl, heterocyclyl or aryl components may be mono-, bi- or tri-cyclic, unless otherwise indicated. Most preferred are monocyclic groups. Bicyclic and tricyclic groups preferably comprise at least one aromatic ring, and preferably two or three, as appropriate. Individual rings in such groups may have 4, 5, 6, 7, or 8 members. Aromatic rings preferably have 5 or 6 members, and 5-membered aromatic rings preferably contain one or more heteroatoms. In bicyclic and tricyclic ring systems, it is preferred that at least one ring has 6 members and that a second ring have 5, 6, or 7 members (ring atoms) of which two are shared with the 6-membered ring.

Aryl groups include heteroaryl groups, unless otherwise indicated, and preferably comprise oxygen, nitrogen and/or sulphur as heteroatoms.

Other, non-exclusive examples of aryl and heteroaryl groups include, phenyl, naphthyl, or thienyl, furyl, imidazolidine, pyrazolyl, isoxazolyl, isothiazolyl, pyridyl, pyrazinyl, pyrimidinyl, triazinyl, benzothienyl, benzofuryl, isoindolyl, isobenzofuranyl, quinolyl, isoquinolyl, naphthyridinyl, and quinazolinyl.

Heterocyclyl groups may be saturated or unsaturated and comprise one or more heteroatoms, preferably selected from oxygen, sulphur and nitrogen. Preferred heterocyclyl groups contain from 5 to 10 members and 1 to 4 heteroatoms in mono- or polycyclic form. Examples include, azetidinyl, thienyl, furyl, pyrrolyl, pyrrolidinyl, imidazolyl, imidazolidinyl, thiadiazolyl, oxadiazolyl, pyrazolyl, isoxazolyl, isothiazolyl, tetrazolyl, pyridyl, pyrazinyl, pyrimidinyl, triazinyl, piperazinyl, piperidinyl, morpholino, thiomorpholino, pyranyl, thiopyrannyl, indolyl, isoindolyl, benzothienyl, benzofuryl, isobenzofuranyl, quinolyl, isoquinolyl, naphthyridinyl, quinazolinyl, quinuclidinyl, and chromenyl.

Exemplary unsaturated heterocycles include, imidazole, pyrazole, indazole, benzimidazole, purine, aza-benzimidazole, triazole, pyrrole, indole, isoindazole, and azaindole.

Preferred saturated heterocycles are morpholinyl, thiomorpholinyl, piperazinyl, homopiperazinyl, and piperidinyl groups, preferably morpholinyl and thiomorpholinyl, and particularly morpholinyl.

It is preferred that X is oxygen.

In preferred compounds of the present invention, $R_1$ is a cycloalkyl group or is a straight or branched alkyl, alkenyl, alkynyl, hydroxyalkyl, hydroxyalkenyl, hydroxyalkynyl, haloalkyl, haloalkenyl, or haloalkynyl group; alkoxycarbonylalkyl; trifluoromethyl; a straight or branched alkyl group substituted with an aryl group, a cycloalkyl or heterocyclyl group, alkoxy, alkoxy-substituted alkoxy, amino, alkylamino, dialkylamino, aminocarbonyl, alkylaminocarbonyl, dialkylaminocarbonyl, or oxo group.

The substituents forming group b are preferably selected from: halogen atoms; hydroxyl; straight and branched alkyl, alkenyl, alkynyl, hydroxyalkyl, hydroxyalkenyl, hydroxyalkynyl, haloalkyl, haloalkenyl, and haloalkynyl groups; straight and branched alkoxyl groups; alkoxycarbonyl; hydroxycarbonylalkyl; alkoxycarbonylalkyl; trifluoromethyl; amino, alkylamino, dialkylamino groups; alkyl groups substituted with an amino, alkylamino, or dialkylamino group; $CONH_2$; alkylamido groups; methylenedioxy and ethylenedioxy groups; and sulphonamide or alkylsulphonamide groups.

It is preferred that $R_2$ is a hydrogen atom, a straight or branched alkyl group, hydroxyalkyl, haloalkyl, or a trifluoromethyl group.

It is preferred that $R_3$ is hydrogen or a straight or branched alkyl.

It is preferred that $R_4$ is halogen, trifluoromethyl, or a straight or branched alkyl or alkoxyl group.

It is preferred that $R_5$ is halogen, $-NO_2$, or $-CN$.

It is particularly preferred that $R_4$ is trifluoromethyl and $R_5$ is $-CN$.

It is preferred that $R_6$ and $R_9$ are both hydrogen.

It is further preferred that $R_7$ is hydrogen.

In preferred compounds of the present invention, $R_8$ is $-OH$.

Any alkyl, alkenyl, or alkynyl chains preferably have no more than 4 carbon atoms. This specifically applies to alkyl, alkenyl, or alkynyl chains without consideration to any side chains or substituents, but preferably includes and alkyl, alkenyl, or alkynyl substituents thereon. Alkyl chains may be those specified in $R_1$, $R_2$, $R_3$ etc. as substituents, and may also be components of other groups, such as aralkyl groups.

It will be appreciated that compounds of the present invention may be in any racemic, enantiomeric and diastereoisomeric isomeric form, where such options arise. The carbon atom to which $R_2$ is attached is a chiral centre, and there is no preference for the orientation of $R_2$.

Salts include addition salts with inorganic and organic acids or bases.

In the compounds of the present invention, where a sulphur atom is present, other than at position X or as part of a ring, then it may be present in the sulphoxide (SO) or sulphone ($SO_2$) forms, where desired.

Any alkylsulphonyl substituent is preferably a trifluoromethyl or methylsulphonyl substituent, and more preferably a methylsulphonyl substituent, such as a methylsulphonylamino, or methylsulphonamide substituent.

In general, carboxyl groups are in the form $-COOH$. Aldehyde groups may be represented as $-CHO$. Acyl groups are carboxylic acid residues generally having the form $RCO-$ where R represents the remainder of the acid residue, such as optionally substituted alkyl, alkenyl, alkynyl, aralkyl, and heterocyclyl groups. Examples of acyl groups are provided in the accompanying Examples. Alkyl may include cycloalkyl.

Cycloalkyl groups may typically contain from 3 to 14 carbon atoms in condensed mono- or polycyclic form and may be, for example, a mono or polycyclic carbocycle, or a polycondensed carbocycle, such as, cyclopropyl, cyclobutyl, cyclopentyl, cyclohexyl, cycloheptyl, bicyclooctanyl, norbornyl, or tricyclo[3.3.1.1]decanyl.

Branched alkyl may take the form of singly or multiply branched alkyl, such as t-butyl or 4-methylpentyl, for example. Alkyl groups preferably contain from 1 to 6 carbons, and more preferably from 1 to 4 carbon atoms. Methyl and ethyl are particularly preferred as substituents. Similar considerations apply to hydroxyalkyl, hydroxyalkenyl, hydroxyalkynyl, haloalkyl, haloalkenyl, haloalkynyl, alkoxy, alkylthio, alkenyl, and alkynyl groups. Hydroxyalkyl may be substituted by one or more hydroxyl groups, but preferably one. Thioalkyl groups typically take the form HS-Alk-, where Alk indicates an alkyl group. Hydroxycarbonylalkyl groups typically take the form HOOC-Alk-. Alkylcarbonyl groups take the form Alk-CO—, while alkoxycarbonylalkyl groups take the form AlkOCOAlk-. Alkoxycarbonyl groups take the form AlkOCO—. Aralkoxycarbonyl, aryloxycarbonyl and other aryl substituted components replace or substitute the alkyl in the preceding groups, so that they take the form ArAlk-OCO— and Ar—OCO—, for example, with other aryl containing groups being constructed in a similar manner. Alkylthio groups take the form Alk-S— and are optionally in the sulphoxide (Alk-SO—) or sulphone (Alk-$SO_2$—) forms. Any alkyl component preferably has from 1 to 6 carbon atoms, so that alkoxycarbonylalkyl may be hexyl-5-pentanoate or methylmethanoate for example. Alkenyl and alkynyl components have from 2 to 6 carbon atoms, and take the form of an alkyl group possessing at least one double or triple bond between adjacent carbons. It is preferred that there is only one such unsaturated bond per alkenyl or alkynyl substituent.

Alkylamino and dialkylamino groups take the form RNH— and $R_2N$— respectively, with other substituted amino groups taking similar form. For example, acylamino takes the form RCONH—. Aminocarbonyl takes the form $-CONH_2$, while dialkylaminocarbonyl takes the form $R_2NCO-$, similar considerations applying to other substituted aminocarbonyl groups. It will be appreciated that alkyl groups substituted by an oxo group may also be considered to be acylalkyl groups.

Where multiple substituents are selected from a common group, such as substituents b, then each substituent is the same or different.

Preferred alkyl groups are methyl and ethyl, and it is further preferred that these are unsubstituted or substituted with one or more fluorine atoms.

Hydroxyalkyl, hydroxyalkenyl, and hydroxyalkynyl groups have one or more hydroxyl groups, preferably one. Similarly, haloalkyl, haloalkenyl, and haloalkynyl groups have one or more halogen atoms present thereon. In general, halogen is preferably selected from iodine, bromine, chlorine and fluorine, preferably chlorine or fluorine. Perhalo substituents are preferably perfluoro substituents, preferably trifluoromethyl. Where an alkyl group is specified herein, then this may include haloalkyl, particularly fluoroalkyl, and especially trifluoromethyl groups, although unsubstituted alkyls are generally preferred over halo-substituted alkyls. The most preferred haloalkyl group is trifluoromethyl. Straight and branched alkoxyl groups and straight and branched alkylthio and alkylthio groups are as defined above for straight and branched alkyl groups. Aralkoxy groups take the form Ar-AlkO—, while aryloxy and arylthio groups take the form ArO— and ArS—, respectively, where Ar is an aryl or heteroaryl group. Arylthio groups may also be oxidised to their arylsulphonyl form. It will be understood that similar considerations apply to aralkoxycarbonyl and aryloxycarbonyl, and other groups specifying aralkoxy and aryloxy.

Alkyl-, aralkyl-, and aryl-amido groups have the appropriate groups linked via the nitrogen, such as —CONH-Alk. Amido takes the form of —CONH—, so that alkylamido takes the form —CONH-alkyl, for example, while aralkylamido takes the form —CONH-AlkAr. It will be appreciated that these may also be considered to be substituted aminocarbonyl groups.

Sulphonamide, alkylsulphonamide, di(alkylsulphonyl) amino, aralkylsulphonamide, di(aralkylsulphonyl)amino, arylsulphonamide, and di(arylsulphonyl)amino are of the form sulphonyl or disulphonyl substituted on nitrogen, such as Alk-$SO_2$—NH—.

Alkoxycarbonylamino groups take the form Alk-O—CONH—, and aralkoxycarbonylamino, aryloxycarbonylamino, alkylcarbonylamino, aralkylcarbonylamino, and arylcarbonylamino groups should be construed accordingly. Alkylaminocarbonyloxy groups take the form Alk-NH-COO—, and aralkylaminocarbonyloxy and arylaminocarbonyloxy groups should be construed accordingly.

When $R_3$ and $R_4$ represent a ring, this may be saturated or unsaturated, and may have 5, 6, or 7 members, including the carbons to which $R_3$ and $R_4$ are attached. The ring may contain only carbon atoms, and simply form a fused phenyl group, optionally substituted with a substituent selected from group b. The ring may also be an alkylene group, such as propylene or butylene, or may be an alkenylene, such as 2-butenylene. Alternatively, the ring formed by $R_3$ and $R_4$ may be an alkylene-dioxy group, such methylenedioxy, ethylenedioxy or propylenedioxy. Although these groups may be substituted, it is generally preferred that they be unsubstituted.

When $R_6$ forms a linking group with either $R_1$ or $R_2$, this may be a methylene, ethylene, ethenylene, propylene, or propenylene linking group, optionally substituted by one or more methyl, trifluoromethyl, hydroxyl or halogen atoms. More preferably, the linking group is saturated, and is preferably unsubstituted. When the linking group is formed with $R_1$, then it is preferably methylene or ethylene, particularly preferably methylene. When the linking group is formed with $R_2$, then it is preferably ethylene or propylene, particularly preferably ethylene.

By the term 'pharmaceutically acceptable' is meant a compound which may be administered to a patient in respect of an indicated condition with the expectation that the patient will benefit from the treatment. It is, thus, possible for a compound of the invention to have mildly toxic effects provided that there is an overall benefit to the patient. However, it is preferred that compounds of the invention have little, or preferably no, toxicity when administered in effective quantities for the desired indications.

Suitable salts are any salts of acidic or basic compounds of the invention, and are may be formed with organic or inorganic acids or bases. Preferred salts are alkali metal or alkali earth metal salts. Esters are preferably organic esters, as exemplified elsewhere herein, but may also be esters with inorganic acids, such as sulphuric or nitric acids.

Preferred compounds of the invention are, individually:
1-(3,4-dichlorophenyl)-4-(4-hydroxyphenyl)-3-methylimidazolidine-2,5-dione,
1-(3,4-dichlorophenyl)-4-(4-hydroxyphenyl)-3-(2-propenyl)imidazolidine-2,5-dione,
4-[2,5-dioxo-4-(4-hydroxyphenyl)-3-(2-propynyl)imidazolidin-1-yl]-2-trifluoromethylbenzonitrile,
4-[3,4-dimethyl-2,5-dioxo-4-(4-hydroxyphenyl)imidazolidin-1-yl]-2-trifluoromethyl-benzonitrile,
4-[2,5-dioxo-4-(4-hydroxyphenyl)-4-methyl-3-(2-propynyl)-imidazolidin-1-yl]-2-trifluoromethylbenzonitrile,
4-[4-(4-hydroxyphenyl)-4-methyl-5-oxo-3-(2-propenyl)-2-thioxoimidazolidin-1-yl]-2-trifluoromethylbenzonitrile,
2-chloro-4-[3,4-dimethyl-2,5-dioxo-4-(4-hydroxyphenyl) imidazolidin-1-yl]-3-methyl-benzonitrile,
4-[3,4-dimethyl-2,5-dioxo-4-(4-hydroxyphenyl)imidazolidin-1-yl]-2-methoxy-benzonitrile,
(R)-4-[3,4-dimethyl-2,5-dioxo-4-(4-hydroxyphenyl)imidazolidin-1-yl]-2-trifluoromethylbenzonitrile,
1-(3,4-dichlorophenyl)-4-hydroxymethyl-4-(4-hydroxyphenyl)-3-methyl-imidazolidine-2,5-dione,
4-[4-hydroxymethyl-4-(4-hydroxyphenyl)-3-methyl-2,5-dioxoimidazolidin-1-yl]-2-trifluoromethylbenzonitrile,
4-[4-fluoromethyl-4-(4-hydroxyphenyl)-3-methyl-2,5-dioxoimidazolidin-1-yl]-2-trifluoromethylbenzonitrile,
4-[3-(2-butynyl)-4-(4-hydroxyphenyl)-4-methyl-2,5-dioxoimidazolidin-1-yl]-2-trifluoromethyl-benzonitrile,
4-[4-(4-hydroxyphenyl)-3-methoxymethyl-4-methyl-2,5-dioxoimidazolidin-1-yl]-2-trifluoromethylbenzonitrile,
(R)-4-[3,4-dimethyl-2,5-dioxo-4-(4-hydroxyphenyl)imidazolidin-1-yl]-2-methoxybenzonitrile,
(R)-4-[4-fluoromethyl-4-(4-hydroxyphenyl)-3-methyl-2,5-dioxoimidazolidin-1-yl]-2-trifluoromethylbenzonitrile,
4-[2,5-dioxo-4-(4-hydroxyphenyl)-3-methoxymethyl-4-methylimidazolidin-1-yl]-2-trifluoromethylbenzonitrile, and
(R)-4-[2,5-dioxo-4-(4-hydroxyphenyl)-3-methoxymethyl-4-methylimidazolidin-1-yl]-2-trifluoromethylbenzonitrile.

Suitable indications for prophylaxis or therapy with compounds of the invention include: cachexia; osteoporosis; sarcopenia; decline in libido and/or sexual dysfunction, especially when associated with androgen deficiency; muscle loss induced by chronic treatment with glucocorticoids; hormone-dependent cancers of the prostate; and benign hyperplasia of the prostate. The compounds of the invention may also be used as a male contraceptive.

Imidazolidine derivatives of general formula (I) are selective modulators of the androgen receptor and are therefore of particular benefit in the prophylactic and/or curative treatment of osteoporosis or sarcopenia, decline in libido and sexual dysfunction associated with syndromes of the PADAM and ADIF type. They may also be used in the treatment of cachexia induced by specific diseases such as cancer or AIDS or in the treatment of muscle loss induced by long-term treatment with glucocorticoids. They may also be used for male contraception and the treatment of hormone-dependent cancers of the prostate and benign hyperplasia of the prostate.

Other preferred embodiments of the invention are those in which:

$R_1$ represents an alkyl radical containing from 1 to 4 carbon atoms in a straight or branched chain optionally substituted [by fluorine or chlorine atoms, by hydroxy, alkyloxy, alkyloxyalkyloxy, acyl radicals, by a cyano radical, by an aryl or heteroaryl radical containing from 5 to 10 members in mono- or polycyclic form, and 1 or 2 heteroatoms selected from nitrogen, oxygen or sulphur, the aryl and heteroaryl radicals themselves being able to be substituted by one or more hydroxy or alkyloxy radicals containing 1 or 2 carbon atoms or methylenedioxy radicals], an alkenyl or alkynyl radical containing from 2 to 5 carbon atoms in a straight or branched chain optionally mono- or polysubstituted by hydroxy or acyloxy radicals, or else $R_1$ forms with the radical $R_6$ an alkylene radical containing from 1 to 4 carbon atoms in a straight or branched chain; and/or $R_2$ represents a hydrogen atom, an alkyl radical containing from 1 to 4 carbon atoms in a straight or branched chain and optionally substituted by fluorine or chlorine atoms, or by a hydroxy radical, or else $R_2$ forms with $R_6$ an alkylene radical containing from 2 to 4 carbon atoms in a straight or branched chain; and/or $R_3$ and $R_4$ independently of one another represent hydrogen, fluorine or chlorine atoms, alkyl radicals containing 1 or 2 carbon atoms, trifluoromethyl or alkyloxy radicals of which the alkyl portion contains 1 or 2 carbon atoms, or else $R_3$ forms with $R_4$ an alkylene or alkylenylene radical containing from 3 to 4 carbon atoms, or 1,4-butadienylene or a methylenedioxy or ethylenedioxy radical, $R^5$ represents a fluorine or chlorine atom or a nitro, cyano or trifluoromethyl radical, and wherein only one of $R_3$, $R_4$ and $R_5$ may be hydrogen; and/or $R_6$ represents a hydrogen, fluorine or chlorine atom, a methyl radical, or $R_6$ forms with $R_1$ or with $R_4$ an alkylene radical respectively containing from 1 to 4 or 2 to 4 carbon atoms in a straight or branched chain; and/or one of $R_7$ and $R_8$ represents a hydrogen or fluorine atom and the other —OH; and/or $R_9$ represents a hydrogen atom; and/or Some preferred novel products include those wherein:
X represents a sulphur atom and $R_1$ represents an alkyl radical containing from 1 to 4 carbon atoms in a straight or branched chain optionally substituted [by fluorine or chlorine atoms, by hydroxy, alkyloxy, alkyloxyalkyloxy, acyl radicals, by a cyano radical, by an aryl or heteroaryl radical containing from 5 to 10 members in mono- or polycyclic form, and 1 or 2 heteroatoms selected from nitrogen, oxygen or sulphur, the aryl and heteroaryl radicals themselves being able to be substituted by one or more hydroxy or alkyloxy radicals containing 1 or 2 carbon atoms or methylenedioxy radicals], an alkenyl or alkynyl radical containing from 2 to 5 carbon atoms in a straight or branched chain optionally mono- or polysubstituted by hydroxy or acyloxy radicals or else $R_1$ forms with the radical $R_6$ an alkylene radical containing from 1 to 4 carbon atoms in a straight or branched chain, $R_2$ represents a hydrogen atom, an alkyl radical containing from 1 to 4 carbon atoms in a straight or branched chain and optionally substituted by fluorine or chlorine atoms, or by a hydroxy radical, or else $R_2$ forms with $R_6$ an alkylene radical containing from 2 to 4 carbon atoms in a straight or branched chain, $R_3$ and $R_4$ independently of one another represent hydrogen, fluorine or chlorine atoms, alkyl radicals containing 1 or 2 carbon atoms, trifluoromethyl or alkyloxy radicals of which the alkyl portion contains 1 or 2 carbon atoms, or else $R_3$ forms with $R_4$ an alkylene or alkylenylene radical containing from 3 to 4 carbon atoms, or 1,4-butadienylene or a methylenedioxy or ethylenedioxy radical, $R_5$ represents a hydrogen, fluorine or chlorine atom or a nitro, cyano or trifluoromethyl radical, at least two of $R_3$, $R_4$ and $R_5$ being different from the hydrogen atom, $R_6$ represents a hydrogen, fluorine or chlorine atom, a methyl radical, or else $R_6$ forms with $R_1$ or with $R_2$ an alkylene radical respectively containing from 1 to 4 or 2 to 4 carbon atoms in a straight or branched chain, $R_7$ and $R_8$ represent a hydrogen, fluorine or chlorine atom or an alkyl radical containing 1 or 2 carbon atoms and the other an —OH radical, $R_9$ represents a hydrogen atom, and or those wherein X represents an oxygen atom and $R_2$ represents an alkyl radical containing from 1 to 4 carbon atoms in a straight or branched chain and optionally substituted by fluorine or chlorine atoms, or by a hydroxy radical or else $R_2$ forms with $R_6$ an alkylene radical containing from 2 to 4 carbon atoms in a straight or branched chain, and the radicals $R_1$ and $R_3$ to $R_9$ are as defined when X is a sulphur atom, or those wherein X represents an oxygen atom and either $R_1$ represents an alkyl radical containing from 1 to 4 carbon atoms in a straight or branched chain substituted [by fluorine or chlorine atoms, by hydroxy, alkyloxy, alkyloxyalkyloxy, acyl radicals, by a cyano radical, by an aryl or heteroaryl radical containing from 5 to 10 members in mono- or polycyclic form, and 1 or 2 heteroatoms selected from nitrogen, oxygen or sulphur, the aryl and heteroaryl radicals themselves being able to be substituted by one or more hydroxy or alkyloxy radicals containing 1 or 2 carbon atoms or methylenedioxy radicals], an alkenyl or alkynyl radical containing from 2 to 5 carbon atoms in a straight or branched chain optionally mono- or polysubstituted by hydroxy or acyloxy radicals or else $R_1$ forms with the radical $R_6$ an alkylene radical containing from 1 to 4 carbon atoms in a straight or branched chain, and $R_2$ to $R_9$ are as defined when X is a sulphur atom, The compounds of the present invention may be prepared as follows:

by action of an isocyanate or an isothiocyanate of general formula (II):

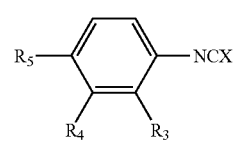

(II)

in which X, $R_3$, $R_4$ and $R_5$ are defined, on an ester derived from 4-hydroxyphenylglycine of general formula (III):

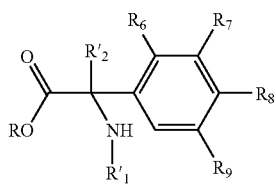
(III)

in which $R_6$, $R_7$, $R_8$ and $R_9$ are as defined, $R'_2$ is a hydrogen atom or is as defined for $R_1$, $R'_2$ is a hydrogen atom or an alkyl radical containing from 1 to 6 carbon atoms in a straight or branched chain optionally substituted by protected hydroxy radicals, an alkyloxy or alkenyl radical or forms with $R_6$ an alkylene radical containing from 2 to 4 carbon atoms in a straight or branched chain and R is an ester group,
then optionally:
if it is desired to prepare an imidazolidine derivative in which $R_2$ is a 1-hydroxyalkyl radical and if an imidazolidine derivative of general formula (I') in which $R'_1$ is other than the hydrogen atom is obtained, an aldehyde of general formula:

A-CHO (IV)

in which A represents a hydrogen atom or an alkyl group containing from 1 to 5 carbon atoms in a straight or branched chain, is reacted with an imidazolidine derivative of general formula (I'):

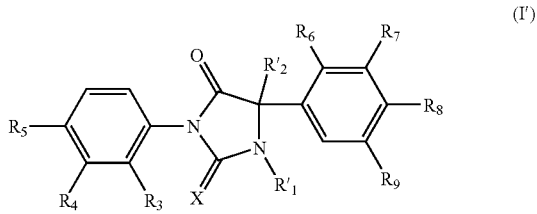
(I')

in which $R'_2$ is hydrogen and X, $R_3$, $R_4$, $R_5$, and $R_6$ to $R_9$ are as defined and $R'_1$ is other than hydrogen, and/or optionally:
in order to obtain an imidazolidine derivative of general formula (I) in which $R_1$ is as defined, X is an oxygen atom and $R_2$ is an alkyl radical optionally substituted by protected hydroxy radicals, alkyloxy or alkenyl radicals or forms with $R_6$ an alkylene radical containing from 2 to 4 carbon atoms in a straight or branched chain, followed by the action of a halogenated derivative, an acid chloride or a chloroformate of general formula

$R_1$-Hal (V)

in which $R_1$ is as defined and Hal is a halogen atom or optionally the action of the acid anhydride or the corresponding carbonate, on the imidazolidine derivative of general formula (I') in which $R'_1$ is a hydrogen atom, X is an oxygen atom and $R'_2$ is other than a hydrogen atom.

In the reaction of the isocyanate or the isothiocyanate of general formula (II) with the ester derived from α-hydroxyphenylglycine of general formula (III), the ester group represented by R is advantageously selected from the alkyl ester groups or any other ester group of which the radical does not risk altering the reaction of the molecular group.

The reaction is preferably conducted under an inert atmosphere (nitrogen for example), in an anhydrous organic solvent such as an ether (for example tetrahydrofuran or dioxan, optionally anhydrous), at a temperature of between 20 and 100° C., preferably between 20 and 50° C., a temperature of about 50° C. being particularly advantageous. A salt of α-hydroxyphenylglycine (for example the hydrochloride) may be used in the presence of a nitrogen-containing base, for example anhydrous pyridine, triethylamine or diisopropylethylamine.

When a derivative of general formula (V) is used in the reaction, Hal may be selected from chlorine, bromine or iodine. Preferably, Hal is a bromine or iodine atom when the derivative of general formula (V) is an alkyl halide and a chlorine atom when the derivative of general formula ((V) is an acyl, carbamoyl or alkyloxycarbonyl halide.

In the reactions of the derivatives of formula (V) on the imidazolidine derivative of general formula (I'), it will be appreciated that, when $R_1$ contain radicals which might interfere with the reaction, then they may be protected by any known method which does not affect the molecular group, the protecting radicals being removed after the reaction, also by known methods which do not affect the molecular group. In particular the protecting radicals may be protected and removed by the methods described by Greene, Wuts, Protective Group in Organic Synthesis, J. Wiley (1991).

The reaction may be conducted under an inert atmosphere (for example under nitrogen) in the presence of a nitrogen-containing base such as for example pyridine or triethylamine, in an organic solvent such as a chlorinated solvent (dichloromethane, dichloroethane, chloroform for example); it is possible to work with or without a solvent, particularly when working in the presence of pyridine. The reaction is conducted at a temperature of between 20 and 100° C., preferably at a temperature of between 20 and 50° C. The reaction may also be conducted in the presence of an inorganic base such as an alkaline hydroxide (for example sodium hydroxide) in a solvent such as acetone or methyl ethyl ketone, at a temperature of between 20 and 50° C., or else in the presence of an alkaline carbonate such as potassium carbonate, in a polar solvent (dimethylformamide for example) at a temperature of between 20 and 100° C., preferably between 50 and 80° C.

The subsequent substitution of $R_2$ is conducted by action of an aldehyde of formula (V) on the imidazolidine derivative of general formula (I') in which $R'_2$ is a hydrogen atom, while working in an inert atmosphere (under nitrogen for example), in an anhydrous organic solvent such as for example an ether (tetrahydrofuran, dioxan, diethyl ether in particular), by addition of a strong base such as lithium diisopropylamide, in the presence of a chelating solvent such as hexamethylphosphorotriamide at a temperature of −78° C. The reaction is conducted at a temperature of between −78 and 0° C.

The intermediate isocyanates or isothiocyanates of general formula (II) may be prepared respectively by the action of phosgene or triphosgene on the corresponding anilines in a mixture of toluene and an ether (dioxan for example) at a temperature of between 100 and 110° C. in the case of isocyanates, and by action of thiophosgene in water, at a temperature of approximately 20-25° C. in the case of isothiocyanates.

The anilines used for preparing intermediates of general formula (II) may be prepared by the method described in WO 03/096980, or by a similar method.

The esters of general formula (III) derived from α-hydroxyphenylglycine, in which R, $R'_1$, $R'_2$, $R_6$, $R_7$, $R_8$ and $R_9$ are as defined, may be prepared from the corresponding bromine derivative of general formula:

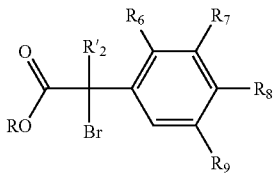
(VI)

in which R, R'$_2$, R$_6$ and R$_9$ are as defined, and one of R$_7$ or R$_8$ represents an acetyloxy radical, a protected hydroxy radical or an alkyloxy radical, and the other represents a hydrogen or halogen atom or an alkyl radical, by action of an amine of general formula:

R$_1$—NH$_2$ (VII)

in which R$_1$ is as defined, or else ammonia if it is desired to obtain a derivative of general formula (III) in which R'$_1$ is a hydrogen atom, then the acetyl radical or optionally the hydroxy protecting radical, represented by R$_7$ or R$_8$ is removed and/or this radical is replaced by a radical R$_{10'}$.

The reaction is conducted in an organic solvent such as an alcohol or ether at a temperature of between 20 and 50° C.

When R'$_1$, in the product of general formula (III), is a hydrogen atom, the products of general formula (III), in which R$_1$ is an optionally substituted alkyl radical of the type B—CH$_2$— may be obtained by reacting an aldehyde of the type B—CHO in the presence of a reducing agent such as sodium cyanoborohydride.

If it is desired to prepare a derivative of general formula (III), which is chiral in terms of the carbon atom carrying the amine, the enantiomers may be separated by any known methods such as chromatography on a chiral support, resolution by enzyme hydrolysis or by crystallisation of a diastereoisomeric salt between the amine function of III and a chiral acid or by the method described by Washburn W N et al. 2004 Bioorg. Med. Chem. Letters 14: 3525-3529 and by Cheng P T W et al. in U.S. Pat. No. 5,770,615 or by a method similar to those described hereinafter in the accompanying Examples.

The esters of general formula (VI) derived from α-hydroxyphenylglycine may be prepared by bromination of the corresponding derivative of general formula:

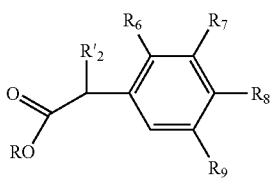
(VIII)

in which R, R'$_2$, R$_6$ and R$_9$ are defined as above for formula (VI), and one of R$_7$ or R$_8$ represents an acetyloxy radical, a protected hydroxy radical or an alkyloxy radical and the other represents a hydrogen or halogen atom or an alkyl radical.

Bromination is conducted in an inert organic solvent at the reflux temperature of the reaction mixture, in particular a chlorine-containing solvent such as carbon tetrachloride, at a temperature of 70 to 90° C., and in the presence of an initiator of free radicals such as azoisobutyronitrile.

The present invention provides, in addition to the above processes, a further process for the preparation of compounds of formula (I) wherein, when R$_2$ is other than hydrogen, comprising the following scheme:

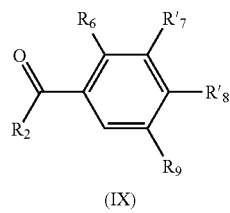
(IX)

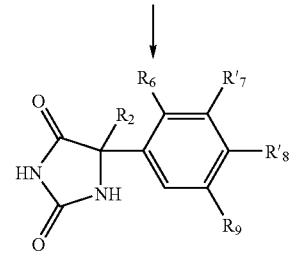
(X)

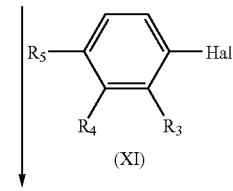
(XI)

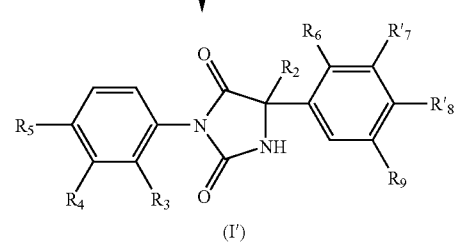
(I')

in which R$_2$ is defined as above, R$_3$ to R$_5$ and R$_6$ and R$_9$ are as defined, and one of R'$_1$ or R'$_4$ represents an optionally protected hydroxy radical or an alkyloxy radical and the other represents a hydrogen or halogen atom or an alkyl radical containing from 1 to 4 carbon atoms in a straight or branched chain, by action of ammonium carbonate and an alkaline cyanide (sodium cyanide for example) on the aryl ketone of general formula (IX), followed by the action of a halogenated derivative of general formula (XI):

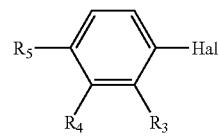
(XI)

in which R$_3$ to R$_5$ are as defined and Hal is a halogen atom, on the imidazolidine dione derivative of general formula (X) obtained:

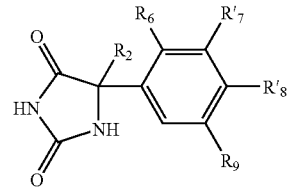
(X)

in which $R_2$, $R_6$ and $R_9$ are as defined and $R'_7$ and $R'_8$ are defined as above, followed by introduction of the radical $R_1$ and removal, optionally, of the protecting radical of $R'_7$ or $R'_8$.

The aryl ketone of formula (IX) is reacted out with alkaline cyanide and ammonium carbonate, using potassium cyanide or sodium cyanide in an aqueous organic medium such as a 50/50 alcohol/water, for example ethanol/water mixture, at a temperature of between 50 and 70° C.

The halide of formula (XI) is reacted with the imidazolidine derivative of general formula (X) in a polar organic solvent such as dimethylformamide or dimethylacetamide, for example, at a temperature of between 110° C. and the reflux temperature of the reaction mixture, and in the presence of a catalyst, especially cuprous oxide.

$R_1$ is introduced under the previously described conditions by action of a halogenated derivative, an acid chloride, a chloroformate or a sulphonyl chloride of general formula (V) or optionally of an acid anhydride or an organic carbonate.

The protecting radical for $R'_7$ or $R'_8$ is removed by conventional methods which do not affect the molecular group. In particular the protecting radicals are removed by the methods described by Greene, Wuts, Protective Group in Organic Synthesis, J. Wiley (1991).

The stereoisomeric forms may be separated by known methods or prepared by stereospecific synthesis. It will be appreciated that these stereoisomeric forms and the mixtures thereof in any proportions fall within the scope of the present invention.

Optionally, depending on the nature of the substituents, the imidazolidine derivatives of formula (I) can form acid addition salts. It will be appreciated that these salts also fall within the scope of the present invention and more particularly the pharmaceutically acceptable salts.

Pharmaceutically acceptable acid addition salts include for example the addition salts with inorganic acids such as hydrochloric, sulphuric or phosphoric acid or with organic carboxylic acids such as acetic, trifluoroacetic, citric, benzoic, lactic, maleic, fumaric, tartaric, methanesulphonic or para toluene sulphonic acid.

The salts of imidazolidine derivatives of general formula (I) may be obtained by conventional methods, known to a person skilled in the art, for example by combining an imidazolidine derivative of general formula (I) with an organic or inorganic acid or a base in a solvent or a dispersant or starting from another salt by cation or anion exchange.

The invention also includes any salts of compounds of general formula (I) which, on account of their low physiological acceptability, cannot be used directly as a medicament, but can be used as intermediates for carrying out subsequent chemical modifications to the compounds of general formula (I) or as starting products for the preparation of physiologically acceptable salts.

The present invention further provides pharmaceutically acceptable compositions comprising compounds as defined in claim 1.

The compounds of the present invention may be administered in any suitable form, including by injection, such i.p., i.m., i.v. or s.c., pessaries, suppositories, tablets, elixirs, potions, capsules, linctus and other oral formulations, lotions, creams, unguents and transdermal patches, and inhalant formulations.

The compound may be prepared in association with any further ingredients, as desired. These may generally include a vehicle and a diluent, and may further include such ingredients as flavourings, coulourings, thickeners, penetration enhancers, sterilising agents and pH adjusting agents, for example. Specific excipients used in pharmaceutical compositions include, talc, gum arabic, lactose, starch, magnesium stearate, cocoa butter, fats of animal or vegetable origin, paraffin derivatives, glycols, various wetting agents, dispersants or emulsifiers and preservatives, which may be selected according to the composition chosen.

The nature of the formulation may be dependent on the condition to be treated. In general, it is desired that the compounds be administered to achieve a systemic effect, so that oral and injection routes are preferred.

The amount of compound to be administered will be readily determined by the physician, and will be dependent on the sex, age and condition of the patient, as well as the condition to be treated, but will generally vary between about 0.1 mg to about 500 mg per patient.

While the preferred category of patient is human, other mammals may also be treated, if desired, for conditions involving androgens, which may be similar to those described above for humans. Types of mammal include domestic and livestock, and preferred animals for treatment include dogs, cats, horses, cows, camels, deer, buffalo, bison and llama. Disorders that may be treated include behavioural disorders such as aggressiveness, and androgen-dependent diseases, such as circum analum in dogs and tumours associated with androgen receptors.

The efficacy of test compounds (compounds of formula (I)) may be demonstrated in vitro in tests of transactivation after simultaneous and stable expression of the human androgen receptor (hAR) and a reporter gene placed under the transcriptional control of the androgen receptor (AR) response elements (ARE) in host cells. This test constitutes a method of identifying pure or partial agonists which mimic the effects of natural hormones, such as DHT (dihydrotestosterone) in the present case or, on the other hand, antagonists which inhibit them.

For this transactivation test, plasmids encoding a reporter gene and the human androgen receptor (hAR) are introduced together by transfection into the HeLa cell line. The reporter plasmid contains luciferase cDNA under the control of the AREs contained in the promoter sequences of the probasin gene (3xpbAREminicoll-luciferase/pGL3-puro). The expression of the reporter gene constitutes an indication of the transcriptional activity of hAR. It also encodes a protein allowing the cells expressing it to resist a treatment with puromycin. The plasmid encoding hAR contains the cDNA of hAR under the control of the Cytomegalovirus (CMV) promoter. It also encodes a protein allowing the cells expressing it to resist a treatment with neomycin. The treatment of cells with increasing amounts of potentially agonistic compounds will increase the expression of the reporter gene. To detect antagonists, on the other hand, increasing doses of test compounds are tested in the presence of increasing concentrations of DHT. The expression of the reporter gene, which is constant for each dose of DHT, decreases when the concentration of the test compounds increases.

1—Tests of Functional Efficacy
1-1 Construction of Plasmids
a):—Construction of the Puromycin Resistance Plasmid 3xpbAREminicoll-Luciferase/pGL3

The first step involves introducing, into the basic pGL3 vector (Promega), the minimal promoter of the collagenase gene upstream of the gene encoding luciferase. Two oligonucleotides (coll-sense and coll-rev) were synthesised. They allow introduction of the sites of cleavage of the restriction enzymes Sad (single underscore in the sequences below) and BglII (double underscore in the sequences below) at the 5' and 3' ends respectively of the sequence between the positions −42 and +46 (bold in the sequences below) of the described promoter sequence [P Angel et al. 1987 Mol. Cell. Biol. 7:2256-2266]. After hybridisation and cloning between the SadI (position 8) and BglII— (position 37) sites of the "pGL3 basic" plasmid, the "minicoll-luciferase/pGL3" plasmid was obtained. The sequence of the oligonucleotides "coll-sense" and "coll-rev" is as follows:

```
coll-sense (SEQ ID No: 1):
5'CACTGTGTCGACGCGTGCAAGGACTCTATATATACAGAGGGAGCTTCC

TAGCTGGGATATTGGAGCAGCAAGAGGCTGGGAAGCCATCACTTACCTTG

CACTGA3' coll-rev (SEQ ID No: 2):
3'GATCTCAGTGCAAGGTAAGTGATGGCTTCCCAGCCTCTTGCTGCTCCA

ATATCCCAGCTAGGAAGCTCCCTCTGTATATATAGAGTCCTTGCACGCGT

CGACACAGTGAGCT5'
```

The second step involved multimerising 3 times the androgen receptor response element contained on the probasin (pbARE) promoter (bold in the sequences below) [F. Claessens et al. 1996 J. Biol. Chem. 271:19013-19016] and introducing it between the sites KpnI and Ecl136II- of the "minicoll-luciferase/pGL3" plasmid. Two oligonucleotides (colisense and coil-rev) were synthesised. They allow introduction of the sites of cleavage of the restriction enzymes KpnI (single underscore in the sequences below) and a blunt end (double underscore in the sequences below) at the 5' and 3' ends respectively. After hybridisation, a DNA fragment was obtained which could be cloned between the sites KpnI (position 1) and Ec113611 (position 8) of the "minicoll-luciferase/pGL3" plasmid, thus generating the "3xpbAREminicoll-luciferase/pGL3" plasmid. The "coil-sense" and "3xpbARE-rev" oligonucleotide sequences are as follows:

```
3xpbARE-sense (SEQ ID No: 3):
5'CAAAGAGCTCTAGCTTAATAGGTTCTTGGAGTACTTTACGTGCTTAAT

AGGTTCTTGGAGTACTTTACGTGCTTAATAGGTTCTTGGAGTACTTT3'

3xpbARE-rev (SEQ ID No: 4):
3'AAAGTACTCCAAGAACCTATTAAGCACGTAAAGTACTCCAAGAACCTA

TTAAGCACGTAAAGTACTCCAAGAACCTATTAAGCTAGAGCTCTTTGGTA

C5'
```

The third step involved introducing the puromycin-resistance gene into the "3xpbAREminicoll-luciferase/pGL3" plasmid. The assembly [promoter—puromycin-resistance gene—of polyadenylation sequence of SV40] (fragment 1-1396, Gene library U07648) was subcloned using PCR amplification, starting from the plasmid "pPUR" (Clontech), and using two oligonucleotides (pPUR-sense and pPUR-rev) allowing the cleavage site BamHI to be introduced. The 1,550 base pairs fragment obtained after PCR (30 cycles, 30 seconds at 94° C., 30 seconds at 55° C., 1.5 minutes at 72° C.) was digested by BamHI then cloned at the single BamHI site of the plasmid 3xpbAREminicoll-luciferase/pGL3 thus yielding the puromycin resistance plasmid 3xpbAREminicoll-luciferase/pGL3. The "coli-sense" and "coli-rev" oligonucleotide sequence are as follows:

```
pPUR-sense (SEQ ID No: 5):
5'TAAGGATCCGCTGTGGAATGTGTGTCAGTT3' pPUR-rev (SEQ ID No: 6):
3'GACGGATCCAGACATGATAAGATACATTGA5'
``` b—Construction of the "pcDNA3-hAR" Plasmid

The sequence encoding the hAR cDNA was cloned between the sites EcoRI and XbaI of the pcDNA3.1(+) vector (Invitrogen) starting from the vector psg5-hAR (provided by Professor P. Chambon, IGBMC, Illkirch, France). This plasmid contains the sequence described by Tilley W D et al. [Tilley W D et al. 1989 Proc Natl Acad Sci USA. 86:327-31; Gene library J04150].

1-2 Establishment of the Stable HALP Cell Line

For this test, HeLa cells were obtained from the American Type Culture Collection (Rockville, Md.) and cultivated in DMEM medium containing 4.5 g/l of glucose, supplemented with Glutamax and with nonessential amino-acids and with 10% of foetal calf serum (SVF; Dominique Dutscher).

On the day before transfection, a million cells were seeded in DMEM medium without phenol red, supplemented with Glutamax and with desteroided SVF (5%) in Petri dishes. The cells were transfected with 4 µg of the puromycin resistance plasmids pcDNA3-hAR and 3xpbAREminicoll-luciferase/pGL3 using the reagent "Lipofectamine plus" (Invitrogen), following the supplier's recommendations. The day after transfection, the cells were seeded to different cell densities (10,000 to 100,000 cellules per Petri dish). Two days after transfection, the transfected cells were selected in DMEM medium without phenol red, supplemented with Glutamax and with desteroided SVF (5%) containing 400 µg/mL of G418 (Invitrogen) and 150 ng/mL of puromycin (Sigma). The culture medium was renewed weekly until resistant clones appeared. The resistant clones were removed and amplified before being tested for their functional response.

The functional response test was conducted as follows: The cells were seeded (80,000 cells per well, 48 wells per plate) 24 hours before the phase of stimulation in DMEM medium containing 4.5 g/L of glucose, supplemented with Glutamax and nonessential amino-acids, and with desteroided SVF (5%). On the day of stimulation, the seeding medium was replaced by DMEM medium without phenol red, supplemented with Glutamax and with desteroided SVF (5%) containing a range of concentrations of DHT (1 pM to 1 µM). The cells were placed in contact with the compounds for 18 hours at 37° C. The medium was then removed, the cells lysed and the luciferase activity measured using the reagent "Luciferase assay system" (Promega) in accordance with the manufacturer's instructions. The luminescence produced was detected on a TopCount-type counter (Perkin-Elmer). The clone (HALP2) retained for the screening test showed a transcriptional response curve similar to that obtained after transitory transfection of the same vectors in HeLa cells.

1-3 Functional Response Test

The functional response test was conducted on 96-well plates. The HALP2 cells were seeded (30,000 cells per well) 24 hours before the phase of stimulation in DMEM medium containing 4.5 g/L of glucose, supplemented with Glutamax and nonessential amino-acids, and with desteroided SVF (5%).

On the day of stimulation, the seeding medium was replaced by DMEM medium without phenol red, supplemented with Glutamax and with desteroided SVF (5%). Stimulation involved crossing a range of concentrations of DHT (1 pM to 400 nM) with a range of concentrations of the tested compound (4 nM to 4 µM). The cells were placed in contact with the compounds for 20 hours at 37° C. The medium was then removed and the luciferase activity reading reagent was placed in contact with the cells in accordance with the manufacturer's instructions (SteadyLite, Perkin-Elmer). The luminescence produced was detected on a TopCount type counter (Perkin-Elmer).

The agonism is characterised by the $EC_{50}$ value, in other words the concentration of tested compound which induces 50% of the maximum agonistic effect observed with the tested compound. The antagonism is characterised by the $K_{Schild}$ value, in other words the concentration of the tested compound which increases the $EC_{50}$ of the DHT by a factor of 2. This concentration is determined by a conventional Schild regression.

The measured $EC_{50}$ and $K_{Schild}$ values of the compounds of general formula I according to the invention are presented in Table I.

TABLE I

| Example | $EC_{50}$ (nM) Kd | $K_{Schild}$ (nM) potency |
|---|---|---|
| 1 | 4.44 | 2.67 |
| 2 | 13.92 | 9.65 |
| 3 | 6.84 | 6.84 |
| 4 | 10.24 | 7.38 |
| 5 | 2.59 | 1.61 |
| 6 | 3.46 | 2.45 |
| 7 | 5.48 | 3.46 |
| 8 | 8 | 1.5 |
| 9 | 5.6 | 2.1 |
| 10 | 16.44 | 13.69 |
| 11 | 80 | 80 |
| 12 | 34.64 | 24.49 |
| 13 | 122.47 | 122.47 |
| 14 | 30 | 30 |
| 15 | 11.29 | 11.29 |
| 16 | 244.95 | 244.95 |
| 17 | 2000 | 2000 |
| 18 | 5656.85 | 5656.85 |
| 19 | 194.8 | 154.92 |
| 20 | 4 | 3 |
| 21 | 3.46 | 3 |
| 22 | 15 | 15 |
| 23 | 3 | 2 |
| 24 | 15 | 15 |
| 24.1 | 15 | 10 |
| 24.2 | 30 | 20 |
| 25 | 18.73 | 10.9 |
| 26 | 20 | 20 |
| 27 | 13.39 | 10.63 |
| 28 | 24.49 | 24.49 |
| 29 | 60 | 60 |
| 30 | 15 | 15 |
| 31 | 800 | 800 |
| 32 | 300 | 300 |
| 33 | 1.44 | 0.78 |
| 34 | 4.58 | 3.3 |
| 35 | 36.34 | 36.34 |
| 36 | 69.28 | 69.28 |
| 37 | 24.49 | 24.49 |
| 38 | 3.46 | 3 |
| 39 | 4 | 2 |
| 40 | 3.46 | 1.41 |
| 41 | 25.3 | 15.49 |
| 42 | 8 | 4.9 |
| 43 | 1.41 | 0.49 |
| 44 | 6 | 4 |
| 45 | 100 | 100 |
| 46 | 77.46 | 77.46 |
| 47 | 60 | 48.99 |
| 48 | 60 | 48.99 |
| 49 | 69.28 | 42.43 |
| 50 | 9.9 | 9.9 |
| 51 | 15 | 15 |
| 52 | 205.98 | 205.98 |
| 53 | 9.74 | 9.74 |
| 54 | 200 | 200 |
| 55 | 54.77 | 34.64 |
| 56 | 34.64 | 34.64 |
| 57 | 34.64 | 34.64 |
| 58 | 48.99 | 48.99 |
| 59 | 69.28 | 69.28 |
| 60 | 24.49 | 21.21 |

TABLE I-continued

| Example | $EC_{50}$ (nM) Kd | $K_{Schild}$ (nM) potency |
|---|---|---|
| 61 | 34.64 | 34.64 |
| 62 | 34.64 | 34.64 |
| 63 | 69.28 | 69.28 |
| 64 | 26.21 | 26.21 |
| 65 | 7.11 | 5.43 |
| 66 | 24.49 | 21.21 |
| 67 | 48.99 | 48.99 |
| 68 | 24.49 | 24.49 |
| 69 | 42.43 | 42.43 |
| 70 | 20 | 20 |
| 71 | 300 | 300 |
| 72 | 42.43 | 42.43 |
| 73 | 13.77 | 13.77 |
| 74 | 21.21 | 17.32 |
| 75 | 600 | 600 |
| 76 | 200 | 200 |
| 77 | 122.47 | 94.87 |
| 78 | 94.87 | 77.46 |
| 79 | 69.28 | 69.28 |
| 80 | 80 | 80 |
| 81 | 16.38 | 16.38 |
| 82 | 42.43 | 30 |
| 83 | 565.69 | 565.69 |
| 84 | 24.49 | 17.32 |
| 85 | 300 | 300 |
| 86 | 48.99 | 48.99 |
| 87 | 77.46 | 77.46 |
| 88 | 34.64 | 34.64 |
| 89 | 200 | 200 |
| 90 | 565.69 | 282.84 |
| 91 | 94.87 | 94.87 |
| 92 | 1500 | 1500 |
| 93 | 34.64 | 30 |
| 94 | 300 | 300 |
| 95 | 632.46 | 632.46 |
| 96 | 692.82 | 692.82 |
| 97 | 28.28 | 28.28 |
| 98 | 94.87 | 94.87 |
| 99 | 69.28 | 69.28 |
| 100 | 77.46 | 77.46 |
| 101 | 244.95 | 244.95 |
| 102 | 48.99 | 48.99 |
| 103 | 48.99 | 48.99 |
| 104 | 200 | 200 |
| 105 | 60 | 60 |
| 106 | 424.26 | 424.26 |
| 107 | 42.43 | 42.43 |
| 108 | 244.95 | 244.95 |
| 109 | 60 | 60 |
| 110 | 200 | 200 |
| 111 | 141.42 | 141.42 |
| 112 | 244.95 | 244.95 |
| 113 | 109.54 | 109.54 |
| 114 | 1095.45 | 1095.45 |
| 115 | 141.42 | 141.42 |
| 116 | 2000 | 2000 |
| 117 | 77.46 | 77.46 |
| 118 | 244.95 | 244.95 |
| 119 | 282.84 | 282.84 |
| 120 | 424.26 | 424.26 |
| 121 | 24.49 | 17.32 |
| 122 | 300 | 244.95 |
| 123 | 42.43 | 30 |
| 124 | 89.44 | 89.44 |
| 125 | 30 | 30 |
| 126 | 212.13 | 212.13 |
| 127 | 244.95 | 212.13 |
| 128 | 244.95 | 244.95 |
| 129 | 40.54 | 34.64 |
| 130 | 21.21 | 21.21 |
| 131 | 600 | 600 |
| 132 | 69.28 | 69.28 |
| 133 | 600 | 600 |
| 134 | 122.47 | 122.47 |
| 135 | 600 | 600 |
| 136 | 600 | 600 |
| 137 | 54.77 | 24.49 |

TABLE I-continued

| Example | EC$_{50}$ (nM) Kd | K$_{Schild}$ (nM) potency |
|---|---|---|
| 138 | 600 | 600 |
| 139 | 44.72 | 28.28 |
| 140 | 489.9 | 489.9 |
| 141 | 21.21 | 17.32 |
| 142 | 141.42 | 141.42 |
| 143 | 173.21 | 173.21 |
| 144 | 126.49 | 109.54 |
| 145 | 60 | 60 |
| 146 | 30 | 30 |
| 147 | 300 | 300 |
| 149 | 60 | 60 |
| 150 | 60 | 60 |
| 151 | 42.43 | 42.43 |
| 152 | 4 | 4 |
| 153 | 5.66 | 5.66 |
| 154.1 | 15 | 15 |
| 155 | 1.86 | 0.87 |
| 156 | 200 | 200 |
| 156.1 | 10 | 6 |
| 156.2 | 3 | 1.5 |
| 156.3 | 30 | 30 |
| 156.4 | 3 | 0.8 |
| 158 | 30 | 30 |
| 159 | 40 | 40 |
| 160 | 60 | 60 |
| 161 | 60 | 60 |
| 162 | 40 | 40 |
| 163 | 80 | 80 |
| 164 | 1000 | 1000 |
| 165 | 60 | 60 |
| 166 | 300 | 300 |
| 166.1 | 400 | 400 |
| 167 | 54.77 | 54.77 |
| 168 | 30 | 30 |
| 169 | 10 | 10 |
| 170 | 100 | 100 |
| 171 | 600 | 600 |
| 172 | 15 | 8 |
| 173 | 4 | 3 |
| 174 | 8.94 | 6.93 |
| 175 | 1.38 | 0.37 |
| 176 | 2.88 | 1.34 |
| 177 | 1.64 | 0.72 |
| 177.1 | 600 | 310 |
| 177.2 | 80 | 40.4 |
| 177.3 | 20 | 15 |
| 178 | 10 | 10 |
| 179 | 15 | 15 |
| 180 | 8 | 8 |
| 181 | 6 | 6 |
| 182 | 15 | 15 |
| 182.1 | 20 | 15 |
| 183 | 4 | 2 |
| 184 | 4.9 | 2.8 |
| 190 | 1.38 | 0.37 |
| 191 | 2.88 | 1.34 |
| 192 | 2 | 1.26 |
| 220 | 4 | 3 |
| 221 | 5.66 | 5.66 |
| 222 | 4.9 | 4 |
| 222.1 | 4 | 4 |
| 222.2 | 15 | 15 |
| 222.3 | 200 | 200 |
| 223 | 12.25 | 12.25 |
| 223.1 | 8 | 4 |
| 224 | 3.4 | 2 |
| 225 | 3.46 | 2.83 |
| 226 | 4 | 2.45 |
| 227 | 4 | 3.46 |
| 228 | 20 | 20 |
| 228.1 | 150 | 150 |
| 230 | 60 | 60 |
| 231 | 60 | 60 |
| 233 | 4 | 2.45 |
| 234 | 15 | 15 |
| 235 | 8 | 8 |
| 236 | 15 | 15 |
| 237 | 8 | 8 |
| 238 | 15 | 15 |
| 239 | 10 | 10 |
| 240 | 3.46 | 2.45 |
| 241 | 8 | 6 |
| 242 | 12.25 | 12.25 |
| 243 | 4.9 | 4.56 |
| 243.1 | 80 | 80 |
| 243.2 | 150 | 150 |
| 340 | 20 | 20 |
| 341 | 30 | 30 |
| 342 | 40 | 40 |
| 343 | 60 | 60 |

2—Characterisation in Animal Models 2-1 Adapted Model of Hershberger's Test

The in vivo activity of imidazolidine derivatives of general formula (I) was demonstrated in an adapted model of the Hershberger test in the following manner:

The selective modulating activity of the androgen receptor was tested in a model of castrated immature young rats. This model, which is widely recognised for evaluating the anabolic effects of androgen compounds on the muscles and on the genitalia, has been described by Hershberger et al. 1953 Proc. Soc. Expt. Biol. Med. 83:175.

The method is based on the measurement of the well-known effects of androgens on the growth of the muscles and the accessory male sex organs in animals, and also in men. The consequences of castration appear in the form of a rapid involution and atrophy of the prostate and the seminal vesicles and of the anus-lifting muscle (levator ani). This effect may be completely compensated by an exogeneous administration of androgen, in particular of testosterone. The model is thus used to determine the capacity of the tested molecules to maintain the weight of the accessory sex and muscle organs in immature castrated rats, and therefore their androgenic efficacy.

Immature young Sprague Dawley rats (4 to 5 weeks old) weighing approximately 140-160 g (Charles River, Les Oncins, FRANCE) were distributed randomly in various groups and were kept in an environment at 22±2° C. with an alternating day/night cycle of 12 hours and ad libitum access to food and drink.

On day 0, that is, seven days before commencement of the first treatment, the rats were weighed individually then anaesthetised with an intraperitoneal dose of Ketamine/xylazine (85/15 mg/kg, approximately 2 ml/kg). Each animal was then placed on a sterile field and the abdomen and the scrotum were disinfected with Betadine and 70% alcohol. In the case of the orchidectomised control animals (ORX), the testicles were removed via an incision in the middle of the scrotum. A sterile suture was then made to ligature the supra-testicular portion of the tissue prior to surgical section of each testicle. The groups of animals to be treated by the tested compounds were operated on in an identical manner. In the case of the intact control animals (SHAM), the testicles were similarly extracted and reintroduced delicately to their original location. The site of surgical intervention was then sutured using sterile suture thread, and the site was disinfected again by application of Betadine. Each animal was then kept under a sterile pad until it awoke, before being returned to its cage. The animals were kept in an environment at 22±2° C. with an alternating day/night cycle of 12 hours and ad libitum access to food and drink. The animals were treated with the molecules to be tested from post-surgery day 7 and until day 10 preceding sacrifice (day 11).

The rats were split into groups and treated daily from day 7 to day 10 under the conditions defined below:
1. SHAM control group: Vehicle (0.5% aqueous methyl cellulose) administered per os.
2. ORX control group: Vehicle (0.5% aqueous methyl cellulose) administered per os.
3. Treated ORX group: The tested compounds were administered individually per os in suspension in the vehicle described above, in a dose of 30 mg/kg.

After treatment for 4 successive days, the animals were decapitated using a guillotine. The levator ani and the ventral prostate were removed and weighed individually. For comparing inter-experimental data, the weight of each organ was standardised and expressed in milligrammes per 100 g of the weight of the animal (W). For each organ, the average of the standardised weights of the ORX control group was fixed by definition at 0% and the average of the standardised weights of the SHAM control group was fixed by definition at 100%. The efficacy of each product was expressed as a percentage and calculated using the following formula:

$$(W_{treated} - W_{ORX})/(W_{SHAM} - W_{ORX}) \times 100$$

A subsequent ANOVA test was used for statistical analysis to identify the differences between groups.

In the above-defined dose, the products of Examples 1, 3 to 6, 8, 9, 155, 156-2, 175 to 177, 220, 222, 222-1, 245, and 319 were shown to provide anabolic protection efficacy with regard to levator ani of between 50 and 140%. The androgenic efficacy with regard to the prostate is between 5 and 70%.

2-2 Model of Osteoporosis in Male Mice

C57/B16J male mice aged 12 weeks and weighing approximately 20-25 g (Charles River, Les Oncins, FRANCE) were operated on as described above with regard to the rats. Castration mimicked the bone loss caused by androgen deficit. The aim of the study is to evaluate the capacity of the compounds to preserve and/or increase the bone mass. This is evaluated by measuring the bone mineral density (BMD). This model has previously been documented by Sims et al. 2003 J. Clin. Invest. 111(9):1319-27.

The animals were separated randomly into various groups and were kept in an environment at 22±2° C. with an alternating day/night cycle of 12 hours and ad libitum access to food and drink.

The tested compounds were administered from post-surgery day 1 and until day 28 preceding sacrifice (day 29). The mice were treated daily under the conditions defined below:
1. SHAM control group: Vehicle (10/90 ethanol/corn oil mixture) administered subcutaneously.
2. ORX control group: Vehicle (10/90 ethanol/corn oil mixture) administered subcutaneously.
3. Treated ORX group: The tested compounds were administered individually subcutaneously in the vehicle described above, in a dose of 30 mg/kg.

During necropsy, the mice were first weighed then decapitated. The two hindlimbs were then carefully disarticulated at the femoral neck. The right hindlimb was frozen at −20° C. Densitometric quantitative analysis was performed on the trabecular portion of the tibia proximal metaphysis using a tomo densitometer (Stratec SA+, Hologic, Norland).

The average of the trabecular BMD of the mice in the ORX control group was defined as 0%. The average of the trabecular BMD of the mice in the SHAM control group was defined as 100%. The efficacy of each product as a percentage was calculated using the formula:

$$(BMD_{treated} - BMD_{ORX})/(BMD_{SHAM} - BMD_{ORX}) \times 100$$

A subsequent ANOVA test was used for statistical analysis to identify the differences between groups.

The products of Examples 1, 3 to 8, 155, 220, 245 and 319 show efficacy in protecting mineral bone density of between 40 and 130%.

The following non-limiting Examples illustrate the present invention.

EXAMPLES

Abbreviations used:

| | |
|---|---|
| AIBN: azoisobutyronitrile; | Mp: melting point; |
| DMF: N,N-dimethylformamide; | Yd: yield; |
| DMSO: dimethylsulphoxide; | Fr: frontal ratio |
| MeOD: deuterated methanol; | AT: ambient temperature; |
| NBS: N-bromosuccinimide; | $H_{Ar}$: aromatic hydrogen |
| THF: tetrahydrofuran; | Rt: retention time |

Chromatography: Thin layer chromatography (TLC) was conducted on glass plates coated with silica gel $F_{254}$ (0.25 mm, Merck). Preparative chromatography was conducted over a column of Merck silica gel having a grain size of 0.04-0.063 mm.

Nuclear magnetic resonance spectra (NMR): These were recorded at 300 or 400 MHz, in solution in the solvent mentioned. The chemical shifts are expressed as a value δ relative to the shift of the tetramethylsilane used as a reference. AB: AB system; d: doublet; l: large; m: multiplet; q: quadruplet; s: singlet; t: triplet.

Mass spectra (LC/MS): These were conducted on a spectrometer coupled to a Waters liquid chromatography apparatus (electrospray ionisation). The column used is a 2.1×50 mm Xterra RP18 (3.5 μm). Two gradient conditions are employed, using as solvents: A=water+0.01% of formic acid and B=$CH_3CN$+0.01% of formic acid.

Gradient 1: from 95/5 A/B at time 0 to 100% of B after 4 min, then 100% of B for 3 min.

Gradient 2: from 60/40 A/B at time 0 to 100% of B after 4 min, then 100% of B for 3 min.

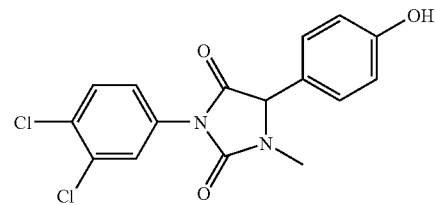

Example 1

1-(3,4-dichlorophenyl)-4-(4-hydroxyphenyl)-3-methylimidazolidine-2,5-dione 190 mg of 3,4-dichlorophenyl isocyanate are added to a solution of 200 mg of methyl 2-(4-hydroxyphenyl)-2-methylaminoacetate in 5 mL of anhydrous THF in a 50 mL flask equipped with a magnetic stirrer, under nitrogen. After 1 night at 50° C. the product is concentrated then crystallised in isopropyl ether. The solid is filtered and washed with isopropyl ether to yield 315 mg of a white powder (Yd=90%); Mp=200° C.

TLC: Fr=0.41 (50/50 heptane/ethyl acetate).

1H-NMR (CDCl3): δ 2.9 (s, 3H, NMe); 4.9 (s, 1H, NCHCO); 6.92 (d, 2 HAr); 7.2 (d, 2 HAr); 7.4 (d, 1 HAr); 7.55 (d, 1 HAr); 7.68 (s, 1 HAr).

LC/MS Gradient 1: Rt: 4.63 min; 349/351– (M–H)–

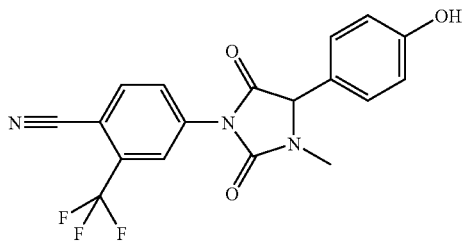

Example 2

4-[2,5-dioxo-4-(4-hydroxyphenyl)-3-methyl-imidazolidin-1-yl]-2-trifluoromethylbenzonitrile 1.2 ml of a 2 M solution of 4-cyano-3-trifluoromethylphenyl in THF are added to a solution of 390 mg of methyl 2-(4-hydroxyphenyl)-2-methylaminoacetate in 8 mL of anhydrous THF in a 50 mL flask equipped with a magnetic stirrer, under nitrogen. After 15 min at AT, the crude reaction product is concentrated to yield 1.07 g of orange oil. This oil is purified over a silica column while eluting with the 60/40 mixture of heptane/ethyl acetate to yield an amorphous white solid. The product is crystallised in isopropyl ether. The solid is filtered and washed with isopropyl ether to yield 514 mg of a white powder (Yd=68%); Mp=157.4° C.

TLC: Fr=0.51 (30/70 heptane/ethyl acetate).

1H-NMR (CDCl3): δ 3.0 (s, 3H, NMe); 4.98 (s, 1H, NCHCO); 5.25 (sl, 1H, OH,); 6.91 (d, 2 HAr); 7.20 (d, 2 HAr); 7.93 (d, 1 HAr); 8.01 (d, 1 HAr); 8.15 (s, 1 HAr).

LC/MS Gradient 1: Rt: 4.81 min; 374– (M–H)–

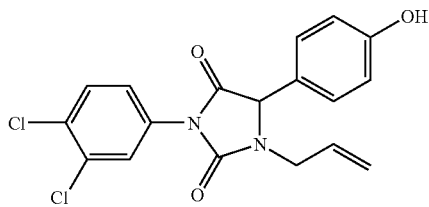

Example 3

1-(3,4-dichlorophenyl)-4-(4-hydroxyphenyl)-3-(2-propenyl)imidazolidine-2,5-dione 1.1 equivalent of 3,4-dichlorophenyl isocyanate is added to a solution of 3.5 g of methyl 2-(4-hydroxyphenyl)-2-(2-propenyl)aminoacetate in 50 mL of anhydrous THF in a 50 mL flask equipped with a magnetic stirrer, under nitrogen. After heating under reflux for 4 hours, the product is concentrated then crystallised in isopropyl ether. The solid is filtered and washed with isopropyl ether to yield 3.2 g of white powder (Yd=54%).

1H-NMR (CDCl3): δ 3.4 and 4.5 (2dd, 2H, NCH2); 5.0 (s, 1H, NCHCO); 5.12 and 5.28 (2d, 2H, CH2=CH); 5.75 (m, 1H, CH2=CH); 6.8 (d, 2 HAr); 7.1 (d, 2 HAr); 7.4 (dd, 1 HAr); 7.55 (d, 1 HAr); 7.7 (s, 1 HAr).

LC/MS Gradient 1: Rt: 4.70 min; 375/377– (M–H)–

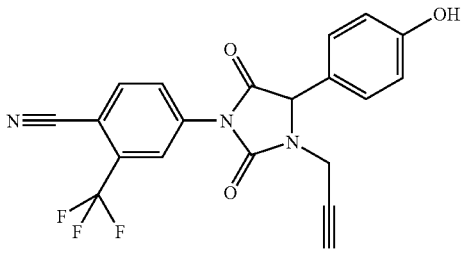

Example 4

4-[2,5-dioxo-4-(4-hydroxyphenyl)-3-(2-propynyl)imidazolidin-1-yl]-2-trifluoromethylbenzonitrile 3.42 g of 4-cyano-3-trifluoromethylphenyl isocyanate and 75 mL of anhydrous THF are introduced into a flask equipped with a magnetic stirrer, under nitrogen, then 3.47 g of methyl 2-(4-hydroxyphenyl)-2-(2-propynyl)aminoacetate in 5 mL of anhydrous THF are added in one batch. After 15 min at AT, the mixture is concentrated to yield a brown paste (8.65 g). The crude product is purified over a silica column with a heptane/ethyl acetate gradient of 80/20 then 70/30 then 60/40. 5.74 g of an amorphous solid with pale yellow reflections is obtained. After crystallisation in isopropyl ether then recrystallisation in an ethyl acetate/heptane mixture, white crystals are obtained and are dried under vacuum at 45° C. (4.40 g; Yd=70%); Mp=195° C.

TLC: Fr=0.34 (50/50 heptane/ethyl acetate).

1H-NMR (CDCl3): δ 2.84 (s, 1H, CH); 3.74 and 4.66 (2d, 2H, NCH2); 5.37 (s, 1H, NCHCO); 6.93 (d, 2 HAr); 7.29 (d, 2 HAr); 8.14 (m, 2 HAr); 8.25 (s, 1 HAr).

LC/MS Gradient 1: Rt: 5.11 min; 398– (M–H)–

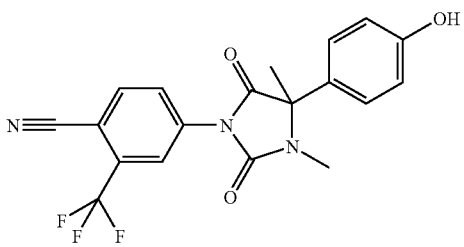

Example 5

4-[3,4-dimethyl-2,5-dioxo-4-(4-hydroxyphenyl)imidazolidin-1-yl]-2-trifluoromethylbenzonitrile 470 μL of a 2 M solution of 4-cyano-3-trifluoromethylphenyl isocyanate in THF are introduced into a flask under nitrogen at ambient temperature. 196 mg of methyl 2-(4-hydroxyphenyl)-2-methylaminopropionate and 4 mL of THF are added. The mixture is stirred at ambient temperature. After 5 min, the solution becomes cloudy. After 2 hours at ambient temperature, some amino ester, which is visible in TLC remains. 235 μL of a 2 M solution of isocyanate are added, then a further 235 μL are added after 3 hours and the mixture is stirred for a further 1 hour at ambient temperature, then for 1 hour under reflux. The insoluble matter is filtered and rinsed with THF, and the filtrate is concentrated to yield 419 mg of an amorphous foam with mauve reflections. The residue is purified over a silica column with 70/30 then 60/40 heptane/ethyl acetate. 350 mg of product (amorphous white solid) are obtained (Yd=96%); Mp=136° C.

TLC: Fr=0.55 (40/60 heptane/ethyl acetate).

1H-NMR (CDCl3): δ 1.95 (s, 3H, Me); 2.95 (s, 3H, NMe); 6.9 (d, 2 HAr); 7.2 (d, 2 HAr); 7.9 (d, 1 HAr); 8.0 (dd, 1 HAr); 8.15 (s, 1 HAr).

LC/MS Gradient 1: Rt: 4.66 min; 388– (M–H)–; 777– (2M–H)–

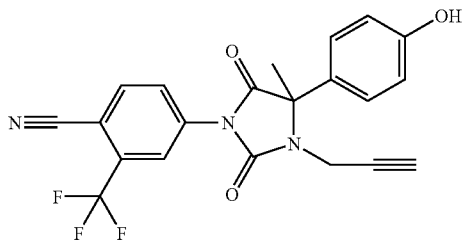

Example 6

4-[2,5-dioxo-4-(4-hydroxyphenyl)-4-methyl-3-(2-propynyl)imidazolidin-1-yl]-2-trifluoromethylbenzonitrile 1.07 mL of a 2 M solution of 4-cyano-3-trifluoromethylphenyl isocyanate in THF is introduced into a flask at ambient temperature. 500 mg of methyl 2-(4-hydroxyphenyl)-2-(2-propynyl)aminopropionate and 20 mL of THF are added. After 1 night at ambient temperature, the residue is concentrated and purified over a silica column, while eluting with 97/3 then 90/10 dichloromethane/ethyl acetate. 410 mg of product (white solid; Yd=89%) are obtained.

TLC: Fr=0.4 (50/50 heptane/ethyl acetate).

1H-NMR (MeOD): δ 2.05 (s, 3H, Me); 2.73 (s, 1H, HC); 3.85 and 4.45 (2d, J=20 Hz, 2H, NCH2); 6.9 and 7.35 (2d, 4 HAr); 8.15 (2d, 2 HAr); 8.25 (s, 1 HAr).

LC/MS Gradient 1: Rt: 4.69 min; 412– (M–H)–

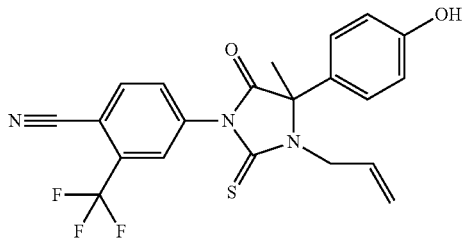

Example 7

4-[4-(4-hydroxyphenyl)-4-methyl-5-oxo-3-(2-propenyl)-2-thioxoimidazolidin-1-yl]-2-trifluoromethylbenzonitrile 300 mg of 4-cyano-3-trifluoromethylphenyl isothiocyanate, 40 mL of anhydrous THF, 346 mg of methyl 2-(4-hydroxyphenyl)-2-(2-propenyl)aminopropionate and 0.2 mL of triethylamine are introduced into a flask at ambient temperature. After 18 hours at ambient temperature, the residue is concentrated and purified over a silica column while eluting with 60/40 heptane/ethyl acetate. The residue is crystallised in cyclohexane with a few drops of isopropyl ether. 450 mg of product are obtained (white solid; Yd=70%).

TLC: Fr=0.3 (50/50 heptane/ethyl acetate).

1H-NMR (MeOD): δ 1.96 (s, 3H, Me); 3.89 and 4.61 (2dd, J=6.7 and 20 Hz, 2H, NCH2); 5.13 (d, J=10 Hz, 1H, CH=CH2); 5.2 (d, J=15 Hz, 1H, CH=CH2); 5.9 (m, 1H, CH=CH2); 6.86 (d, 2 HAr); 7.19 (d, 2 HAr); 7.9 (d, 1 HAr); 8.08 (s, 1 HAr); 8.15 (d, 1 HAr).

LC/MS Gradient 1: Rt: 3.84 min; 430– (M–H)–

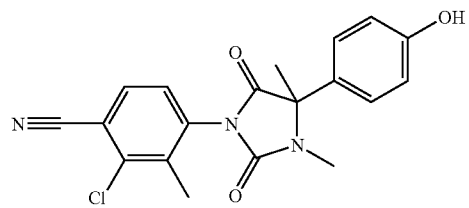

Example 8

2-chloro-4-[3,4-dimethyl-2,5-dioxo-4-(4-hydroxyphenyl)imidazolidin-1-yl]-3-methylbenzonitrile 1.15 g of 3-chloro-4-cyano-2-methylphenyl isocyanate, 25 mL of THF and 1.25 g of methyl 2-(4-hydroxyphenyl)-2-methylaminopropionate are introduced into a flask at ambient temperature. The mixture is stirred at ambient temperature for 1 night and concentrated, and the residue (2.81 g) is purified over a silica column while eluting with 60/40 heptane/ethyl acetate. 1.66 g of amorphous product is obtained and is crystallised in isopropyl ether then triturated in dichloromethane. After filtration and drying under vacuum, the product is obtained in the form of white crystals (Yd=45%); Mp=231° C.

TLC: Fr=0.28 (50/50 heptane/ethyl acetate)

1H-NMR (DMSO D6): δ 1.97 (s, 3H, Me); 2.12 and 2.25 (2s, 3H, PhMe); 2.72 and 2.79 (2s, 3H, NMe); 6.83 (m, 2 HAr); 7.25 (2d, 2 HAr); 7.59 and 7.65 (2d, 1 HAr); 8.0 (t, 1 HAr).

LC/MS Gradient 1: Rt: 1.86 min; 366/367– (M–H)–

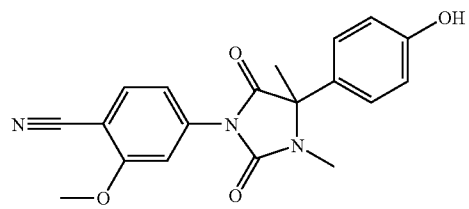

Example 9

4-[3,4-dimethyl-2,5-dioxo-4-(4-hydroxyphenyl)imidazolidin-1-yl]-2-methoxybenzonitrile 611 mg of 4-cyano-3-methoxyphenyl isocyanate, 25 mL of THF then 704 mg of methyl 2-(4-hydroxyphenyl)-2-methylaminopropionate are introduced into a flask at ambient temperature. The mixture is stirred for 1 night and concentrated, and the residue is purified over a silica column with 70/30, 60/40 then 50/50/heptane/ethyl acetate. 822 mg of white solid (Yd=45%) are obtained.

TLC: Fr=0.45 (50/50 heptane/ethyl acetate).

1H-NMR (CDCl3): δ 1.92 (s, 3H, Me); 2.93 (s, 3H, NMe); 3.94 (s, 3H, OMe); 6.90 (d, 2 HAr); 7.20 to 7.29 (m, 4 HAr); 7.62 (d, 1 HAr).

LC/MS Gradient 1: Rt: 3.42 min; 350– (M–H)–

Examples 10 to 16

Using a procedure as exemplified in Example 4, and using the appropriate isocyanate II and amino ester III, the following products are prepared:

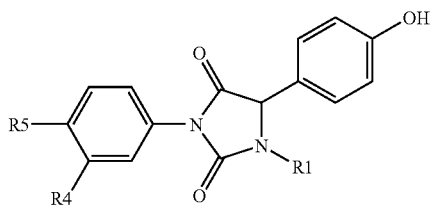

Example 10

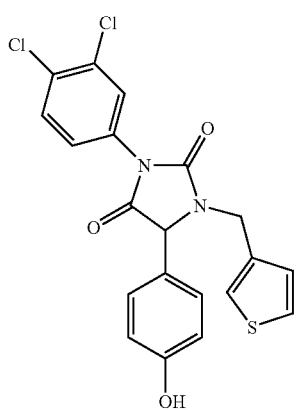

1-(3,4-dichlorophenyl)-4-(4-hydroxyphenyl)-3-[(thiophen-3-yl)methyl]imidazolidine-2,5-dione 1H-NMR (DMSO D6): δ 4.0 and 4.75 (2d, 2H, NCH2); 5.1 (s, 1H, NCHCO); 6.8 (d, 2 HAr); 6.98 (d, 1 HAr); 7.2 (d, 2 HAr); 7.32 (sl, 1H thiophene); 7.5-7.8 (m, 2 HAr, 1H thiophene); 7.85 (d, 1 HAr).

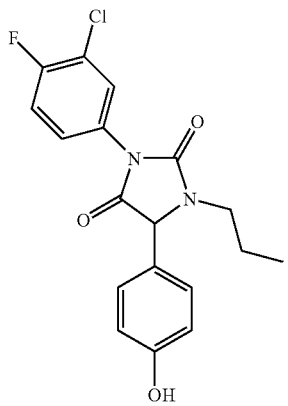

Example 11

1-(3-chloro-4-fluorophenyl)-4-(4-hydroxyphenyl)-3-propylimidazolidine-2,5-dione

1H-NMR (CDCl3): δ 0.9 (t, 3H, Me); 1.5-1.65 (m, 2H, CH2); 2.93 and 3.70 (2m, 2H, NCH2); 5.0 (s, 1H, NCHCO); 6.8 (d, 2 HAr); 7.1 (d, 2 HAr); 7.25 (m, 1HAr); 7.37 (m, 1 HAr); 7.6 (dd, 1 HAr).

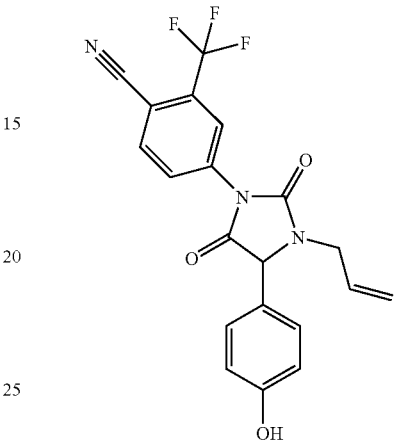

Example 12

4-[2,5-dioxo-4-(4-hydroxyphenyl)-3-(2-propenyl)imidazolidin-1-yl]-2-trifluoromethyl-benzonitrile 1H-NMR (CDCl3): δ 3.4 and 4.55 (2dd, 2H, NCH2); 5.05 (s, 1H, NCHCO); 5.18 and 5.3 (2d, 2H, CH2=CH); 5.8 (m, 1H, CH2=CH); 6.9 (d, 2 HAr); 7.15 (d, 2 HAr); 7.92 (d, 1 HAr); 8.1 (d, 1 HAr); 8.18 (s, 1 HAr).

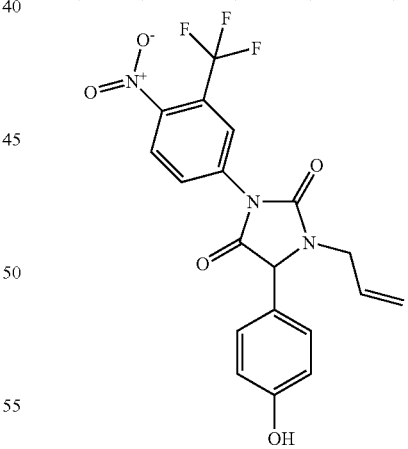

Example 13

1-(4-nitro-3-trifluoromethylphenyl)-4-(4-hydroxyphenyl)-3-(2-propenyl)imidazolidine-2,5-dione 1H-NMR (CDCl3): δ 3.4 and 4.50 (2m, 2H, NCH2); 5.15 (s, 1H, NCHCO); 5.1 (d, 1H, CH2=CH); 5.3 (t, 1H, C H2=CH); 5.77 (m, 1H, CH2=CH); 6.8 (d, 2 HAr); 7.15 (d, 2 HAr); 7.65 (m, 1 HAr); 8.60 (m, 2 HAr).

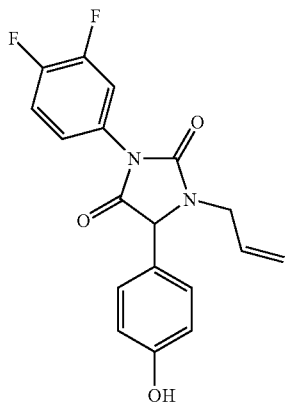

Example 14

1-(3,4-difluorophenyl)-4-(4-hydroxyphenyl)-3-(2-propenyl)imidazolidine-2,5-dione 1H-NMR (CDCl3): δ 3.4 and 4.5 (2dd, 2H, NCH2); 5.0 (s, 1H, NCHCO); 5.12 and 5.3 (2d, 2H, CH2=CH); 5.75 (m, 1H, CH2=CH); 6.8 (d, 2 HAr); 7.1 (d, 2 HAr); 7.25 (m, 2 HAr); 7.43 (m, 1 HAr).

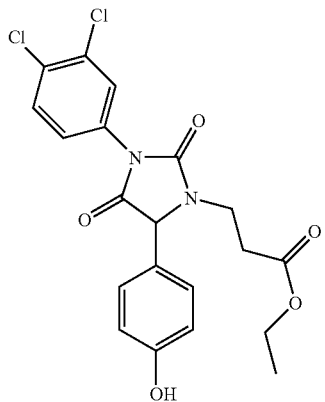

Example 15

Ethyl 3-[1-(3,4-dichlorophenyl)-4-(4-hydroxyphenyl)-2,5-dioxoimidazolidin-3-yl]propionate 1H-NMR (CDCl3): δ 1.3 (t, 3H, CH3); 2.55 and 2.75 (2m, 2H, CH2N); 3.30 and 3.90 (2m, 2H, CH2CO); 4.15 (q, 2H, OCH2); 5.15 (s, 1H, NCHCO); 6.8 (d, 2 HAr); 7.15 (d, 2 HAr); 7.4 (dd, 1 HAr); 7.52 (d, 1 HAr); 7.68 (d, 1 HAr).

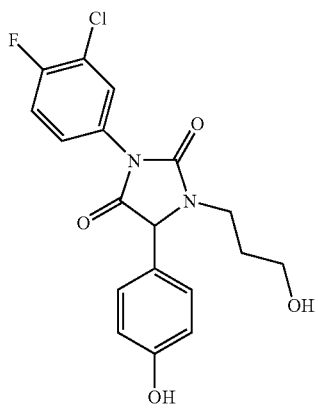

Example 16

1-(3-chloro-4-fluorophenyl)-3-(4-hydroxybutyl)-4-(4-hydroxyphenyl)imidazolidine-2,5-dione 1H-NMR (DMSO D6): δ 1.6 and 1.7 (2m, 4H, 2 CH2); 2.9 and 3.6 (2m, 2H, NCH2); 3.65 (t, 2H, CH2O); 5.2 (s, 1H, NCHCO); 6.8 (d, 2 HAr); 7.25 (d, 2 HAr); 7.5 (m, 1 HAr); 7 6 (t, 1 HAr); 7.75 (d, 1 HAr).

Examples 17 to 19

As for Example 4, using the same mode of operation with methyl 2-(4-hydroxyphenyl)-2-[(thiophen-3-yl)methylamino]acetate and the appropriate isothiocyanate II, the following products are prepared:

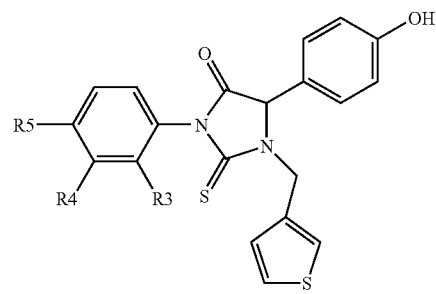

Example 17

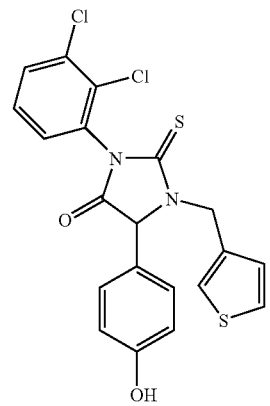

1-(2,3-dichlorophenyl)-4-(4-hydroxyphenyl)-3-[(thiophen-3-yl)methyl]-2-thioxo-imidazolidin-5-one LC/MS Gradient 1: Rt: 5.22 min; 447– (M–H)–; 897– (2M+H)–

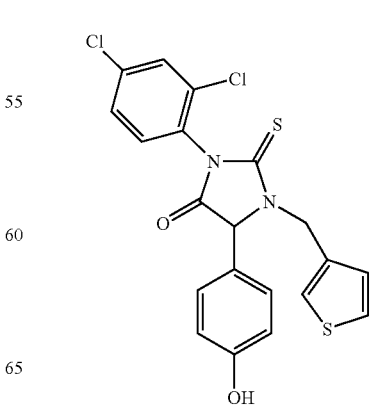

Example 18

1-(2,4-dichlorophenyl)-4-(4-hydroxyphenyl)-3-[(thiophen-3-yl)methyl]-2-thioxo-imidazolidin-5-one LC/MS Gradient 1: Rt: 5.38 min; 447– (M–H)–; 897– (2M+H)–

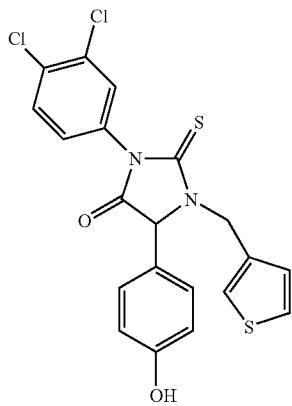

Example 19

1-(3,4-dichlorophenyl)-4-(4-hydroxyphenyl)-3-[(thiophen-3-yl)methyl]-2-thioxo-imidazolidin-5-one LC/MS Gradient 1: Rt: 5.48 min; 447– (M–H)–; 897– (2M+H)–

Examples 20 to 24

As for Example 5, using the same mode of operation with the appropriate isocyanate II and amino ester III, the following products are prepared:

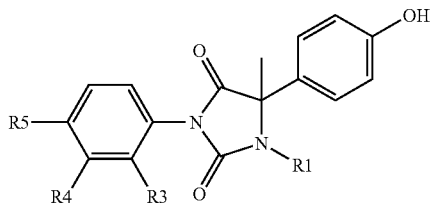

Example 20

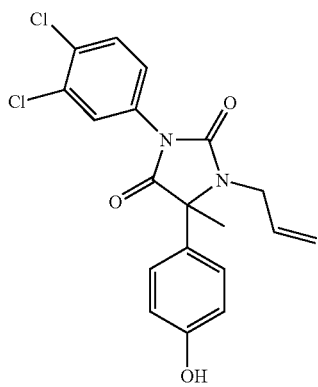

1-(3,4-dichlorophenyl)-4-(4-hydroxyphenyl)-4-methyl-3-(2-propenyl)imidazolidine-2,5-dione 2.1 g of product are obtained from 5 g of methyl 2-(4-hydroxyphenyl)-2-(2-propenyl)aminopropionate.

1H-NMR (DMSO D6): δ 1.8 (s, 3H, Me); 3.55 and 4.02 (split AB, J=6 and 17 Hz, 2H, NCH2); 5.02 (d, 1H, CH═CH2); 5.18 (d, 1H, CH═CH2); 5.65-5.75 (m, 1H, CH═CH2); 6.7 (d, 2 HAr); 7.2 (d, 2 HAr); 7.5 (dd, 1 HAr); 7.79 (d, 1 HAr); 7.85 (d, 1 HAr).

LC/MS Gradient 1: Rt: 5.47 min; 389/391– (M–H)–

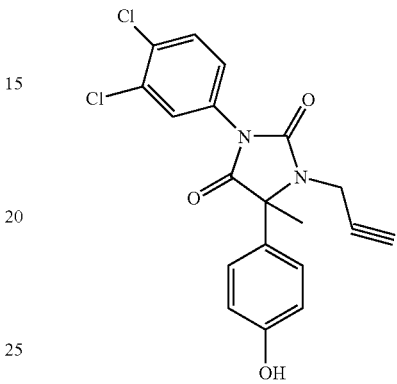

Example 21

1-(3,4-dichlorophenyl)-4-(4-hydroxyphenyl)-4-methyl-3-(2-propynyl)imidazolidine-2,5-dione 1.6 g of product is obtained from 5 g of methyl 2-(4-hydroxyphenyl)-2-(2-propynyl)aminopropionate.

1H-NMR (CDCl3): δ 1.95 (s, 3H, Me); 2.52 (very fine m, 1H, CH); 3.65 and 3.72 (2d, 2H, NCH2); 6.85 (d, 2 HAr); 7.2 (d, 2 HAr); 7.32 (s, 1 HAr); 7.5 (d, 1 HAr); 7.61 (d, 1 HAr).

LC/MS Gradient 1: Rt: 5.38 min; 387/389– (M–H)–

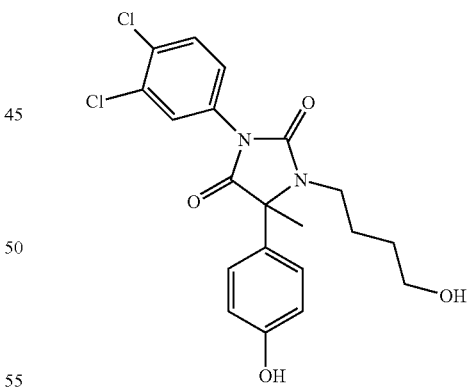

Example 22

1-(3,4-dichlorophenyl)-3-(4-hydroxybutyl)-4-(4-hydroxyphenyl)-4-methylimidazolidine-2,5-dione 1.28 g of product is obtained from 5 g of methyl 2-(4-hydroxybutyl)amino-2-(4-hydroxyphenyl)propionate.

1H-NMR (CDCl3): δ 1.5-1.8 (m, 4H, 2 CH2); 1.9 (s, 3H, Me); 3.05 and 3.48 (2m, 2H, NCH2); 3.65 (t, 2H, CH2O); 6.8

(d, 2 HAr); 7.15 (d, 2 HAr); 7.4 (dd, 1 HAr); 7.02 (d, 1 HAr); 7.68 (d, 1 HAr).

LC/MS Gradient 1: Rt: 4.3 min; 423/425+ (MH)+

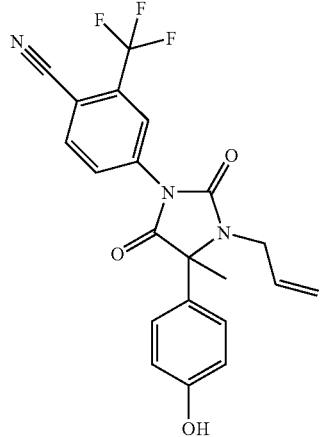

Example 23

4-[2,5-dioxo-4-(4-hydroxyphenyl)-4-methyl-3-(2-propenyl)imidazolidin-1-yl]-2-trifluoromethylbenzonitrile 0.53 g of product is obtained from 0.41 g of methyl 2-(4-hydroxyphenyl)-2-(2-propenyl)aminopropionate (Yd=74%).

1H-NMR (MeOD): δ 2.02 (s, 3H, Me); 3.65 and 4.19 (2 dd, J=6.66 and 20 Hz, 2H, NCH2); 5.09 (d, 1H, CH=CH2); 5.13 (d, 1H, CH=CH2); 5.86 (m, 1H, CH=CH2); 6.89 (d, 2 HAr); 7.28 (d, 2 HAr); 8.11 (m, 2 HAr); 8.35 (s, 1 HAr).

LC/MS Gradient 1: Rt: 3.77 min; 414– (M–H)–; 829– (2M–H)–

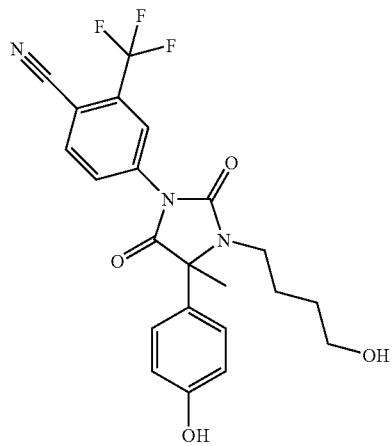

Example 24

4-[2,5-dioxo-3-(4-hydroxybutyl)-4-(4-hydroxyphenyl)-4-methylimidazolidin-1-yl]-2-trifluoromethylbenzonitrile 0.34 g of product is obtained from 0.5 g of methyl 2-(4-hydroxybutyl)amino-2-(4-hydroxyphenyl)propionate (Yd=40%).

1H-NMR (CDCl3): δ 1.56 and 1.62 (2m, 4H, 2 CH2); 1.96 (s, 3H, Me); 3.09 and 3.54 (2m, 2H, NCH2); 3.67 (t, 2H, CH2O); 6.86 (d, 2 HAr); 7.28 (d, 2 HAr); 7.92 (d, 1 HAr); 8.01 (dd, 1 HAr); 8.16 (d, 1 HAr).

LC/MS Gradient 1: Rt: 4.3 min; 446– (M–H)–

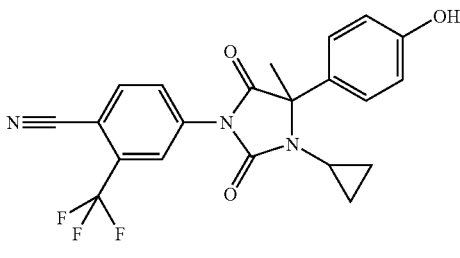

Example 24-1

4-[3-cyclopropyl-2,5-dioxo-4-(4-hydroxyphenyl)-4-methylimidazolidin-1-yl]-2-trifluoromethylbenzonitrile 0.285 g of product is obtained from 0.235 g of methyl 2-cyclopropylamino-2-(4-hydroxyphenyl)-propionate (Yd=69%).

1H-NMR (CDCl3): δ 0.6 (m, 2H, CH2); 0.8 (m, 2H, CH2); 1.94 (s, 3H, Me); 2.35 (m, 1H, CHN); 5.1 (sl, 1H, OH); 6.8 (d, 2 HAr); 7.13 (d, 2 HAr); 7.83 (d, 1 HAr); 7.9 (dd, 1 HAr); 8.05 (d, 1 HAr).

LC/MS Gradient 1: Rt: 2.9 min; 414– (M–H)–

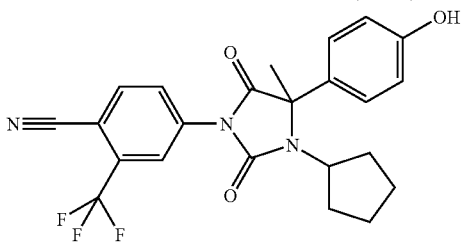

Example 24-2

4-[3-cyclopentyl-2,5-dioxo-4-(4-hydroxyphenyl)-4-methylimidazolidin-1-yl]-2-trifluoromethylbenzonitrile 0.265 g of product is obtained from 0.263 g of methyl 2-cyclopentylamino-2-(4-hydroxyphenyl)-propionate (Yd=60%).

1H-NMR (CDCl3): δ 1.5 (m, 2H, cyclopentyl); 1.72 (m, 1H, cyclopentyl); 1.9 (m, 3H, cyclopentyl); 1.94 (s, 3H, Me); 2.1 (m, 1H, cyclopentyl); 2.35 (m, 1H, cyclopentyl); 3.4 (quintuplet, 1H, CHN); 5.3 (sl, 1H, OH); 6.85 (d, 2 HAr); 7.25 (d, 2 HAr); 7.9 (d, 1 HAr); 8.0 (dd, 1 HAr); 8.16 (d, 1 HAr).

LC/MS Gradient 1: Rt: 5.2 min; 442– (M–H)–; 885– (2M–H)–

Examples 25 to 38

As in Example 5, using the same mode of operation with methyl 2-(4-hydroxyphenyl)-2-methylaminopropionate andthe appropriate isocyanate II, the following products are prepared:

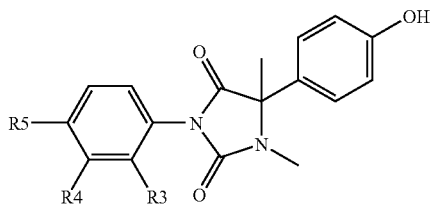

Example 25

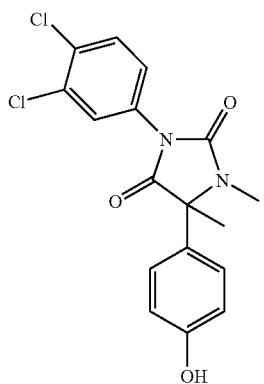

1-(3,4-dichlorophenyl)-3,4-dimethyl-4-(4-hydroxyphenyl)imidazolidine-2,5-dione 1.8 g of product is obtained from 2 g of the amino ester (Yd=51.5%); Mp=184° C.

1H-NMR (MeOD): δ 2.85 (s, 3H, Me); 3.32 (s, 3H, NMe); 6.85 (d, 2 HAr); 7.22 (d, 2 HAr); 7.45 (dl, 1 HAr); 7.62 (d, 1 HAr); 7.7 (sl, 1 HAr).

LC/MS Gradient 1: Rt: 4.78 min; 363– (M–H)–

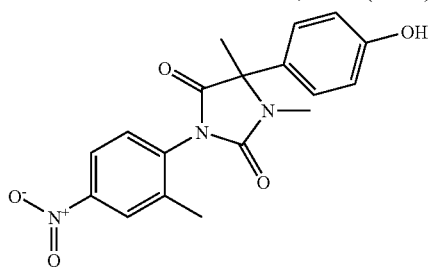

Example 26

3,4-dimethyl-4-(4-hydroxyphenyl)-1-(2-methyl-4-nitro-phenyl)imidazolidine-2,5-dione 1H-NMR (DMSO D6): δ 1.87 (s, 3H, Me); 2.16 and 2.29 (2s 6/4, 3H, PhMe); 2.74 and 2.78 (2s 4/6, 3H, NMe); 6.85 (2d, 2 HAr); 7.22 and 7.27 (2d 4/6, 2 HAr); 7.60 and 7.27 (2d 4/6, 1 HAr); 8.15 and 8.19 (2dd, 1 HAr); 8.25 and 8.30 (2d, 1 HAr); 9.70 (s, 1H, OH).

LC/MS Gradient 1: Rt: 4.34 min; 354– (M–H)–; 356+ (MH)+

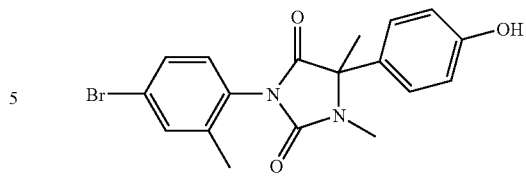

Example 27

1-(4-bromo-2-methylphenyl)-3,4-dimethyl-4-(4-hydroxyphenyl)imidazolidine-2,5-dione 47 mg of product are obtained from 80 g of the amino ester.

1H-NMR (MeOD): δ 1.85 (s, 3H, Me); 2.02 and 2.16 (2s, 3H, PhMe); 2.79 and 2.83 (2s, 3H, NMe); 6.82 (m, 2 HAr); 7.05 and 7.12 (2d, 1 HAr); 7.20 (d, 2 HAr); 7.42 (d, 1 HAr); 7.48 and 7.52 (2s, 1 HAr).

LC/MS Gradient 1: Rt: 4.55 min; 387/389– (M–H)–

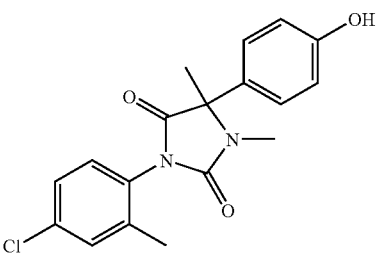

Example 28

1-(4-chloro-2-methylphenyl)-3,4-dimethyl-4-(4-hydroxyphenyl)imidazolidine-2,5-dione 1H-NMR (MeOD): δ 1.92 (s, 3H, Me); 2.10 and 2.21 (2s, 3H, PhMe); 2.87 and 2.90 (2s, 3H, NMe); 6.89 (dd, 2 HAr); 7.18 (d, 1 HAr); 7.26 (d, 2 HAr); 7.33 (dd, 1 HAr); 7.40 (m, 1 HAr).

LC/MS Gradient 1: Rt: 4.55 min; 343– (M–H)–

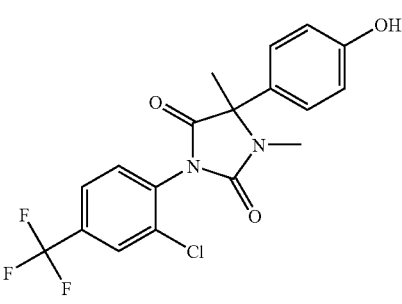

Example 29

1-(2-chloro-4-trifluoromethylphenyl)-3,4-dimethyl-4-(4-hydroxyphenyl)imidazolidine-2,5-dione 1H-NMR (CDCl3): δ 1.89 and 1.91 (2s, 3H, Me); 2.89 (s, 3H, NMe); 6.93 (m, 2 HAr); 7.20 and 7.28 (2dd, 2 HAr); 7.41 and 7.48 (2d, 1 HAr); 7.60 (m, 1 HAr); 7.78 (d, 1 HAr).

LC/MS Gradient 1: Rt: 4.89 min; 397– (M–H)–

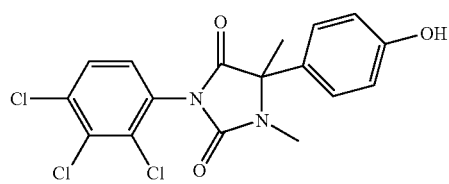

Example 30

3,4-dimethyl-4-(4-hydroxyphenyl)-1-(2,3,4-trichlorophenyl)imidazolidine-2,5-dione 54 mg of product are obtained from 80 g of the amino ester.

1H-NMR (MeOD): δ 1.88 (s, 3H, Me); 2.79 and 2.80 (2s, 3H, NMe); 6.81 (m, 2 HAr); 7.22 (d, 2 HAr); 7.72 and 7.82 (2d, 2 HAr).

LC/MS Gradient 1: Rt: 4.78 min; 397/399– (M–H)–

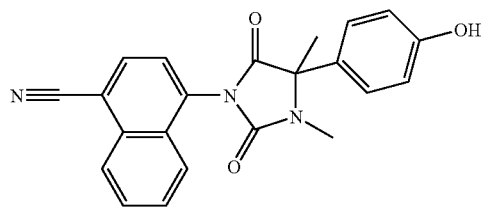

Example 31

4-[3,4-dimethyl-2,5-dioxo-4-(4-hydroxyphenyl)imidazolidin-1-yl]naphthonitrile 98 mg of product are obtained from 99 g of the amino ester.

1H-NMR (CDCl3): δ 2.01 and 2.09 (2s 65/45, 3H, Me); 2.98 and 3.02 (2s, 3H, NMe); 6.92 and 6.98 (2d, 2H phenyl); 7.30 and 7.40 (2d, 2H phenyl); 7.43-7.60 (m, 2H naphthyl); 7.7-7.82 (m, 2H naphthyl); 8.02 (2d, 1H naphthyl); 8.34 (2d, 1H naphthyl).

LC/MS Gradient 1: Rt: 2.17 min; 370– (M–H)–

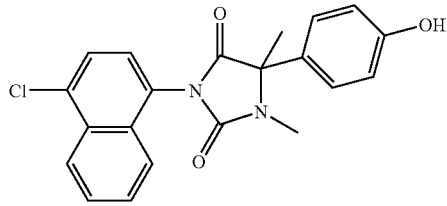

Example 32

1-(4-chloronaphthyl)-3,4-dimethyl-4-(4-hydroxyphenyl)imidazolidine-2,5-dione 49 mg of product are obtained from 98 g of the amino ester.
1H-NMR (CDCl3): δ 1.98 and 2.06 (2s 1/1, 3H, Me); 2.96 and 3.02 (2s 1/1, 3H, NMe); 6.85 (m, 2 HAr); 7.22-7.41 (m, 3 HAr); 7.5-7.68 (2m, 4 HAr); 8.35 (m, 1 HAr).

LC/MS Gradient 1: Rt: 2.73 min; 378/379– (M–H)–

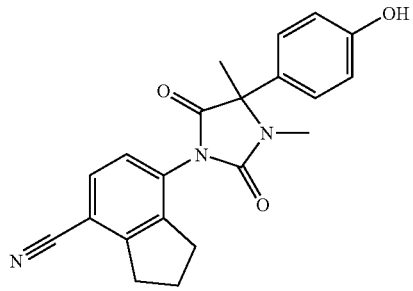

Example 33

2,3-dihydro-7-[3,4-dimethyl-2,5-dioxo-4-(4-hydroxyphenyl)imidazolidin-1-yl]-4(1H)-indenenitrile 0.53 g of product is obtained from 0.42 g of the amino ester.
1H-NMR (CDCl3): δ 1.92 (s, 3H, Me); 2.15 (m, 2H, CH2); 2.82 (m, 2H, CH2); 2.91 (s, 3H, NMe); 3.17 (t, 2H, PhCH2); 5.32 (s, 1H, OH); 6.87 (d, 2 HAr); 7.22 (d, 3 HAr); 7.53 (d, 1 HAr).

LC/MS Gradient 1: Rt: 3.44 min; 360– (M–H)–

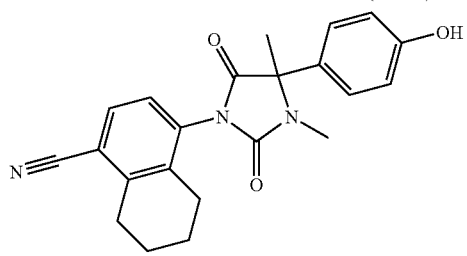

Example 34

8-[3,4-dimethyl-2,5-dioxo-4-(4-hydroxyphenyl)imidazolidin-1-yl]-1,2,3,4-tetrahydro-5-naphthonitrile 57 mg of product are obtained from 96 mg of the amino ester.

1H-NMR (DMSO D6): δ 1.65-1.85 (m, 4H, CH2); 1.85 (s, 3H, Me); 2.55 (m, 2H, CH2); 2.72 and 2.77 (2s 1/1, 3H, NMe); 2.93 (m, 2H, CH2); 6.85 (m, 2 HAr); 7.23 (2d 1/1, 2 HAr); 7.31 and 7.40 (2d 1/1, 1 HAr); 7.77 (m, 1 HAr); 9.7 (sl, 1H, OH).

LC/MS Gradient 1: Rt: 3.41 min; 374– (M–H)–

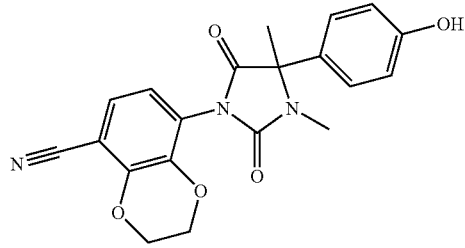

Example 35

4-[3,4-dimethyl-2,5-dioxo-4-(4-hydroxyphenyl)imidazolidin-1-yl]-2,3-(1,2-ethylenedioxy)-benzonitrile 113 mg of product are obtained from 161 mg of the amino ester.

1H-NMR (CDCl3): δ 1.91 (s, 3H, Me); 2.86 and 2.89 (2s 1/1, 3H, NMe); 4.7-4.95 (m, 4H, OCH2); 5.47 (s, 1H, OH); 6.82 (d, 2 HAr); 6.86 and 6.94 (2d, 1 HAr); 7.17-7.27 (m, 3 HAr).

LC/MS Gradient 1: Rt: 3.07 min; 378– (M–H)–

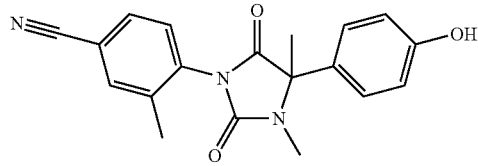

Example 36

4-[3,4-dimethyl-2,5-dioxo-4-(4-hydroxyphenyl)imidazolidin-1-yl]-3-methylbenzonitrile 145 mg of product are obtained from 227 mg of the amino ester.

1H-NMR (MeOD): δ 1.92 (s, 3H, Me); 2.15 and 2.29 (2s 6/4, 3H, PhMe); 2.86 and 2.90 (2s 4/6, 2H, NMe); 6.88 (d, 2 HAr); 7.37 and 7.48 (2d 4/6, 1 HAr); 7.65-7.85 (m, 2 HAr).

LC/MS Gradient 1: Rt: 3.25 min; 334– (M–H)–

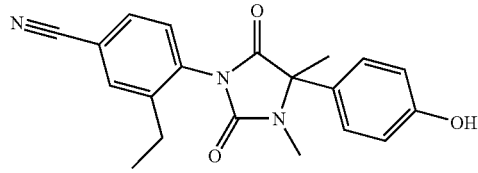

Example 37

4-[3,4-dimethyl-2,5-dioxo-4-(4-hydroxyphenyl)imidazolidin-1-yl]-3-ethylbenzonitrile 146 mg of product are obtained from 144 mg of the amino ester.

1H-NMR (MeOD): δ 1.06 and 1.26 (2t 6/4, 3H, CH2CH3); 1.93 (s, 3H, Me); 2.47 and 2.63 (2q 6/4, 2H, CH2-CH3); 2.87 and 2.92 (2s 4/6, 3H, NMe); 6.9 (d, 2 HAr); 7.26 (m, 2 HAr); 7.38 and 7.48 (2d 4/6, 1 HAr); 7.69-7.83 (m, 2 HAr).

LC/MS Gradient 1: Rt: 3.42 min; 348– (M–H)–

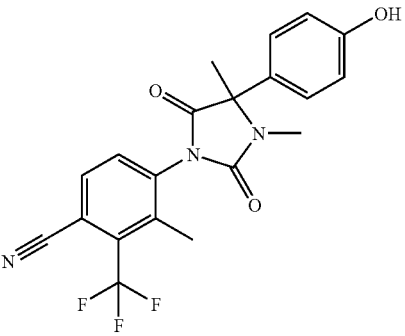

Example 38

4-[3,4-dimethyl-2,5-dioxo-4-(4-hydroxyphenyl)imidazolidin-1-yl]-3-methyl-2-trifluoromethylbenzonitrile 238 mg of product are obtained from 152 mg of the amino ester (Yd=81%).

1H-NMR (MeOD): δ 1.98 (m, 3H, Me); 2.26 and 2.41 (2s, 3H, PhMe); 2.88 and 2.92 (2s, 3H, NMe); 6.90 (d, 2 HAr); 7.29 (d, 2 HAr); 7.71 and 7.81 (2d, 1 HAr); 7.97 (m, 1 HAr).

LC/MS Gradient 1: Rt: 3.60 min; 402– (M–H)–

Examples 39 to 44

As for Example 5, using the same mode of operation with the appropriate amino ester III and isothiocyanate II, the following products are prepared:

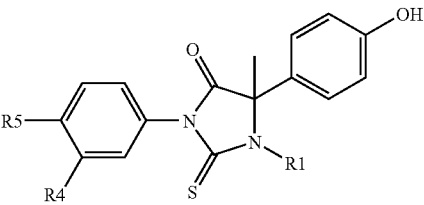

Example 39

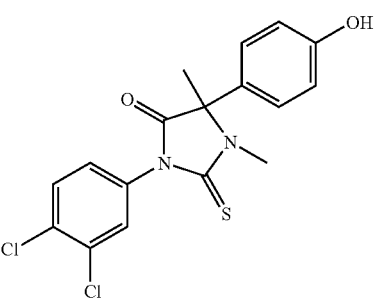

1-(3,4-dichlorophenyl)-3,4-dimethyl-4-(4-hydroxyphenyl)-2-thioxoimidazolidin-5-one 0.69 g of product is obtained from 0.48 g of methyl 2-(4-hydroxyphenyl)-2-methylaminopropionate (Yd=77%); Mp=194° C.

1H-NMR (CDCl3): δ 1.92 (s, 3H, Me); 3.2 (s, 3H, NMe); 6.85 (d, 2 HAr); 7.12 (d, 2 HAr); 7.42 (dd, 1 HAr); 7.5 (d, 1 HAr); 7.6 (s, 1 HAr).

LC/MS Gradient 1: Rt: 5.00 min; 379/381− (M−H)−

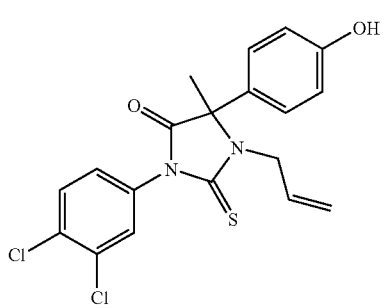

Example 40

1-(3,4-dichlorophenyl)-4-(4-hydroxyphenyl)-4-methyl-3-(2-propenyl)-2-thioxoimidazolidin-5-one 0.50 g of product is obtained from 0.35 g of methyl 2-(4-hydroxyphenyl)-2-(2-propenyl)aminopropionate (Yd=83%).

1H-NMR (CDCl3): δ 1.95 (s, 3H, Me); 3.79 and 4.75 (2 dd, 2H, NCH2); 5.2 and 5.23 (s and d, 2H, CH=CH2); 5.93 (m, 1H, CH=CH2); 6.87 (m, 2 HAr); 7.15 (m, 2 HAr); 7.25 (dd, 1 HAr); 7.49 (d, 1 HAr); 7.57 (d, 1 HAr).

LC/MS Gradient 1: Rt: 5.27 min; 405/407− (M−H)−

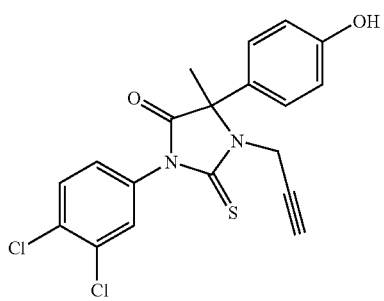

Example 41

1-(3,4-dichlorophenyl)-4-(4-hydroxyphenyl)-4-methyl-3-(2-propynyl)-2-thioxoimidazolidin-5-one 0.35 g of product is obtained from 0.34 g of methyl 2-(4-hydroxyphenyl)-2-(2-propenyl)aminopropionate (Yd=58%).

1H-NMR (CDCl3): δ 2.09 (s, 3H, Me); 2.29 (m, 1H, HC); 3.93 and 4.97 (2 dd, 2H, NCH2); 6.88 (m, 2 HAr); 7.17 (m, 2 HAr); 7.26 (dd, 1 HAr); 7.51 (m, 1 HAr); 7.58 (d, 1 HAr).

LC/MS Gradient 1: Rt: 5.08 min; 403/405− (M−H)−

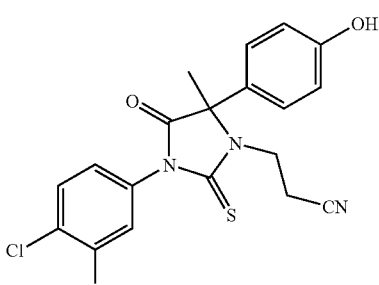

Example 42

3-[1-(3,4-dichlorophenyl)-4-(4-hydroxyphenyl)-4-methyl-5-oxo-2-thioxoimidazolidin-3-yl]-propionitrile 0.44 g of product is obtained from 0.37 g of methyl 2-(4-hydroxyphenyl)-2-(2-propenyl)aminopropionate (Yd=71%).

1H-NMR (CDCl3): δ 2.03 (s, 3H, Me); 2.69 and 4.4 (2m, 2H, CH2); 3.15 and 3.59 (2dt, 2H, CH2); 6.92 (m, 2 HAr); 7.15 (m, 2 HAr); 7.24 (dd, 1 HAr); 7.49 (d, 1 HAr); 7.59 (d, 1 HAr).

LC/MS Gradient 1: Rt: 4.99 min; 418/420− (M−H)−

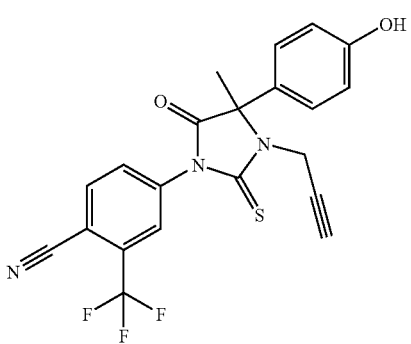

Example 43

4-[4-(4-hydroxyphenyl)-4-methyl-5-oxo-3-(2-propynyl)-2-thioxoimidazolidin-1-yl]-2-trifluoromethylbenzonitrile 0.44 g of product is obtained from 0.76 g of methyl 2-(4-hydroxyphenyl)-2-(2-propenyl)aminopropionate (Yd=39%); Mp=169° C.

1H-NMR (CDCl3): δ 2.12 (s, 3H, Me); 2.31 (m, 1H, HC); 3.96 and 4.98 (2dd, 2H, NCH2); 6.91 (d, 2 HAr); 7.18 (d, 2 HAr); 7.80 (dd, 1 HAr); 7.92 (s, 1 HAr); 7.97 (d, 1 HAr).

LC/MS Gradient 1: Rt: 4.93 min; 428– (M–H)–

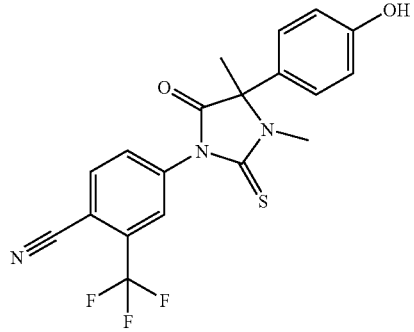

Example 44

4-[3,4-dimethyl-4-(4-hydroxyphenyl)-5-oxo-2-thioxoimidazolidin-1-yl]-2-trifluoromethylbenzonitrile 0.629 g of product is obtained from 0.43 g of methyl 2-(4-hydroxyphenyl)-2-methylaminopropionate (Yd=75%).

1H-NMR (DMSO D6): δ 1.93 (s, 3H, Me); 3.06 (s, 3H, MeN); 6.84 (d, 2 HAr); 7.22 (d, 2 HAr); 8.05 (d, 1 HAr); 8.28 (s, 1 HAr); 8.36 (d, 1 HAr); 9.78 (s, 1H, OH).

LC/MS Gradient 1: Rt: 4.87 min; 404– (M–H)–; 809– (2M–H)–

Examples 45 to 150

The method according to Example 4 with the appropriate isocyanate II and amino ester III was used to prepare the following products:

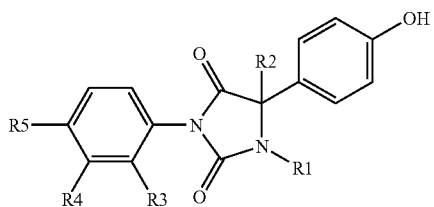

| Ex No. | R1 | R2 | R3 | R4 | R5 | LC/MS tr Rt (min) | LC/MS M/z |
|---|---|---|---|---|---|---|---|
| 45 | Me | H | H | CF3 | NO2 | 4.75 | 394– |
| 46 | Me | H | H | F | F | 4.52 | 317– |
| 47 | Me | H | H | CF3 | Cl | 5.14 | 383– |
| 48 | Me | H | H | CF3 | F | 4.93 | 367– |
| 49 | Me | H | H | Cl | F | 4.68 | 333– |
| 50 | Me | H | H | H | NO2 | 4.01 | 326–; 653– |
| 51 | (3-thienyl)methanol | H | H | Cl | F | 4.99 | 415–; 831– |
| 52 | (3-thienyl)methanol | H | Cl | H | Cl | 4.88 | 433– |
| 53 | (3-thienyl)methyl | H | H | H | NO2 | 4.74 | 408– |
| 54 | propyl | H | H | CF3 | NO2 | 5.15 | 422– |
| 55 | propyl | H | H | Cl | Cl | 5.44 | 377– |
| 56 | propyl | H | H | FF | F | 5.01 | 345– |
| 57 | propyl | H | H | CF3 | Cl | 5.55 | 411– |
| 58 | propyl | H | H | CF3 | F | 5.36 | 394– |
| 59 | propyl | H | H | CF3 | H | 5.24 | 377– |
| 60 | propyl | H | H | CF3 | CN | 5.28 | 402– |
| 61 | 2-propenyl | H | H | CF3 | Cl | 5.46 | 409– |
| 62 | 2-propenyl | H | H | CF3 | F | 5.27 | 393– |
| 63 | 2-propenyl | H | H | Cl | F | 4.64 | 359– |
| 64 | 2-propenyl | H | H | CF3 | H | 5.11 | 375– |
| 65 | 2-propenyl | H | H | H | NO2 | 4.91 | 352– |
| 66 | 2-propynyl | H | H | Cl | Cl | 5.27 | 373– |
| 67 | 2-propynyl | H | H | F | F | 4.56 | 341– |
| 68 | 2-propynyl | H | H | CF3 | Cl | 5.51 | 407– |
| 69 | 2-propynyl | H | H | CF3 | F | 5.21 | 391– |
| 70 | 2-propynyl | H | H | Cl | F | 5.07 | 357– |
| 71 | 2-propynyl | H | H | CF3 | NO2 | 5.00 | 418– |
| 72 | 2-propynyl | H | H | CF3 | H | 5.07 | 373– |
| 73 | 2-propynyl | H | H | H | NO2 | 4.33 | 350– |
| 74 | 2-(ethoxycarbonyl)ethyl | H | H | CF3 | CN | 5.23 | 460– |
| 75 | 2-(ethoxycarbonyl)ethyl | H | H | CF3 | NO2 | 5.07 | 480– |
| 76 | 2-(ethoxycarbonyl)ethyl | H | H | F | F | 4.91 | 403– |
| 77 | 2-(ethoxycarbonyl)ethyl | H | H | CF3 | Cl | 5.42 | 469/471– |
| 78 | 2-(ethoxycarbonyl)ethyl | H | H | CF3 | F | 5.25 | 453– |
| 79 | 2-(ethoxycarbonyl)ethyl | H | H | Cl | F | 5.04 | 421+ |
| 80 | 2-(ethoxycarbonyl)ethyl | H | H | CF3 | H | 5.14 | 435– |
| 81 | 2-(ethoxycarbonyl)ethyl | H | H | H | NO2 | 4.90 | 412–; 825– |
| 82 | 3-ethoxypropyl | H | H | CF3 | CN | 5.19 | 446– |
| 83 | 3-ethoxypropyl | H | H | CF3 | NO2 | 5.07 | 466– |
| 84 | 3-ethoxypropyl | H | H | Cl | Cl | 5.38 | 421/423– |
| 85 | 3-ethoxypropyl | H | H | F | F | 4.87 | 389– |

-continued

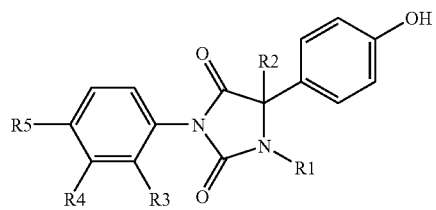

| Ex No. | R1 | R2 | R3 | R4 | R5 | LC/MS tr Rt (min) | LC/MS M/z |
|---|---|---|---|---|---|---|---|
| 86 | 3-ethoxypropyl | H | H | CF3 | Cl | 5.45 | 455− |
| 87 | 3-ethoxypropyl | H | H | CF3 | F | 5.21 | 439− |
| 88 | 3-ethoxypropyl | H | H | Cl | F | 5.77 | 405− |
| 89 | 3-ethoxypropyl | H | H | CF3 | H | 5.14 | 421− |
| 90 | cyanomethyl | H | H | CF3 | CN | 5.01 | 399− |
| 91 | cyanomethyl | H | H | Cl | Cl | 1.11 | No ionisation |
| 92 | cyanomethyl | H | H | F | F | 4.67 | 342− |
| 93 | cyanomethyl | H | H | CF3 | Cl | 4.96 | 408− |
| 94 | cyanomethyl | H | H | CF3 | F | 5.03 | 392− |
| 95 | cyanomethyl | H | H | Cl | F | 4.90 | 358− |
| 96 | cyanomethyl | H | H | CF3 | H | 4.94 | 374− |
| 97 | (3,4-methylenedioxy)phenylmethyl | H | H | CF3 | CN | 5.53 | 494− |
| 98 | (3,4-methylenedioxy)phenylmethyl | H | H | CF3 | NO2 | 5.40 | 514− |
| 99 | (3,4-methylenedioxy)phenylmethyl | H | H | Cl | Cl | 5.74 | 469/471− |
| 100 | (3,4-methylenedioxy)phenylmethyl | H | H | F | F | 5.40 | 437− |
| 101 | (3,4-methylenedioxy)phenylmethyl | H | H | CF3 | Cl | 5.74 | 503− |
| 102 | (3,4-methylenedioxy)phenylmethyl | H | H | CF3 | F | 5.03 | 487− |
| 103 | (3,4-methylenedioxy)phenylmethyl | H | H | Cl | F | 5.50 | 453− |
| 104 | (3,4-methylenedioxy)phenylmethyl | H | H | CF3 | H | 5.53 | 469− |
| 105 | (4-hydroxy-3-methoxy)phenylmethyl | H | H | CF3 | CN | 5.17 | 360−; 993− |
| 106 | (4-hydroxy-3-methoxy)phenylmethyl | H | H | CF3 | NO2 | 5.04 | 1033− |
| 107 | (4-hydroxy-3-methoxy)phenylmethyl | H | H | Cl | Cl | 5.24 | 335− |
| 108 | (4-hydroxy-3-methoxy)phenylmethyl | H | H | F | F | 4.85 | 879− |
| 109 | (4-hydroxy-3-methoxy)phenylmethyl | H | H | CF3 | Cl | 5.37 | 1011− |
| 110 | (4-hydroxy-3-methoxy)phenylmethyl | H | H | CF3 | F | 5.21 | 979− |
| 111 | (4-hydroxy-3-methoxy)phenylmethyl | H | H | Cl | F | 5.04 | 911− |
| 112 | (4-hydroxy-3-methoxy)phenylmethyl | H | H | CF3 | H | 5.09 | 943− |
| 113 | 2-(dimethylamino)ethyl | H | H | CF3 | CN | 1.02 | 431− |
| 114 | 2-(dimethylamino)ethyl | H | H | CF3 | NO2 | 1.02 | 451− |
| 115 | 2-(dimethylamino)ethyl | H | H | Cl | Cl | 1.04 | 406/408− |
| 116 | 2-(dimethylamino)ethyl | H | H | F | F | 1.25 | 376+ |
| 117 | 2-(dimethylamino)ethyl | H | H | CF3 | Cl | 1.07 | 438/440− |
| 118 | 2-(dimethylamino)ethyl | H | H | CF3 | F | 1.04 | 424− |
| 119 | 2-(dimethylamino)ethyl | H | H | Cl | F | 1.04 | 390− |
| 120 | 2-(dimethylamino)ethyl | H | H | CF3 | H | 1.04 | 406− |
| 121 | 2-cyanoethyl | H | H | CF3 | CN | 4.93 | 413− |
| 122 | 2-cyanoethyl | H | H | CF3 | NO2 | 4.79 | 433− |
| 123 | 2-cyanoethyl | H | H | Cl | Cl | 5.09 | 388− |
| 124 | 2-cyanoethyl | H | H | F | F | 4.77 | 356− |
| 125 | 2-cyanoethyl | H | H | CF3 | Cl | 5.17 | 422− |
| 126 | 2-cyanoethyl | H | H | CF3 | F | 4.98 | 406− |
| 127 | 2-cyanoethyl | H | H | Cl | F | 4.79 | 372− |
| 128 | 2-cyanoethyl | H | H | CF3 | H | 4.80 | 388− |
| 129 | 2-cyanoethyl | H | H | H | NO2 | 4.00 | 365−; 731− |
| 130 | 4-hydroxybutyl | H | H | CF3 | CN | 1.07 | 430− |
| 131 | 4-hydroxybutyl | H | H | CF3 | NO2 | 4.37 | 452− |
| 132 | 4-hydroxybutyl | H | H | Cl | Cl | 4.56 | 407/409− |
| 133 | 4-hydroxybutyl | H | H | F | F | 4.66 | 375−; 751− |
| 134 | 4-hydroxybutyl | H | H | CF3 | Cl | 4.90 | 441− |
| 135 | 4-hydroxybutyl | H | H | CF3 | F | 4.69 | 425− |
| 136 | 4-hydroxybutyl | H | H | CF3 | H | 4.55 | 407− |
| 137 | 2-hydroxyethyl | H | H | CF3 | CN | 4.54 | 404− |
| 138 | 2-hydroxyethyl | H | H | CF3 | NO2 | 4.24 | 424− |
| 139 | 2-hydroxyethyl | H | H | Cl | Cl | 4.47 | 379/381− |
| 140 | 2-hydroxyethyl | H | H | F | F | 1.42 | 347− |
| 141 | 2-hydroxyethyl | H | H | CF3 | Cl | 4.75 | 413− |
| 142 | 2-hydroxyethyl | H | H | CF3 | F | 4.69 | 397− |
| 143 | 2-hydroxyethyl | H | H | Cl | F | 4.39 | 379− |
| 144 | 2-hydroxyethyl | H | H | CF3 | H | 4.26 | 363− |
| 145 | 2-cyanoethyl | Me | H | Cl | Cl | 5.15 | 402/404− |
| 146 | 2-hydroxyethyl | Me | H | Cl | Cl | 4.74 | 393/395− |
| 147 | 3-hydroxypropyl | Me | H | Cl | Cl | 4.79 | 407/409− |
| 149 | 2-cyanoethyl | Me | H | CF3 | CN | 5.06 | 427− |
| 150 | 3-hydroxypropyl | Me | H | CF3 | CN | 4.73 | 432− |

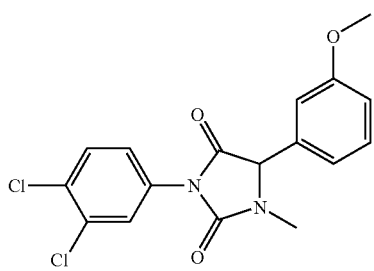

Example 151

1-(3,4-dichlorophenyl)-4-(3-methoxyphenyl)-3-methylimidazolidine-2,5-dione 3 g of methyl 2-(3-methoxyphenyl)-2-methylaminoacetate were introduced into a 250 mL Woulff bottle at ambient temperature. 2.7 g d of 3,4-dichlorophenyl isocyanate in 50 mL of THF were added and the mixture was stirred for 30 min at ambient temperature. The insoluble matter was filtered, washed with isopropyl ether and dried to yield the product in the form of a white solid (3.9 g; Yd=75%).

1H-NMR (CDCl3): δ 3.0 (s, 3H, NMe); 3.85 (s, 3H, OMe); 4.9 (s, 1H, NCHCO); 6.85 (s, 1 HAr); 6.9 (d, 1 HAr); 6.98 (dd, 1 HAr); 7.38 (m, 2 HAr); 7.52 (d, 1 HAr); 7.65 (d, 1 HAr).

LC/MS Gradient 1: Rt: 5.17 min; 363/365– (M–H)–

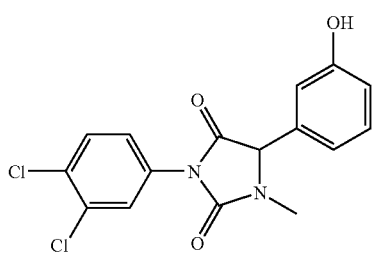

Example 152

1-(3,4-dichlorophenyl)-4-(3-hydroxyphenyl)-3-methylimidazolidine-2,5-dione 10.5 mL of boron trifluoride/dimethyl sulphide complex are added dropwise, at ambient temperature, to 3.7 g of a solution of 3-(3,4-dichlorophenyl)-5-(3-methoxyphenyl)-1-methylimidazolidine-2,4-dione in 60 mL of dichloromethane in a flask equipped with a magnetic stirrer and a nitrogen intake. After 2 hours at ambient temperature, the mixture is poured over a saturated aqueous sodium bicarbonate solution and subjected to extraction with ethyl acetate. The mixture is dried over magnesium sulphate and concentrated. The residue is crystallised in isopropyl ether (white solid; m=3 g; Yd=84%).

LC/MS Gradient 1: Rt: 4.68 min; 349– (M–H)–

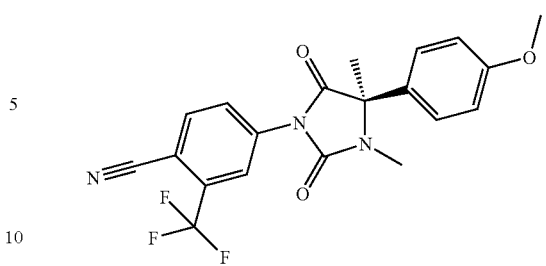

Example 153

(R)-4-[3,4-dimethyl-2,5-dioxo-4-(4-methoxyphenyl)imidazolidin-1-yl]-2-trifluoromethylbenzonitrile 5.4 g of (R)-4-[2,5-dioxo-4-(4-methoxyphenyl)-4-methylimidazolidin-1-yl]-2-trifluoromethylbenzonitrile are dissolved in 100 mL of DMF under argon. 908 mg of sodium hydride, 55% in oil, are added batchwise at 0° C. The mixture is stirred at 0° C. for 15 min, then 1.75 mL of methyl iodide are added and the mixture is stirred for a further 2 hours at AT. The mixture is poured over iced water and the product is extracted with ethyl acetate. The organic phase is washed with a saturated aqueous sodium bicarbonate solution then a saturated sodium chloride solution. After drying over magnesium sulphate, filtration and concentration, the residue is purified by chromatography over silica while eluting with a (2/1) heptane/ethyl acetate mixture. 4.5 g of product are obtained in the form of a white solid (Yd=80%).

TLC: Fr=0.2 (2/1 heptane/ethyl acetate).

[α]D=+28.2° (c=1%, MeOH).

1H-NMR (CDCl3): δ 1.95 (s, 3H, Me); 2.95 (s, 3H, NMe); 3.85 (s, 3H, OMe); 6.98 (d, 2 HAr); 7.28 (d, 2 HAr); 7.91 (d, 1 HAr); 8.02 (dd, 1 HAr); 8.18 (d, 1 HAr).

LC/MS Gradient 1: Rt: 4.54 min; 404+ (MH)+

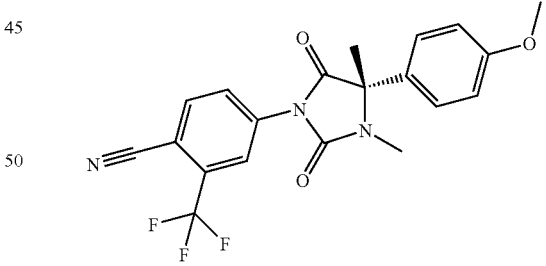

Example 154

(S)-4-[3,4-dimethyl-2,5-dioxo-4-(4-methoxyphenyl)imidazolidin-1-yl]-2-trifluoromethylbenzonitrile Following the method of Example 153, 1.15 g of product (quantitative yield) is obtained from 915 mg of (S)-4-[2,5- dioxo-4-(4-methoxyphenyl)-4-methylimidazolidin-1-yl]-2-trifluoromethylbenzonitrile.

TLC: Fr=0.27 (60/40 heptane/ethyl acetate).

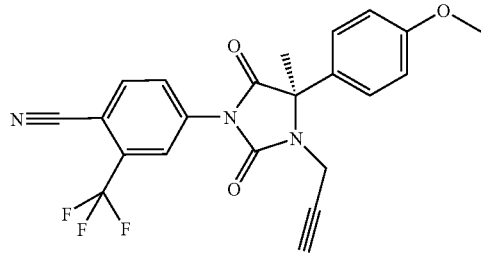

Example 154-1

(R)-4-[2,5-dioxo-4-(4-methoxyphenyl)-4-methyl-3-(2-propynyl)imidazolidin-1-yl]-2-trifluoromethylbenzonitrile Using the method of Example 153 from 1.5 g of (R)-4-[2,5-dioxo-4-(4-methoxyphenyl)-4-methylimidazolidin-1-yl]-2-trifluoromethylbenzonitrile and with propargyl bromide as the alkylating agent, 1.3 g of compound was obtained after chromatography on silica gel (eluent 80/20 to 50/50 heptane/ethyl acetate) (Yd=80%).

1H-NMR (DMSO D6): δ 2.00 (s, 3H, Me); 3.20 (s, 1H, CH); 3.80 and 4.30 (2d, 2H, NCH2); 3.78 (s, 3H, OMe); 6.98 (d, 2 HAr); 7.42 (d, 2 HAr); 8.09 (d, 1 HAr); 8.27 (s, 1 HAr); 8.33 (d, 1 HAr).

LC/MS Gradient 1: Rt: 3.7 min; no ionisation

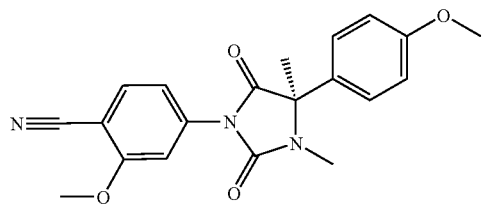

Example 154-2

(R)-4-[3,4-dimethyl-2,5-dioxo-4-(4-methoxyphenyl)imidazolidin-1-yl]-2-methoxybenzonitrile To a solution of 2.4 g of (R)-4-[2,5-dioxo-4-(4-methoxyphenyl)-4-methylimidazolidin-1-yl]-2-methoxybenzonitrile and 0.468 mL of iodomethane in 30 mL of N,N-dimethylacetamide, 376 mg of sodium hydride (50% dispersion in mineral oil) are added. The mixture is stirred at AT for 3 hours, evaporated to dryness, diluted with water and extracted with ethyl acetate. The organic layer is dried over magnesium sulphate, filtered and evaporated. The crude product is purified by chromatography over silica gel while eluting with 50/50 heptane/ethyl acetate. 1.83 g of white solid is obtained (Yd=73%).

TLC: Fr=0.28 (50/50 heptane/ethyl acetate).

1H-NMR (CDCl3): δ 1.92 (s, 3H, Me); 2.93 (s, 3H, NMe); 3.84 (s, 3H, OMe); 3.94 (s, 3H, OMe); 6.98 (d, 2 HAr); 7.25 to 7.29 (m, 4 HAr); 7.62 (d, 1 HAr).

LC/MS Gradient 1: Rt: 4.66 min; 366+ (MH)+

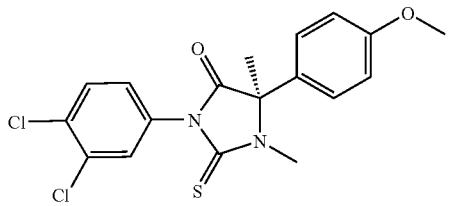

Example 154-3

(R)-1-(3,4-dichlorophenyl)-3,4-dimethyl-4-(4-methoxyphenyl)-2-thioxoimidazolidin-5-one 0.185 mL of triethylamine and 0.230 g of 3,4-dichlorophenylisothiocyanate are added to a solution of 0.246 g of methyl (R)-2-(4-methoxyphenyl)-2-methylaminopropionate in 10 mL of THF. The mixture is stirred at AT for 1 hour and evaporated to dryness. The crude product is diluted with water and extracted with ethyl acetate. The organic layer is dried over magnesium sulphate, filtered and evaporated. The crude product is purified by chromatography over silica gel while eluting with 80/20 heptane/ethyl acetate. 0.41 g of white solid is obtained (Yd=95%).

TLC: Fr=0.48 (70/30 heptane/ethyl acetate).

1H-NMR (CDCl3): δ 1.96 (s, 3H, Me); 3.22 (s, 3H, NMe); 3.84 (s, 3H, OMe); 6.99 (d, 2 HAr); 7.20 to 7.27 (m, 3 HAr); 7.49 (d, 1 HAr); 7.57 (d, 1 HAr).

LC/MS Gradient 1: Rt: 6.46 min; 395/397+ (MH)+

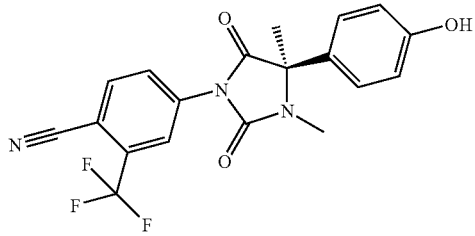

Example 155

(R)-4-[3,4-dimethyl-2,5-dioxo-4-(4-hydroxyphenyl)imidazolidin-1-yl]-2-trifluoromethylbenzonitrile 7.83 mL of boron trifluoride/dimethyl sulphide complex are added dropwise to 3 g of (R)-4-[3,4-dimethyl-2,5-dioxo-4-(4-methoxyphenyl)imidazolidin-1-yl]-2-trifluoromethylbenzonitrile in solution in 70 mL of dichloromethane under argon. After 24 hours at AT, a saturated aqueous sodium bicarbonate solution is added until the pH reaches 8 then the product is extracted with dichloromethane. The organic phase is washed with a saturated sodium chloride solution and dried over magnesium sulphate. The mixture is filtered and concentrated to dryness, then the residue is purified by chromatography over silica while eluting with a (2/1) heptane/ethyl acetate mixture. 2.8 g of product are obtained in the form of a white solid (Yd=96%); Mp=150.7° C.

[α]D=+29.2° (c=1%, MeOH).

TLC: Fr=0.2 (2/1 heptane/ethyl acetate).

1H-NMR (MeOD): δ 2.04 (s, 3H, Me); 2.98 (s, 3H, NMe); 6.98 (d, 2 HAr); 7.36 (d, 2 HAr); 8.18 (d, 1 HAr); 8.24 (dd, 1 HAr); 8.33 (d, 1 HAr).

LC/MS Gradient 1: Rt: 4.00 min; 388− (M−H)−

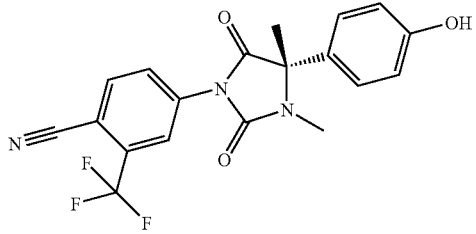

Example 156

(S)-4-[3,4-dimethyl-2,5-dioxo-4-(4-hydroxyphenyl) imidazolidin-1-yl]-2-trifluoromethylbenzonitrile Following the method according to the previous example, 867 mg of product (white solid, yield=95%) are obtained from 1.15 g of (S)-4-[3,4-dimethyl-2,5-dioxo-4-(4-methoxyphenyl)imidazolidin-1-yl]-2-trifluoromethylbenzonitrile.

[α]D=−28° (c=1%, MeOH).

TLC: Fr=0.23 (60/40 heptane/ethyl acetate).

1H-NMR (MeOD): δ 1.94 (s, 3H, Me); 2.91 (s, 3H, NMe); 6.89 (d, 2 HAr); 7.27 (d, 2 HAr); 8.10 (AB, 2 HAr); 8.23 (s, 1 HAr).

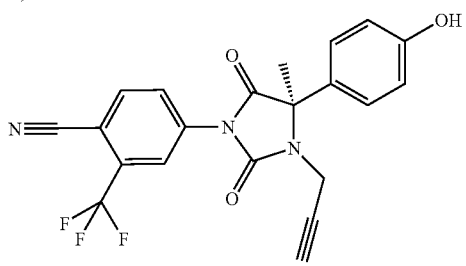

Example 156-1

(R)-4-[2,5-dioxo-4-(4-hydroxyphenyl)-4-methyl-3-(2-propynyl)imidazolidin-1-yl]-2-trifluoromethyl-benzonitrile Using the method of Example 155 from 1.4 g of (R)-4-[2,5-dioxo-4-(4-methoxyphenyl)-4-methyl-3-(2-propynyl)imidazolidin-1-yl]-2-trifluoromethylbenzonitrile with 3.45 mL of boron trifluoride/dimethyl sulfide complex in 30 mL of dichloromethane, 1.2 g of product was obtained after chromatographic purification on silica gel (eluent dichloromethane to 80/20 dichloromethane/ethyl acetate) (Yd=88%).

[α]D=+22.0° (c=1%, MeOH).

1H-NMR (DMSO D6): δ 2.19 (s, 3H, Me); 3.21 (s, 1H, CH); 3.79 and 4.30 (2d, 2H, NCH2); 6.80 (d, 2 HAr); 7.30 (d, 2 HAr); 8.10 (d, 1 HAr); 8.28 (s, 1 HAr); 8.35 (d, 1 HAr); 9.70 (s, 1H, OH).

LC/MS Gradient 1: Rt: 3.47 min; 412− (M−H)−

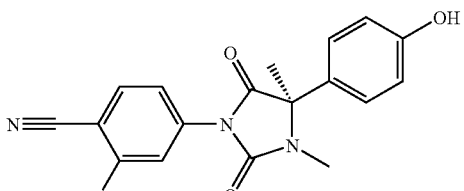

Example 156-2

(R)-4-[3,4-dimethyl-2,5-dioxo-4-(4-hydroxyphenyl) imidazolidin-1-yl]-2-methoxybenzonitrile 5.3 mL of boron trifluoride/dimethyl sulphide complex in 20 ml of dichloromethane are added to a solution of 1.8 g of (R)-4-[3,4-dimethyl-2,5-dioxo-4-(4-methoxyphenyl)imidazolidin-1-yl]-2-methoxybenzonitrile in 110 mL of dichloromethane. The mixture is stirred at AT for 12 hours and poured into a saturated aqueous sodium bicarbonate solution and extracted with ethyl acetate. The organic layer is dried over magnesium sulphate, filtered and evaporated. The crude product is purified by chromatography over silica gel while eluting with a 70/30 heptane/ethyl acetate mixture. 1.29 g of a white crystalline solid is obtained (Yd=75%); Mp=100° C.

[α]D=+35.2° (c=1%, MeOH).

TLC: Fr=0.25 (50/50 heptane/ethyl acetate).

1H-NMR (CDCl3): δ 1.92 (s, 3H, Me); 2.93 (s, 3H, NMe); 3.94 (s, 3H, OMe); 6.87 (d, 2 HAr); 7.20 to 7.29 (m, 4 HAr); 7.62 (d, 1 HAr).

LC/MS Gradient 1: Rt: 4.44 min; 350− (M−H)−

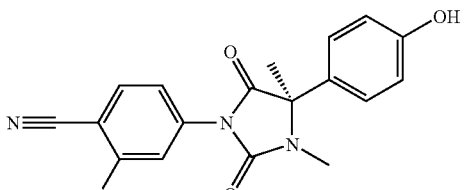

Example 156-3

(R)-4-[3,4-dimethyl-2,5-dioxo-4-(4-hydroxyphenyl) imidazolidin-1-yl]-2-hydroxybenzonitrile A solution of 4 mL of boron trifluoride/dimethylsulphide complex in 10 mL of dichloromethane is added to a solution of 0.66 g of (R)-4-[3,4-dimethyl-2,5-dioxo-4-(4-methoxyphenyl)imidazolidin-1-yl]-2-methoxybenzonitrile in 50 mL of dichloromethane. The mixture is stirred at AT for 24 hours and poured into a saturated aqueous sodium bicarbonate solution and extracted with ethyl acetate. The organic layer is dried over magnesium sulphate, filtered and evaporated. The crude product is purified by chromatography over silica gel while eluting with a 25/25/25/25 diisopropyl ether/dichloromethane/heptane/ethyl acetate mixture. 0.03 g of white crystalline solid is obtained (Yd=5%).

TLC: Fr=0.35 (25/75 heptane/ethyl acetate).

1H-NMR (CDCl3): δ 1.84 (s, 3H, Me); 2.85 (s, 3H, NMe); 6.85 (d, 2 HAr); 7.05 (m, 2 HAr); 7.13 (d, 2 HAr); 7.51 (d, 1 HAr).

LC/MS Gradient 1: Rt: 4.55 min; 336− (M−H)−

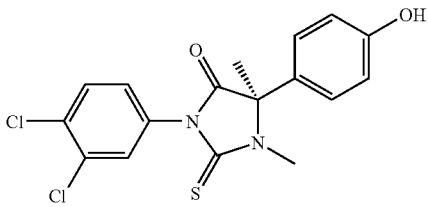

Example 156-4

(R)-1-(3,4-dichlorophenyl)-3,4-dimethyl-4-(4-hydroxyphenyl)-2-thioxoimidazolidin-5-one 1 mL of boron trifluoride/dimethylsulphide complex is added to a solution of 0.4 g of (R)-1-(3,4-dichlorophenyl)-3,4-dimethyl-4-(4-methoxyphenyl)-2-thioxoimidazolidin-5-one in 30 mL of dichloromethane. The mixture is stirred at AT for 24 hours and poured into a saturated aqueous sodium bicarbonate solution and extracted with ethyl acetate. The organic layer is dried over magnesium sulphate, filtered and evaporated. The crude product is purified by crystallisation in a mixture of dichloromethane/methanol/ether/pentane and then crystallised again in dichloromethane. 0.27 g of white crystals are obtained (Yd=71%).

[α]D=+34.8° (c=1%, MeOH).

TLC: Fr=0.30 (70/30 heptane/ethyl acetate).

1H-NMR (CDCl3): δ 2.00 (s, 3H, Me); 3.18 (s, 3H, NMe); 6.97 (d, 2 HAr); 7.10 (d, 2 HAr); 7.21 (dd, 1 HAr); 7.45 (sl, 1 HAr); 7.53 (d, 1 HAr).

LC/MS Gradient 1: Rt: 5.76 min; 381/383+ (MH)+; 379/381− (M−H)−

Example 157

4-[1,3-dioxo-7-methoxy-9b-methyl-1,2,3,9β-tetrahydro-5H-imidazo[5,1-a]isoindol-2-yl]-2-trifluoromethylbenzonitrile

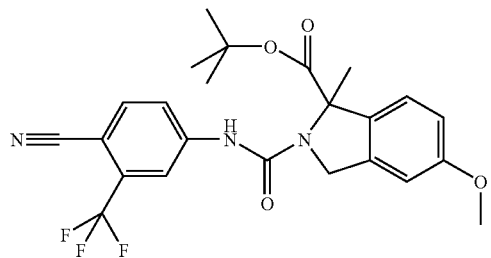

Stage 1

1,1-dimethylethyl 2,3-dihydro-5-methoxy-1-methyl-2-[[(4-cyano-3-trifluoromethylphenyl)-amino]carbonyl]-1H-isoindolecarboxylate 1.42 mL of 0.5 M 4-cyano-3-trifluoromethylphenyl isocyanate solution in anhydrous THF is added to a solution of 153 mg of 1,1-dimethylethyl 2,3-dihydro-5-methoxy-1-methyl-1H-isoindolecarboxylate in 2.9 ml de THF. After 48 hours at AT, the reaction mixture is evaporated to yield 230 mg of product in solid form (Yd=83%).

¹H-NMR (MeOD): δ 1.25 (s, 9H, tBu); 1.71 (s, 3H, Me); 4.75 and 4.85 (AB, J=13 Hz, 2H, CH₂N); 3.7 (s, 3H, OMe); 6.82 (m, 2H$_{Ar}$); 7.1 (d, 1H$_{Ar}$); 7.78 (d, 1H$_{Ar}$); 7.87 (dl, 1H$_{Ar}$); 8.1 (sl, 1H$_{Ar}$).

LC/MS Gradient 1: Rt: 4.14 min; 420+ (MH−CH₂═CMe₂)+; 476+ (MH)+

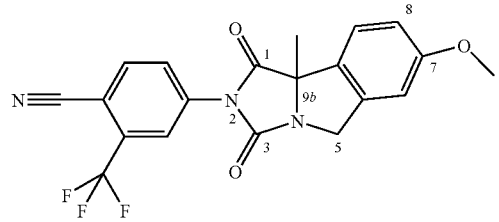

Stage 2

4-[1,3-dioxo-7-methoxy-9b-methyl-1,2,3,9b-tetrahydro-5H-imidazo[5,1-a]isoindol-2-yl]-2-trifluoromethylbenzonitrile 1.9 mL of trifluoroacetic acid are added to a solution of 185 mg of 1,1-dimethylethyl 2,3-dihydro-5-methoxy-1-methyl-2-[[(4-cyano-3-trifluoromethylphenyl)amino]carbonyl]-1H-isoindolecarboxylate in 3.9 mL of dichloromethane at ambient temperature, under nitrogen. After reacting for 3 hours, the reaction mixture is treated with water, extracted with ethyl acetate and concentrated. The residue is taken up by 3.9 mL of pyridine. 84 μl of thionyl chloride are added thereto at 0° C. and the mixture is stirred at ambient temperature under nitrogen for 36 hours. The reaction mixture is treated with a 2 N aqueous hydrochloric acid solution and extracted with ethyl acetate. After drying over sodium sulphate and evaporation to dryness, 160 mg of product are obtained (quantitative Yd).

TLC: Fr=0.8 (ethyl acetate).

¹H-NMR (CDCl₃): 1.8 (s, 3H, Me); 3.85 (s, 3H, OMe); 4.52 and 5.05 (AB, J=14 Hz, 2H, CH₂N); 6.82 (s, 1H$_{Ar}$); 6.92 (dl, 1H$_{Ar}$); 7.5 (d, 1H$_{Ar}$); 7.95 (m, 2H$_{Ar}$); 8.1 (s, 1H$_{Ar}$).

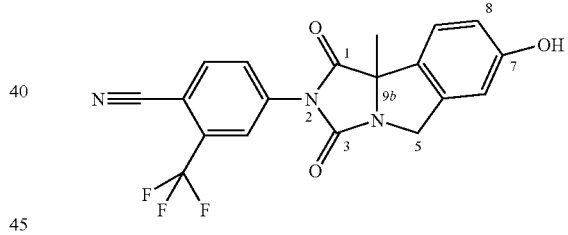

Example 158

4-[1,3-dioxo-7-hydroxy-9b-methyl-1,2,3,9b-tetrahydro-5H-imidazo[5,1-a]isoindol-2-yl]-2-trifluoromethylbenzonitrile 0.41 mL of boron trifluoride/dimethyl sulphide complex is added to a solution of 157 mg of 4-[1,3-dioxo-7-methoxy-9b-methyl-1,2,3,9b-tetrahydro-5H-imidazo[5,1-a]isoindol-2-yl]-2-trifluoromethylbenzonitrile in 3.9 mL of dichloromethane at ambient temperature, under nitrogen. After 48 hours of stirring, the reaction mixture is treated with a saturated aqueous sodium bicarbonate solution and extracted with ethyl acetate. The organic phase is washed with a saturated aqueous sodium chloride solution, dried over sodium sulphate and evaporated. The residue is purified over a silica column with (30/70) ethyl acetate/heptane. A white foam is obtained and is recrystallised in isopropyl ether to yield 150 mg of a white solid (quantitative Yd).

TLC: Fr=0.2 (30/70 ethyl acetate/heptane).

¹H-NMR (CDCl₃): 1.8 (s, 3H, Me); 4.5 and 5.05 (AB, J=14 Hz, 2H, CH₂N); 6.8 (s, 1H$_{Ar}$); 6.85 (dl, 1H$_{Ar}$); 7.42 (d, 1H$_{Ar}$); 7.95 (m, 2H$_{Ar}$); 8.1 (s, 1H$_{Ar}$).
LC/MS Gradient 1: Rt: 3.69 min; 386⁻ (M–H)⁻

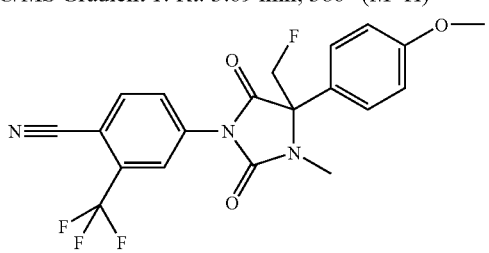

Example 159

4-[4-fluoromethyl-4-(4-methoxyphenyl)-3-methyl-2,5-dioxoimidazolidin-1-yl]-2-trifluoromethylbenzonitrile 107 mg of sodium hydride, 50% in oil, are added to a mixture of 0.7 g of 4-[4-fluoromethyl-4-(4-methoxyphenyl)-2,5-dioxoimidazolidin-1-yl]-2-trifluoromethylbenzonitrile and 1.07 mL of methyl iodide in 17 mL of anhydrous DMF at 0° C. under nitrogen. After 1 hour 30 at 0° C., the reaction mixture is treated with a saturated aqueous sodium bicarbonate solution. After extraction with ethyl acetate and drying over sodium sulphate, the solution is evaporated to dryness. 807 mg of product in the form of an orangey oil are obtained (quantitative Yd).
TLC: Fr=0.14 (70/30 heptane/ethyl acetate).
1H-NMR (MeOD): δ 3.04 (s, 3H, NMe); 3.83 (s, 3H, OMe); 5.15 and 5.41 (2dd, J=13 and 45 Hz, 2H, CH2F); 7.06 (d, 2 HAr); 7.36 (d, 2 HAr); 8.06 and 8.13 (AB, 2 HAr); 8.19 (s, 1 HAr).
LC/MS Gradient 1: Rt: 3.88 min; 418– (M–H)–

Example 159-1

4-[2,5-dioxo-4-(4-methoxyphenyl)-3-methyl-4-(2-propynyl)imidazolidin-1-yl]-2-trifluoromethylbenzonitrile Following the procedure of Example 159, a solution of 380 mg of 4-[2,5-dioxo-4-(4-methoxyphenyl)-4-(2-propynyl) imidazolidin-1-yl]-2-trifluoromethylbenzonitrile in 9 mL of DMF is treated to produce 580 mg of crude product which is purified by chromatography over silica while eluting with (90/10 then 85/15) heptane/ethyl acetate mixture. 320 mg of product are obtained in the form of a white solid (Yd=81%).
¹H-NMR (CDCl₃): δ 2.18 (s, 1H, CH); 3.00 and 3.52 (2d, 2H, CH₂); 3.05 (s, 3H, NMe); 3.85 (s, 3H, OMe); 7.00 (d, 2H$_{Ar}$); 7.28 (d, 2H$_{Ar}$); 7.95 (AB, 2H$_{Ar}$); 8.12 (s, 1H$_{Ar}$).

Examples 160 to 171

The procedure of Example 159 is used to prepare the following products:

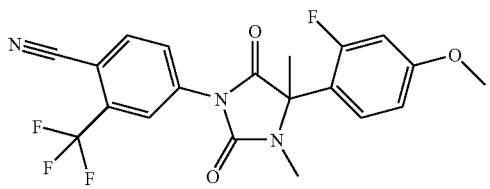

Example 160

4-[3,4-dimethyl-2,5-dioxo-4-(2-fluoro-4-methoxyphenyl)-imidazolidin-1-yl]-2-trifluoromethylbenzonitrile Yd=70%

1H-NMR (MeOD): δ 1.93 (s, 3H, Me); 2.75 (s, 3H, NMe); 3.84 (s, 3H, OMe); 6.80 (dd, 1 HAr); 6.88 (dd, 1 HAr); 7.56 (t, 1 HAr); 8.06 (m, 1 HAr); 8.13 (m, 2 HAr).
LC/MS Gradient 1: Rt: 3.87 min; 433+ (MH+CH3CN)+

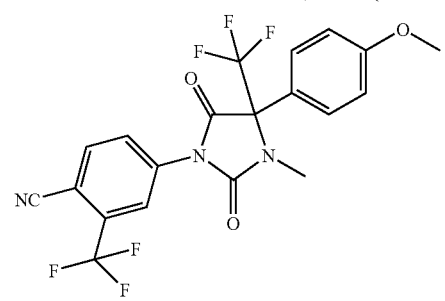

Example 161

4-[2,5-dioxo-4-(4-methoxyphenyl)-3-methyl-4-trifluoromethylimidazolidin-1-yl]-2-trifluoromethylbenzonitrile Yd=53%

1H-NMR (CDCl3): δ 3.00 (s, 1H, NMe); 3.78 (s, 3H, OMe); 6.95 (d, 2 HAr); 7.32 (d, 2 HAr); 7.88 (s, 2 HAr); 8.02 (s, 1 HAr).

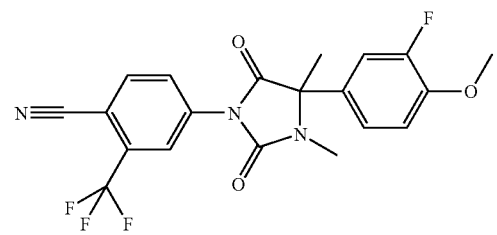

Example 162

4-[3,4-dimethyl-2,5-dioxo-4-(3-fluoro-4-methoxyphenyl)imidazolidin-1-yl]-2-trifluoromethylbenzonitrile Yd=94%
1H-NMR (MeOD): δ 1.96 (s, 3H, Me); 2.93 (s, 3H, NMe); 3.92 (s, 3H, OMe); 7.23 (m, 3 HAr); 8.10 (m, 2 HAr); 8.23 (s, 1 HAr).

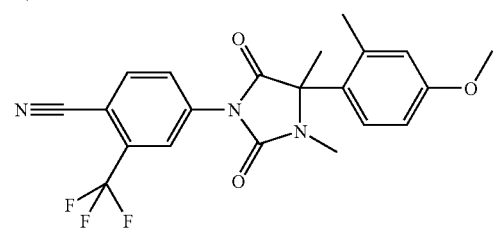

Example 163

4-[3,4-dimethyl-2,5-dioxo-4-(4-methoxy-2-methylphenyl)imidazolidin-1-yl]-2-trifluoromethylbenzonitrile quantitative Yd 1H-NMR (MeOD+a drop of DMSO D6): δ 2.07 (s, 3H, Me); 2.23 (s, 3H, PhMe); 2.80 (s, 3H, NMe); 3.89 (s, 3H, OMe); 6.90 (s, 1 HAr); 6.98 (d, 1 HAr); 7.63 (d, 1 HAr); 8.23 (m, 2 HAr); 8.30 (s, 1 HAr).

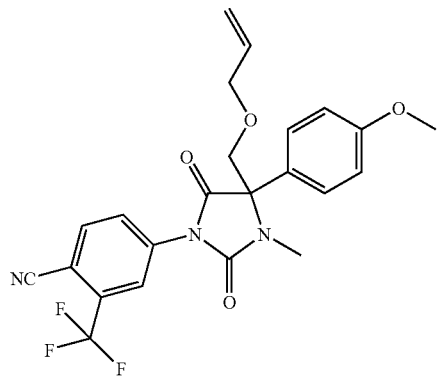

Example 164

4-[2,5-dioxo-4-(4-methoxyphenyl)-3-methyl-4-[(2-propenyloxy)methyl]imidazolidin-1-yl]-2-trifluoromethylbenzonitrile Yd=52%

1H-NMR (MeOD+a drop of DMSO D6): δ 3.01 (s, 1H, NMe); 3.85 (s, 3H, OMe); 3.93 and 4.37 (2d, 2H, CH2O); 4.10 (d, 2H, OCH2CH=); 5.25 (d, 1H, CH2=CH); 5.29 (d, 1H, CH2=CH); 5.85 (m, 1H, CH2=CH); 6.98 (d, 2 HAr); 7.28 (d, 2 HAr); 7.95 (m, 2 HAr); 8.11 (s, 1 HAr).
LC/MS Gradient 1: Rt: 3.81 min; 501+ (MH+CH3CN)+

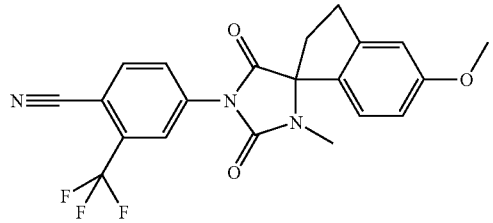

Example 165

4-[2',3'-dihydro-2,5-dioxo-5'-methoxy-3-methylspiro(imidazolidin-4,1'(1H)inden)-1-yl]-2-trifluoromethylbenzonitrile quantitative Yd LC/MS Gradient 1: Rt: 6.09 min; 416+ (MH)+; 457+ (MH+CH3CN)+

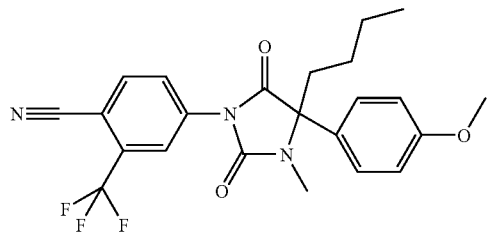

Example 166

4-[4-butyl-2,5-dioxo-4-(4-methoxyphenyl)-3-methylimidazolidin-1-yl]-2-trifluoromethyl-benzonitrile Yd=56%

LC/MS Gradient 1: Rt: 5.4 min; 487+ (MH+CH3CN)+

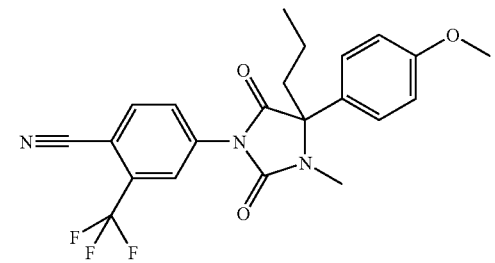

Example 166-1

4-[2,5-dioxo-4-(4-methoxyphenyl)-3-methyl-4-propylimidazolidin-1-yl]-2-trifluoromethylbenzonitrile Following the procedure of Example 159, a solution of 380 mg of 4-[2,5-dioxo-4-(4-methoxyphenyl)-4-(2-propynyl)imidazolidin-1-yl]-2-trifluoromethylbenzonitrile in 2 mL of DMF is treated to produce crude product which is purified by chromatography over silica while eluting with (90/10 then 85/15) heptane/ethyl acetate mixture. 307 mg of product are obtained in the form of a white solid (Yd=71%).

1H-NMR (CDCl3): δ 1.08 (t, 3H, Me); 1.35 (m, 2H, CH2); 2.05 and 2.6 (2m, 2H, CH2); 2.92 (s, 3H, NMe); 3.82 (s, 3H, OMe); 6.98 (d, 2 HAr); 7.28 (d, 2 HAr); 7.91 (d, 1 HAr); 8.0 (dd, 1 HAr); 8.12 (d, 1 HAr).
LC/MS Gradient 1: Rt: 5.5 min; 473+ (M+CH3CN)+

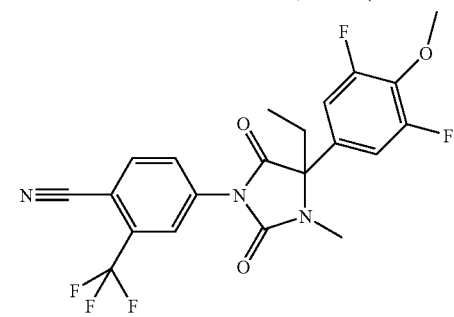

Example 167

4-[4-(3,5-difluoro-4-methoxyphenyl)-2,5-dioxo-4-ethyl-3-methylimidazolidin-1-yl]-2-trifluoromethyl-benzonitrile quantitative Yd 1H-NMR (CDCl3): δ 1.0 (t, 3H, Me); 2.08 and 2.65 (2m, 2H, CH2); 3.0 (s, 3H, NMe); 4.05 (s, 3H, OMe); 6.94 (m, 2 HAr); 7.91 and 7.98 (AB, 2 HAr); 8.1 (s, 1 HAr).

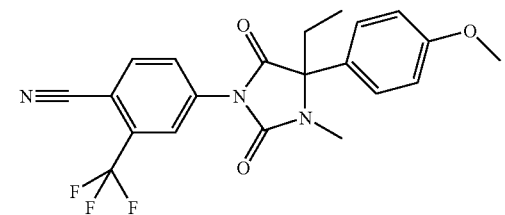

Example 168

4-[2,5-dioxo-4-ethyl-4-(4-methoxyphenyl)-3-methylimidazolidin-1-yl]-2-trifluoromethylbenzonitrile Yd=86%

1H-NMR (MeOD): δ 0.9 (t, 3H, Me); 2.28 and 2.66 (2m, 2H, CH2); 2.77 (s, 3H, NMe); 3.83 (s, 3H, OMe); 7.03 (d, 2 HAr); 7.38 (d, 2 HAr); 8.11 (m, 2 HAr); 8.18 (s, 1 HAr).

LC/MS Gradient 1: Rt: 5.63 min; 459+ (MH+CH3CN)+

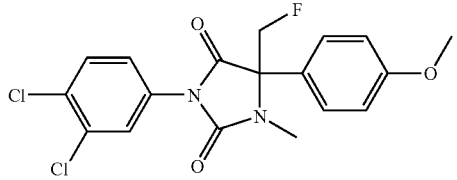

Example 169

1-(3,4-dichlorophenyl)-4-fluoromethyl-4-(4-methoxyphenyl)-3-methylimidazolidine-2,5-dione Yd=67%

1H-NMR (CDCl3): δ 3.08 (s, 3H, NMe); 3.84 (s, 3H, OMe); 4.85 and 5.32 (2dd, J=45 and 12 Hz, 2H, CH2F); 7.06 (d, 2 HAr); 7.41 (d, 2 HAr); 7.52 (d, 1 HAr); 7.75 (m, 2 HAr).

LC/MS Gradient 1: Rt: 5.24 min; 397/399+ (MH)+

Example 170

4-[4-(3-chloro-4-methoxyphenyl)-3,4-dimethyl-2,5-dioxoimidazolidin-1-yl]-2-trifluoromethylbenzonitrile Yd=82%

1H-NMR (CDCl3): δ 1.94 (s, 3H, Me); 2.98 (s, 3H, NMe); 3.95 (s, 3H, OMe); 6.98 and 7.01 (2d 15/85, 1 HAr); 7.22 (dl, 1 HAr); 7.36 and 7.52 (2sl 85/15, 1 HAr); 7.93 and 8.01 (AB, 2 HAr); 8.17 (s, 1 HAr).

LC/MS Gradient 1: Rt: 5.64 min; 456/458+ (MH+H2O)+

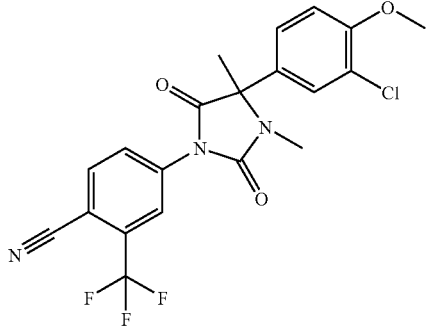

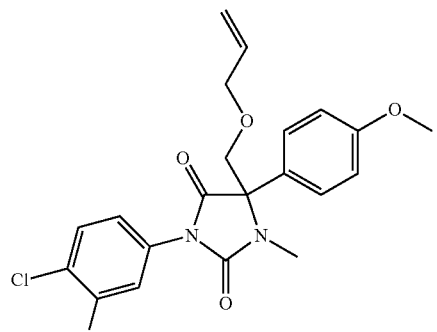

Example 171

1-(3,4-dichlorophenyl)-4-(4-methoxyphenyl)-3-methyl-4-[(2-propenyloxy)methyl]-imidazolidine-2,5-dione Yd=70%

1H-NMR (CDCl3): δ 3.0 (s, 3H, NMe); 3.83 (s, 3H, OMe); 3.92 and 4.32 (2d, 2H, CH2O); 4.10 (d, 2H, OCH2CH=); 5.23 (d, 1H, CH2=CH); 5.29 (d, 1H, CH2=CH); 5.87 (m, 1H, CH2=CH); 6.97 (d, 2 HAr); 7.28 (d, 2 HAr); 7.35 (d, 1 HAr); 7.52 (d, 1 HAr); 7.62 (s, 1 HAr).

LC/MS Gradient 1: Rt: 4.01 min; 476/478+ (MH+CH3CN)+

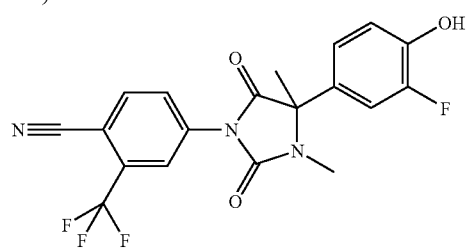

Example 172

4-[4-(3-fluoro-4-hydroxyphenyl)-3,4-dimethyl-2,5-dioxoimidazolidin-1-yl]-2-trifluoromethylbenzonitrile 404 mg of 4-[3,4-dimethyl-2,5-dioxo-4-(3-fluoro-4-methoxyphenyl)imidazolidin-1-yl]-2-trifluoromethylbenzonitrile are dissolved in 9 mL of dichloromethane at ambient temperature, under nitrogen. 750 µL of boron tribromide are added at −78° C. The mixture is stirred at ambient temperature for 18 hours (orange solution). As the reaction is incomplete, 850 µL of boron tribromide are added and the mixture is stirred at AT for 3 hours, then the crude reaction product is poured over iced water. After extraction with ethyl acetate then drying over sodium sulphate and concentration, an amorphous white foam is obtained (360 mg). The residue is purified over a silica column with 50/50 heptane/ethyl acetate. After evaporation and drying under vacuum, 283 mg of product are obtained (amorphous white foam, Yd=79%) are obtained.

TLC: Fr=0.31 (50/50 heptane/ethyl acetate).

1H-NMR (MeOD): δ 1.94 (s, 3H, Me); 2.92 (s, 3H, NMe); 7.04 (m, 2 HAr); 7.21 (d, 1 HAr); 8.10 (m, 2 HAr); 8.23 (s, 1 HAr).
LC/MS Gradient 1: Rt: 5.02 min; 406− (M−H)−

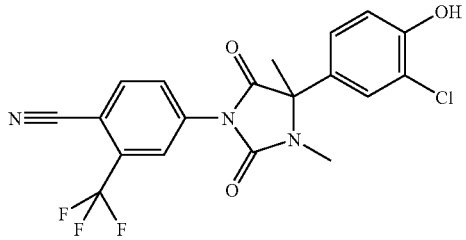

Example 173

4-[4-(3-chloro-4-hydroxyphenyl)-3,4-dimethyl-2,5-dioxoimidazolidin-1-yl]-2-trifluoromethylbenzonitrile 456 mg of 4-[4-(3-chloro-4-methoxyphenyl)-3,4-dimethyl-2,5-dioxoimidazolidin-1-yl]-2-trifluoromethylbenzonitrile are dissolved in 5 mL of dichloromethane at ambient temperature, under nitrogen. 9.15 mL of 1 N boron tribromide solution in dichloromethane are progressively added at −78° C. The mixture is stirred at ambient temperature for 18 hours (orange solution). The crude reaction product is poured over iced water. After extraction with dichloromethane then drying over sodium sulphate and concentration, an amorphous light brown foam is obtained (462 mg). The residue is purified over a silica column with 60/40 heptane/ethyl acetate to yield 290 mg of product (white solid, Yd=66%); Mp=161.1° C.
TLC: Fr=0.40 (30/70 heptane/ethyl acetate).
1H-NMR (CDCl3): δ 1.94 (s, 3H, Me); 2.97 (s, 3H, NMe); 5.74 (s, 1H, OH); 7.11 (d, 1 HAr); 7.19 (d, 1 HAr); 7.33 and 7.47 (2 sl 88/12, 1 HAr); 7.92 (d, 1 HAr); 8.01 (d, 1 HAr); 8.16 (s, 1 HAr).
LC/MS Gradient 1: Rt: 4.94 min; 422/424− (M−H)−

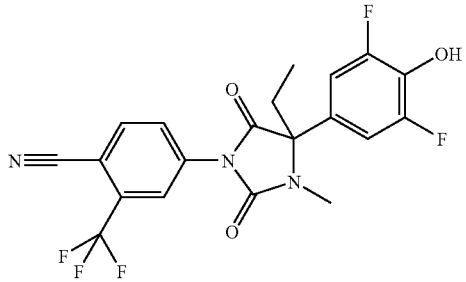

Example 174

4-[4-(3,5-difluoro-4-hydroxyphenyl)-2,5-dioxo-4-ethyl-3-methylimidazolidin-1-yl]-2-trifluoromethylbenzonitrile 0.27 g of 4-[4-(3,5-difluoro-4-methoxyphenyl)-2,5-dioxo-4-ethyl-3-methylimidazolidin-1-yl]-2-trifluoromethylbenzonitrile is dissolved in 4 mL of dichloromethane at ambient temperature, under nitrogen. 1 mL of boron tribromide is added at −78° C. and the mixture is stirred for 48 hours at AT. The mixture is poured over a saturated aqueous sodium bicarbonate solution, then extracted with dichloromethane. After drying over sodium sulphate and concentration, the residue is purified over a silica column with 80/20 heptane/ethyl acetate in order to obtain 250 mg of product after drying under vacuum (white solid, quantitative Yd).
TLC: Fr=0.45 (50/50 heptane/ethyl acetate).
1H-NMR (CDCl3): δ 1.0 (t, 3H, CH3CH2); 2.08 and 2.65 (2m, 2H, CH2); 2.97 (s, 3H, NMe); 6.94 (m, 2 HAr); 7.91 and 7.98 (AB, 2 HAr); 8.1 (s, 1 HAr).

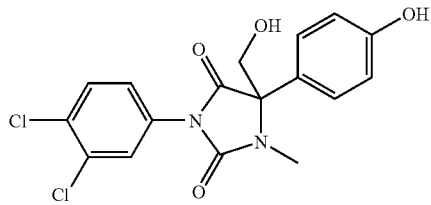

Example 175

1-(3,4-dichlorophenyl)-4-hydroxymethyl-4-(4-hydroxyphenyl)-3-methylimidazolidine-2,5-dione 0.44 g of 1-(3,4-dichlorophenyl)-4-(4-methoxyphenyl)-3-methyl-4-[(2-propenyloxy)methyl]imidazolidine-2,5-dione are dissolved in 5 mL of dichloromethane at ambient temperature, under nitrogen. 1 mL of boron trifluoride/dimethyl sulphide complex is added and the mixture is stirred for 18 hours at ambient temperature. The reaction mixture is poured into a saturated aqueous sodium bicarbonate solution. After extraction with dichloromethane then drying over sodium sulphate and concentration, the mixture is purified over a silica column with 100/0 then 85/5 dichloromethane/ethyl acetate to yield 300 mg of product in the form of a crystalline white solid after drying under vacuum (Yd=78%); Mp=215.6° C.
TLC: Fr=0.3 (50/50 heptane/ethyl acetate).
1H-NMR (MeOD): δ 2.92 (s, 3H, NMe); 4.12 and 4.49 (2d, 2H, CH2O); 6.87 (d, 2 HAr); 7.20 (d, 2 HAr); 7.42 (d, 1 HAr); 7.64 (d, 1 HAr); 7.70 (s, 1 HAr).
LC/MS Gradient 1: Rt: 2.64 min; 379− (M−H)−; 381+ (MH)+ and 422+ (MH+CH3CN)+

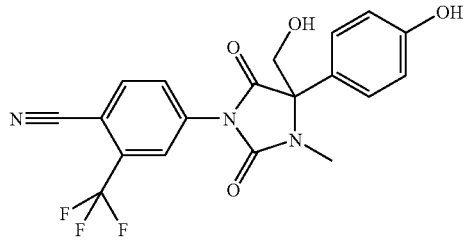

Example 176

4-[2,5-dioxo-4-hydroxymethyl-4-(4-hydroxyphenyl)-3-methyl-imidazolidin-1-yl]-2-trifluoromethylbenzonitrile 300 mg of 4-[2,5-dioxo-4-(4-methoxyphenyl)-3-methyl-4-[(2-propenyloxy)methyl]imidazolidin-1-yl]-2-trifluoromethylbenzonitrile are dissolved in 5 mL of dichloromethane, under argon. 1 mL of boron trifluoride/dimethyl sulphide complex is added and the mixture is stirred for 18 hours at AT, then treated with a saturated aqueous sodium bicarbonate solution. After extraction with dichloromethane, washing with a saturated aqueous sodium chloride solution, drying over sodium sulphate, the product is purified by chromatography over silica by eluting with dichloromethane then with a 95/5 dichloromethane/ethyl acetate mixture. 230 mg of expected product crystallised in isopropyl ether are obtained (Yd=75%).

TLC: Fr=0.2 (50/50 heptane/ethyl acetate).

1H-NMR (MeOD): δ 2.97 (s, 3H, NMe); 4.13 and 4.52 (2d, 2H, CH2O); 6.87 (d, 2 HAr); 7.22 (d, 2 HAr); 8.09 (m, 2 HAr); 8.20 (s, 1 HAr).

LC/MS Gradient 1: Rt: 2.76 min; 404– (M–H)–

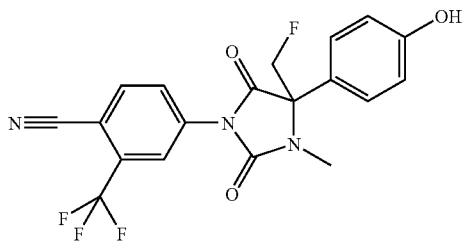

Example 177

4-[2,5-dioxo-4-fluoromethyl-4-(4-hydroxyphenyl)-3-methylimidazolidin-1-yl]-2-trifluoromethylbenzonitrile 1.81 mL of boron trifluoride/dimethyl sulphide complex are added to a solution of 807 mg of 4-[4-fluoromethyl-4-(4-methoxyphenyl)-3-methyl-2,5-dioxoimidazolidin-1-yl]-2-trifluoromethylbenzonitrile in 17 mL of dichloromethane. After 24 hours under nitrogen, the mixture is treated with a saturated aqueous sodium bicarbonate solution, extracted with dichloromethane, dried over sodium sulphate, and the solvent is evaporated. The residue is purified over a silica column with 100/0 to 60/40 heptane/ethyl acetate to yield 604 mg of product (beige powder, Yd=86% for 2 stages).

TLC: Fr=0.32 (50/50 heptane/ethyl acetate).

1H-NMR (MeOD): δ 3.02 (s, 3H, NMe); 5.13 and 5.38 (2dd, J=45 and 13 Hz, 2H, CH2F); 6.90 (d, 2 HAr); 7.24 (d, 2 HAr); 8.07 and 8.12 (AB, 2 HAr); 8.19 (s, 1 HAr).

LC/MS Gradient 1: Rt: 3.64 min; 406– (M–H)–

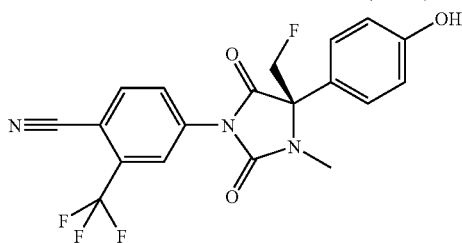

Example 177-1

(S)-4-[4-fluoromethyl-4-(4-hydroxyphenyl)-3-methyl-2,5-dioxoimidazolidin-1-yl]-2-trifluoromethylbenzonitrile The two enantiomers of 4-[4-fluoromethyl-4-(4-hydroxyphenyl)-3-methyl-2,5-dioxoimidazolidin-1-yl]-2-trifluoromethylbenzonitrile are separated by chromatography of a 3 g sample of racemic mixture on Chiralpak AD while eluting with a 80/10/10 heptane/ethanol/methanol mixture. The (S) enantiomer is eluted first, 1.3 g of 96% pure compound is obtained as an amorphous, slightly yellow solid.

[α]D=+26.1° (c=1%, CHCl3).

TLC: Fr=0.30 (50/50 heptane/ethyl acetate).

HPLC (Chiralpak AD 10 μm, column 250×4.6 mm, heptane/ethanol/methanol 80/10/10, flow rate 1 ml/min): Rt: 13.68 min.

1H-NMR (MeOD): δ 3.02 (s, 3H, NMe); 5.13 and 5.38 (2dd, J=45 and 13 Hz, 2H, CH2F); 6.90 (d, 2 HAr); 7.24 (d, 2 HAr); 8.07 and 8.12 (AB, 2 HAr); 8.19 (s, 1 HAr).

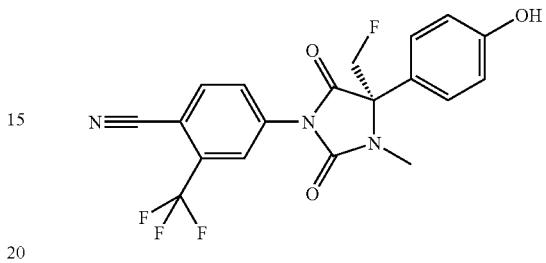

Example 177-2

(R)-4-[4-fluoromethyl-4-(4-hydroxyphenyl)-3-methyl-2,5-dioxoimidazolidin-1-yl]-2-trifluoromethylbenzonitrile Using the separation conditions of 177-1 the (R) enantiomer is eluted second, 0.99 g of 99% pure compound is obtained as an amorphous, white solid.

[α]D=–27.6° (c=1%, CHCl3).

TLC: Fr=0.30 (50/50 heptane/ethyl acetate).

HPLC (Chiralpak AD 10 μm, column 250×4.6 mm, heptane/ethanol/methanol 80/10/10, flow rate 1 ml/min): Rt: 18.31 min.

1H-NMR (MeOD): δ 3.02 (s, 3H, NMe); 5.13 and 5.38 (2dd, J=45 and 13 Hz, 2H, CH2F); 6.90 (d, 2 HAr); 7.24 (d, 2 HAr); 8.07 and 8.12 (AB, 2 HAr); 8.19 (s, 1 HAr).

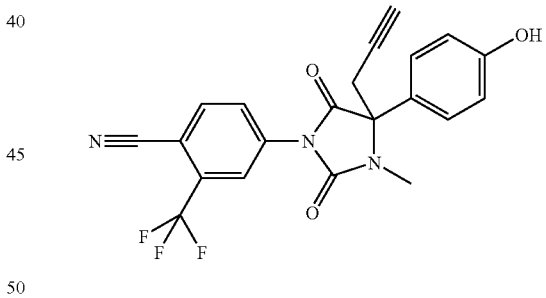

Example 177-3

4-[2,5-dioxo-4-(4-hydroxyphenyl)-3-methyl-4-(2-propynyl)imidazolidin-1-yl]-2-trifluoromethylbenzonitrile 1.3 mL of boron trifluoride/dimethyl sulphide complex is added to a solution of 284 mg of 4-[2,5-dioxo-4-(4-methoxyphenyl)-3-methyl-4-(2-propynyl)imidazolidin-1-yl]-2-trifluoromethylbenzonitrile in 7.5 mL of dichloromethane. After 19 hours under nitrogen, the mixture is treated with a saturated aqueous sodium bicarbonate solution, extracted with dichloromethane, dried over sodium sulphate, and the solvent is evaporated. The residue is purified over a silica column with 100/0 to 80/20 heptane/ethyl acetate to yield 200 mg of product as a white solid foam (Yd=72%); Mp=122° C.

TLC: Fr=0.24 (50/50 heptane/ethyl acetate).
1H-NMR (CDCl3): δ 2.08 (s, 1H, ≡CH); 2.92 and 3.42 (2d, 2H, CH2); 2.95 (s, 3H, NMe); 5.10 (s, 1H, OH); 6.83 (d, 2 HAr); 7.12 (d, 2 HAr); 7.86 (AB, 2 HAr); 8.03 (s, 1 HAr).
LC/MS Gradient 1: Rt: 6.95 min; 412− (M−H)−

Examples 178 to 184

The procedure of Example 177 is used to prepare the following products from the corresponding methoxylated derivatives:

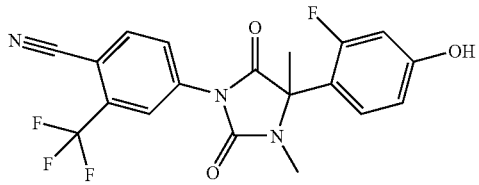

Example 178

4-[3,4-dimethyl-2,5-dioxo-4-(2-fluoro-4-hydroxyphenyl)imidazolidin-1-yl]-2-trifluoromethylbenzonitrile Yd=83%
1H-NMR (DMSO D6): δ 1.99 (s, 3H, Me); 2.68 (s, 3H, NMe); 6.62 (d, 1 HAr); 6.71 (d, 1 HAr); 7.46 (t, 1 HAr); 8.02 (d, 1 HAr); 8.14 (s, 1 HAr); 8.35 (d, 1 HAr); 10.35 (s, 1H, OH).
LC/MS Gradient 1: Rt:=3.70 min; 406− (M−H)−

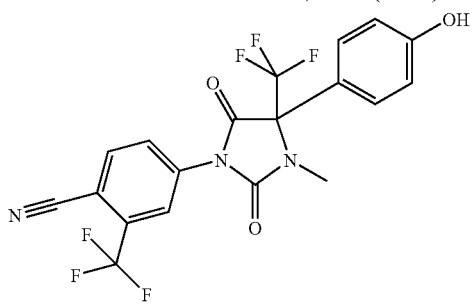

Example 179

4-[2,5-dioxo-4-(4-hydroxyphenyl)-3-methyl-4-trifluoromethylimidazolidin-1-yl]-2-trifluoromethylbenzonitrile Yd=77%

1H-NMR (MeOD): δ 3.00 (s, 1H, NMe); 6.95 (d, 2 HAr); 7.42 (d, 2 HAr); 8.07 (d, 2 HAr); 8.17 (m, 2 HAr).
LC/MS Gradient 1: Rt:=3.60 min; 442− (M−H)−

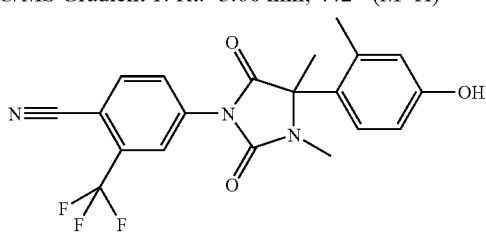

Example 180

4-[3,4-dimethyl-2,5-dioxo-4-(4-hydroxy-2-methylphenyl)imidazolidin-1-yl]-2-trifluoromethylbenzonitrile Yd=79%
1H-NMR (MeOD): δ 1.98 (s, 3H, Me); 2.12 (s, 3H, PhMe); 2.74 (s, 3H, NMe); 6.71 (s, 1 HAr); 6.75 (d, 1 HAr); 7.44 (d, 1 HAr); 8.14 (m, 2 HAr); 8.23 (s, 1 HAr).
LC/MS Gradient 1: Rt:=5.16 min; 402− (M−H)−

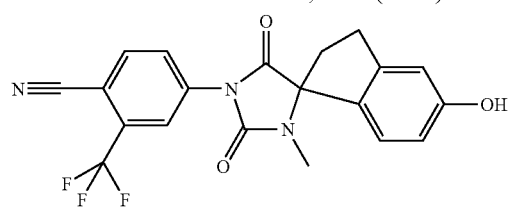

Example 181

4-[2',3'-dihydro-2,5-dioxo-5'-hydroxy-3-methylspiro(imidazolidin-4,1'(1H)inden)-1-yl]-2-trifluoromethylbenzonitrile Yd=70%

1H-NMR (CDCl3): δ 2.45 and 2.72 (2m, 2H, CH2Ph); 2.9 (s, 3H, NMe); 3.14 and 3.27 (2m, 2H, CH2N); 6.77 (d, 1 HAr); 6.82 (s, 1 HAr); 6.95 (d, 1 HAr); 7.92 (d, 1 HAr); 8.05 (d, 1 HAr); 8.2 (s, 1H).

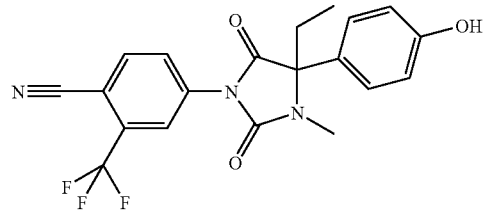

Example 182

4-[4-butyl-2,5-dioxo-4-(4-hydroxyphenyl)-3-methylimidazolidin-1-yl]-2-trifluoromethyl-benzonitrile quantitative Yd 1H-NMR (CDCl3): δ 0.98 (t, 3H, CH3CH2); 1.35 (m, 4H, CH3CH2CH2); 2.07 and 2.65 (2m, 2H, CH2C); 2.9 (s, 3H, NMe); 6.88 (AB, 2 HAr); 7.2 (AB, 2 HAr); 7.9 (d, 1 HAr); 8.0 (d, 1 HAr); 8.2 (s, 1 HAr).

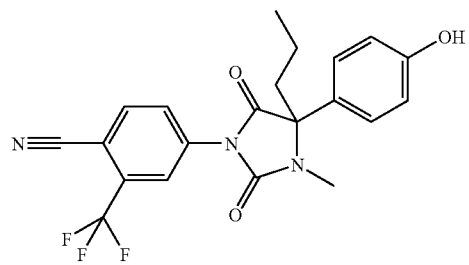

Example 182-1

4-[2,5-dioxo-4-(4-hydroxyphenyl)-3-methyl-4-propylimidazolidin-1-yl]-2-trifluoromethylbenzonitrile Yd=88%

1H-NMR (DMSO D6): δ 1.00 (t, 3H, Me); 1.25 (m, 2H, CH2); 2.15 and 2.4 (2m, 2H, CH2); 2.75 (s, 3H, NMe); 6.82 (d, 2 HAr); 7.27 (d, 2 HAr); 8.05 (dd, 1 HAr); 8.2 (d, 1 HAr); 8.3 (d, 1 HAr); 9.7 (s, 1H, OH).

LC/MS Gradient 1: Rt: 5.3 min; 416– (M–H)–; 835– (2M–H)–

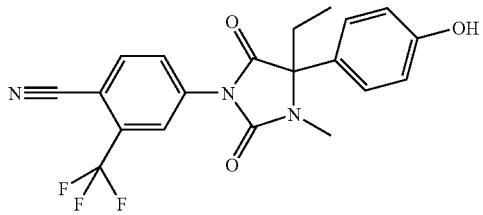

Example 183

4-[2,5-dioxo-4-ethyl-4-(4-hydroxyphenyl)-3-methylimidazolidin-1-yl]-2-trifluoromethylbenzonitrile
Yd=97%

1H-NMR (MeOD): δ 0.98 (t, 3H, CH3CH2); 2.24 and 2.64 (2 m, 2H, CH3CH2); 2.87 (s, 3H, NMe); 6.87 (d, 2 HAr); 7.25 (d, 2 HAr); 8.10 (m, 2 HAr); 8.17 (s, 1 HAr).

LC/MS Gradient 1: Rt:=5.17 min; 402– (M–H)–

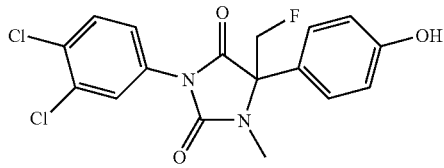

Example 184

1-(3,4-dichlorophenyl)-4-fluoromethyl-4-(4-hydroxyphenyl)-3-methylimidazolidine-2,5-dione quantitative Yd; Mp=167.2° C.

1H-NMR (MeOD): δ 3.0 (s, 3H, NMe); 5.1 and 5.33 (2dd, J=46 and 10 Hz, 2H, CH2F); 6.89 (d, 2 HAr); 7.41 (d, 2 HAr); 7.21 (d, 1 HAr); 7.65 (m, 2 HAr).

LC/MS Gradient 1: Rt:=4.50 min; 383/385+ (MH)+

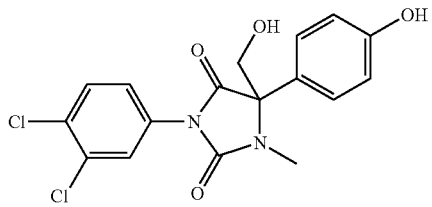

Example 190

1-(3,4-dichlorophenyl)-4-hydroxymethyl-4-(4-hydroxyphenyl)-3-methylimidazolidine-2,5-dione 27 mg of 4-[1-(3,4-dichlorophenyl)-2,5-dioxo-4-hydroxymethyl-3-methyl-imidazolidin-4-yl]phenyl and 1,1-dimethylethyl carbonate are dissolved in 1 mL of a (50/50) trifluoroacetic acid/dichloromethane mixture. The mixture is stirred for 18 hours at ambient temperature, then treated with water and extracted with ethyl acetate. The mixture is dried over magnesium sulphate, then concentrated and purified over a silica column with 40/60 ethyl acetate/heptane to yield 19 mg of product (Yd=90%).

TLC: Fr=0.17 (60/40 heptane/ethyl acetate).

1H-NMR (MeOD): δ 2.85 (s, 3H, NMe); 3.9 and 4.4 (2d, J=10 Hz, 2H, CH2OH); 6.75 and 7.0 (AB, 4 HAr); 7.3 (m, 1 HAr); 7.4 (d, 1 HAr); 7.59 (d, 1 HAr).

LC/MS Gradient 1: Rt: 3.24 min; 379/381– (M–H)–

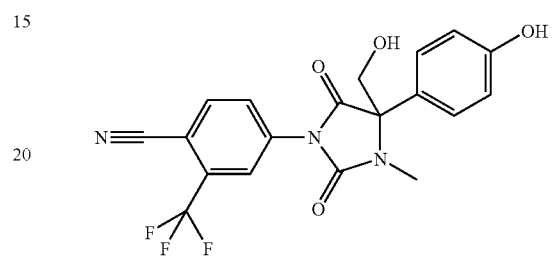

Example 191

4-[2,5-dioxo-4-hydroxymethyl-4-(4-hydroxyphenyl)-3-methylimidazolidin-1-yl]-2-trifluoromethylbenzonitrile The method according to Example 190 is used, starting from 4-[1-(4-cyano-3-trifluorophenyl)-2,5-dioxo-4-hydroxymethyl-3-methylimidazolidin-4-yl]phenyl and 1,1-dimethylethyl carbonate, quantitative Yd.

1H-NMR (MeOD): δ 2.85 (s, 3H, NMe); 4.0 and 4.4 (2d, J=10 Hz, 2H, CH2OH); 6.75 and 7.1 (AB, 4 HAr); 7.9-8.1 (m, 3 HAr).

LC/MS Gradient 1: Rt: 3.29 min; no ionisation

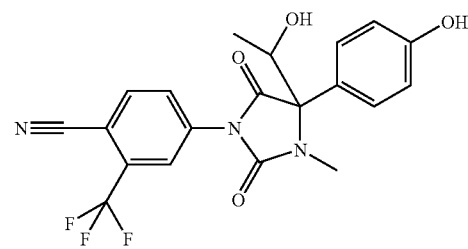

Example 192

4-[2,5-dioxo-4-(1-hydroxyethyl)-4-(4-hydroxyphenyl)-3-methylimidazolidin-1-yl]-2-trifluoromethylbenzonitrile The method according to Example 190 is used, starting from 4-[1-(4-cyano-3-trifluorophenyl)-2,5-dioxo-4-(1-hydroxyethyl)-3-methylimidazolidin-4-yl]phenyl and 1,1-dimethylethyl carbonate.

1H-NMR (CDCl3): Mixture of diastereoisomers. δ 1.38 and 1.42 (2d 4/6, 3H, CH3CH); 3.03 and 3.21 (2s 6/4, 3H, NMe); 4.91 and 4.97 (2m, 1H, CHOH); 5.15 and 5.19 (2s:

6/4, 1H, OH); 6.93 and 6.98 (2d 6/4, 2 HAr); 7.27 and 7.32 (2d 6/4, 2 HAr); 7.85 (m, 2 HAr); 8.10 and 8.13 (2s 4/6, 1HAr).

LC/MS Gradient 1: Rt: 3.39 min; 474– (M–CH3CHOH)–

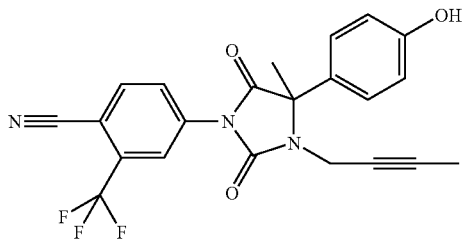

Example 220

4-[3-(2-butynyl)-4-(4-hydroxyphenyl)-4-methyl-2,5-dioxoimidazolidin-1-yl]-2-trifluoromethylbenzonitrile 154 mg of 4-[3-(2-butynyl)-1-(4-cyano-3-trifluoromethylphenyl)-2,5-dioxo-4-methyl-imidazolidin-4-yl]phenyl and 1,1-dimethylethyl carbonate are dissolved in 25 mL of trifluoroacetic acid/dichloromethane mixture (50/50). The mixture is stirred overnight at AT then concentrated and dried under vacuum. 142 mg of product are obtained and purified over a silica column with 70/30 then 60/40 heptane/ethyl acetate. 62 mg of expected product are obtained (white solid; Yd=56%); Mp=172° C.

TLC: Fr=0.35 (50/50 heptane/ethyl acetate).

1H-NMR (CDCl3): δ 1.78 (t, 3H, MeC); 2.08 (s, 3H, Me); 3.45 and 3.70 (2dq, 2H, J=14 and 5 Hz, CH2N); 6.90 (d, 2 HAr); 7.22 (d, 2 HAr); 7.92 (d, 1 HAr); 8.02 (dd, 1 HAr); 8.18 (d, 1 HAr).

LC/MS Gradient 1: Rt: 3.70 min; 426– (M–H)–

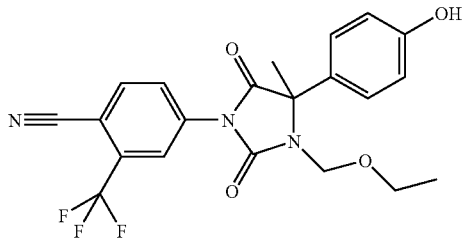

Example 221

4-[3-(ethoxymethyl)-4-(4-hydroxyphenyl)-4-methyl-2,5-dioxoimidazolidin-1-yl]-2-trifluoromethylbenzonitrile 93 mg of 4-[1-(4-cyano-3-trifluoromethylphenyl)-2,5-dioxo-3-(ethoxymethyl)-4-methylimidazolidin-4-yl]phenyl and 1,1-dimethylethyl carbonate are dissolved in 4 mL of a trifluoroacetic acid/dichloromethane mixture (50/50). The mixture is stirred for one night at ambient temperature then concentrated and dried under vacuum. 84 mg of product are obtained and purified over a silica column with 70/30 then 60/40 heptane/ethyl acetate. 10 mg of expected product are obtained (white solid; Yd=9%); Mp=143° C.

TLC: Fr=0.25 (50/50 heptane/ethyl acetate).

1H-NMR (MeOD): δ 1.15 (t, 3H, CH2CH3); 2.02 (s, 3H, Me); 3.60 (q, 2H, CH2CH3); 4.43 and 5.15 (2d, J=12.7 Hz, 2H, NCH2O); 6.86 (d, 2 HAr); 7.47 (d, 2 HAr); 8.11 (m, 2 HAr); 8.22 (s, 1 HAr).

LC/MS Gradient 1: Rt: 3.73 min; 432– (M–H)–

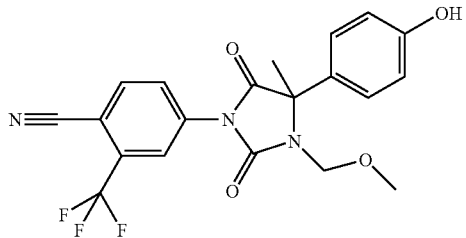

Example 222

4-[4-(4-hydroxyphenyl)-3-methoxymethyl-4-methyl-2,5-dioxoimidazolidin-1-yl]-2-trifluoromethylbenzonitrile 662 mg of 4-[1-(4-cyano-3-trifluoromethylphenyl)-2,5-dioxo-3-(methoxymethyl)-4-methylimidazolidin-4-yl]phenyl and 1,1-dimethylethyl carbonate and 8 mL of dichloromethane are introduced into a flask. 4 mL of trifluoroacetic acid are then added slowly. The mixture is stirred for 2.5 hours at ambient temperature, then neutralised with a saturated aqueous sodium bicarbonate solution, extracted with dichloromethane, dried over sodium sulphate and concentrated. 605 mg of product are obtained and purified over a silica column with 70/30 heptane/ethyl acetate. The product is taken up in isopropyl ether to yield an amorphous white foam (Yd=75%).

The product may be crystallised from a heptane/ethyl acetate mixture; Mp=154.1° C.

TLC: Fr=0.30 (50/50 heptane/ethyl acetate).

1H-NMR (CDCl3): δ 2.03 (s, 3H, Me); 3.43 (s, 3H, OMe); 4.43 and 5.14 (2d, J=12 Hz, 2H, NCH2O); 5.28 (sl, 1H, OH); 6.88 (d, 2 HAr); 7.22 (d, 2 HAr); 7.93 (d, 1 HAr); 8.02 (dl, 1 HAr); 8.16 (sl, 1 HAr).

LC/MS Gradient 1: Rt: 1.21 min; 444– (M–H)–

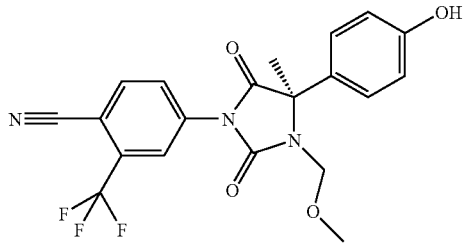

Example 222-1

(R)-4-[2,5-dioxo-4-(4-hydroxyphenyl)-3-methoxymethyl-4-methylimidazolidin-1-yl]-2-trifluoromethylbenzonitrile The method of Example 222 is applied to 1.9 g of (R)-4-[1-(4-cyano-3-trifluoromethylphenyl)-2,5-dioxo-3-methoxymethyl-4-methylimidazolidin-4-yl]phenyl and 1,1-dimethylethyl carbonate to produce 1 g of product as a white solid (Yd=75%); Mp=97° C.

[α]D=–5.2° (c=1%, CHCl3).

1H-NMR (CDCl3): δ 2.03 (s, 3H, Me); 3.43 (s, 3H, OMe); 4.42 and 5.14 (2d, 2H, NCH2O); 5.45 (sl, 1H, OH); 6.88 (d, 2 HAr); 7.21 (d, 2 HAr); 7.93 (d, 1 HAr); 8.02 (dl, 1 HAr); 8.17 (sl, 1 HAr).

LC/MS Gradient 1: Rt: 5.0 min; 418– (M–H)–

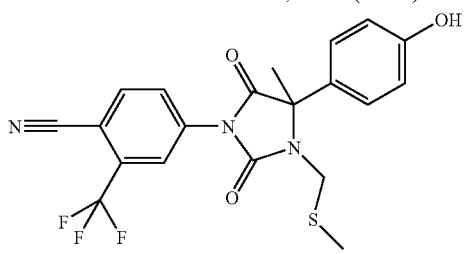

Example 222-2

4-[2,5-dioxo-4-(4-hydroxyphenyl)-4-methyl-3-methylthioimidazolidin-1-yl]-2-trifluoromethylbenzonitrile 50 g of 4-[1-(4-cyano-3-trifluoromethylphenyl)-2,5-dioxo-4-methyl-3-[(methylthio)methyl]imidazolidin-4-yl]phenyl and 1,1-dimethylethyl carbonate are dissolved in 1 mL of dichloromethane and 1 mL of a 50/50 mixture of 2N aqueous hydrochloric acid and ethyl acetate is added at 0° C. The mixture is stirred overnight at this temperature, then 3 mL of toluene are added and the solvents are removed under vacuum. The residue is diluted in a mixture of ethyl acetate and saturated aqueous sodium bicarbonate solution. The product is extracted with ethyl acetate. The solution is dried over magnesium sulphate, filtered and evaporated to give a solid which is crystallised in a mixture of heptane and dichloromethane giving 38 mg of product (Yd=93%).

1H-NMR (CDCl3): δ 2.10 (s, 3H, Me); 3.22 (s, 3H, SMe); 3.91 and 4.81 (2d, 2H, NCH2S); 5.45 (sl, 1H, OH); 6.80 (d, 2 HAr); 7.11 (d, 2 HAr); 7.84 (d, 1 HAr); 7.93 (dl, 1 HAr); 8.08 (sl, 1 HAr).

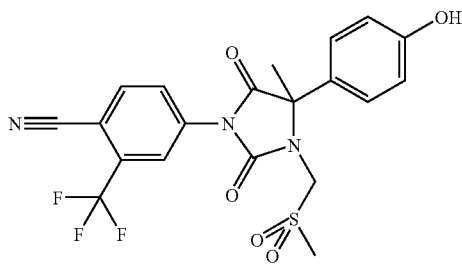

Example 222-3

4-[2,5-dioxo-4-(4-hydroxyphenyl)-4-methyl-3-[(methylsulphonyl)methyl]imidazolidin-1-yl]-2-trifluoromethylbenzonitrile The procedure of Example 222 is used starting with 15 mg of 4-[1-(4-cyano-3-trifluoromethylphenyl)-2,5-dioxo-4-methyl-3-[(methylsulphonyl)methyl]imidazolidin-4-yl]phenyl and 1,1-dimethylethyl carbonate to provide 15 mg of product after crystallisation in dichloromethane/heptane (quantitative Yd).

1H-NMR (CDCl3): δ 2.10 (s, 3H, Me); 2.71 (s, 3H, SO2Me); 3.92 and 4.79 (2d, 2H, NCH2SO2); 5.45 (sl, 1H, OH); 6.80 (d, 2 HAr); 6.9 (m, 2 HAr); 7.2 (m, 1 HAr); 7.95 to 8.05 (m, 2 HAr); 8.15 (sl, 1 HAr).

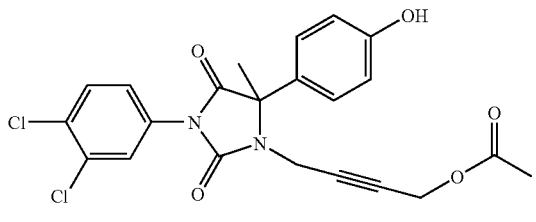

Example 223

4-[1-(3,4-dichlorophenyl)-2,5-dioxo-4-methyl-4-(4-hydroxyphenyl)imidazolidin-3-yl]-2-butynyl acetate 1 g of 4-[3-(4-acetoxy-2-butynyl)-1-(3,4-dichlorophenyl)-2,5-dioxo-4-methylimidazolidin-4-yl]phenyl and 1,1-dimethylethyl carbonate (the product of Example 193) is dissolved in 2.5 mL of a 50/50 trifluoroacetic acid/dichloromethane mixture. The mixture is stirred for 3 hours at ambient temperature then evaporated under vacuum. 0.77 g of a white solid is obtained (Yd=95%). 1H-RMN (CDCl3): δ 2.05 (s, 3H, Me); 2.1 (s, 3H, COMe); 3.8 and 4.49 (2dt, 2H, NCH2); 4.1 (sl, 2H, CH2OCO); 5.9 (s, 1H, OH); 6.8 (d, 2 HAr); 7.2 (d, 2 HAr); 7.4 (dd, 1 HAr); 7.52 (d, 1 HAr); 7.7 (d, 1 HAr).

LC/MS Gradient 1: Rt: 4.84 min; 459/461+ (MH)+

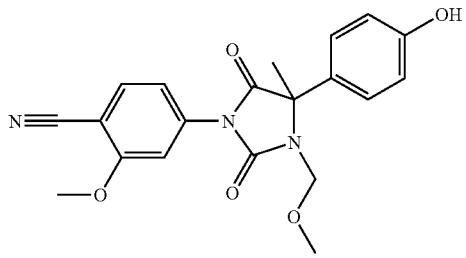

Example 223-1

4-[4-(4-hydroxyphenyl)-3-methoxymethyl-4-methyl-2,5-dioxoimidazolidin-1-yl]-2-methoxybenzonitrile 5.95 g of 4-[1-(4-cyano-3-methoxyphenyl)-2,5-dioxo-3-methoxymethyl-4-methylimidazolidin-4-yl]phenyl and 1,1-dimethylethyl carbonate are dissolved in 76 mL of dichloromethane. The solution is cooled in an ice bath and 38 mL of trifluoroacetic acid are added dropwise. The mixture is stirred for 3 hours in the ice bath then poured on an iced aqueous sodium bicarbonate solution. The product is extracted with dichloromethane, the solution is dried over magnesium sulphate, then evaporated to dryness. The product is purified over a silica column with 80/20 then 60/40 heptane/ethyl acetate. 4.18 g of the expected product are obtained (white solid; Yd=89%); Mp=141° C.

TLC: Fr=0.22 (60/40 heptane/ethyl acetate).

1H-NMR (CDCl3): δ 2.02 (s, 3H, Me); 3.42 (s, 3H, CH2O Me); 3.98 (s, 3H, PhOMe); 4.42 and 5.18 (2d, 2H, J=11 Hz, NCH2O); 5.6 (sl, 1H, OH); 6.85 (d, 2 HAr); 7.2 (d, 2 HAr); 7.28 (d, 2 HAr); 7.65 (d, 1 HAr).

LC/MS Gradient 1: Rt: 4.6 min; 380– (M–H)–; 761– (2M–H)–

Examples 224 to 241

Using the procedure of Example 223, starting from the corresponding 1,1-dimethylethyl carbonate derivative, the following products are prepared:

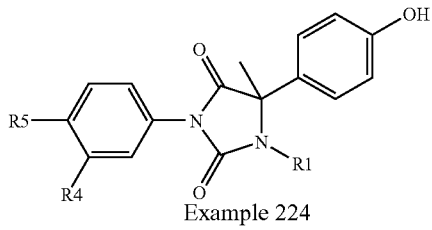

Example 224

4-[2,5-dioxo-3-ethyl-4-(4-hydroxyphenyl)-4-methylimidazolidin-1-yl]-2-trifluoromethylbenzonitrile; Mp=165° C.

1H-NMR (CDCl3): δ 1.25 (t, J=6.7 Hz, 3H, CH2CH3); 1.97 (s, 3H, Me); 3.15 and 3.60 (2dq, J=7 and 14 Hz, 2$\overline{H}$, CH2CH3); 6.89 (d, 2 HAr); 7.22 (d, 2 HAr); 7.92 (d, 1 HAr); 8.02 (dd, 1 HAr); 8.18 (d, 1 HAr).

LC/MS Gradient 1: Rt: 3.62 min; 402− (M−H)−

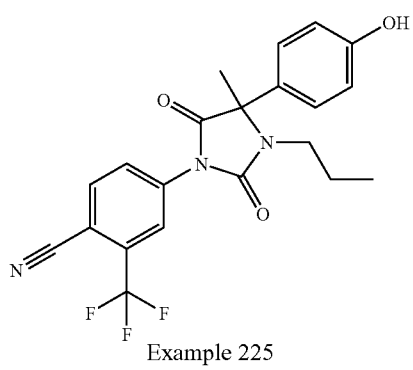

Example 225

4-[2,5-dioxo-4-(4-hydroxyphenyl)-4-methyl-3-propylimidazolidin-1-yl]-2-trifluoromethylbenzonitrile; Mp=125° C.

1H-NMR (CDCl3): δ 0.90 (t, 3H, CH2CH3); 1.53 to 1.78 (m, 2H, CH2CH3); 2.98 and 3.48 (2m, 2H, $\overline{CH2}$N); 6.89 (d, 2 HAr); 7.21 (d, 2 HAr); 7.92 (d, 1 HAr); 8.02 (dd, 1 HAr); 8.18 (d, 1 HAr).

LC/MS Gradient 1: Rt: 5.06 min; 416− (M−H)−

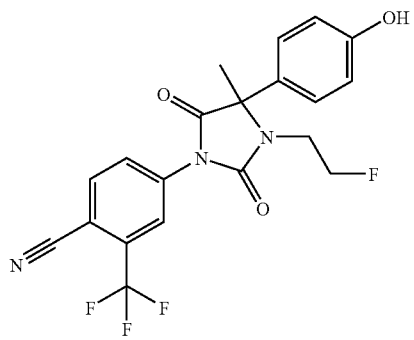

Example 226

4-[2,5-dioxo-3-(2-fluoroethyl)-4-(4-hydroxyphenyl)-4-methylimidazolidin-1-yl]-2-trifluoromethylbenzonitrile; Mp=157° C.

1H-NMR (CDCl3): δ 1.98 (s, 3H, Me); 3.29 and 3.72 (2m, 2H, CH2F) ; 4.45-4.79 (3m, 2H, NCH2); 6.90 (dd, 2 HAr); 7.20 (dd, 2 HAr); 7.92 (d, 1 HAr); 8.02 (dd, 1 HAr); 8.18 (d, 1 HAr).

LC/MS Gradient 1: Rt: 3.59 min; 420− (M−H)−

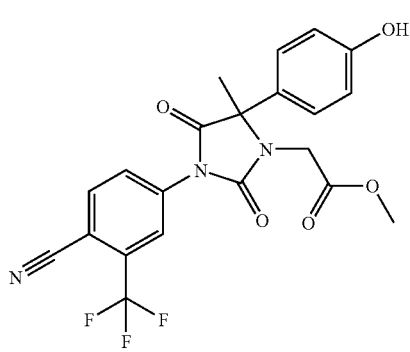

Example 227

4-[2,5-dioxo-4-(4-hydroxyphenyl)-3-[(methoxycarbonyl)methyl]-4-methylimidazolidin-1-yl]-2-trifluoromethylbenzonitrile 1H-NMR (CDCl3): δ 1.94 (s, 3H, Me); 3.57 and 4.40 (2d, J=20 Hz, 2H, NCH2CO); 3.79 (s, 3H, OMe); 6.89 (d, 2 HAr); 7.22 (d, 2 HAr); 7.92 (d, 1 HAr); 8.02 (dd, 1 HAr); 8.18 (d, 1 HAr).

LC/MS Gradient 1: Rt: 3.56 min; 446− (M−H)−

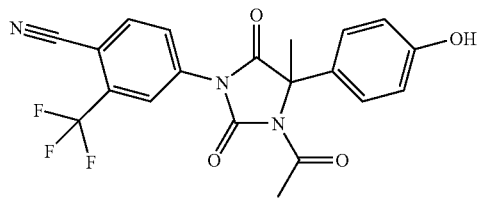

Example 228

4-[3-acetyl-2,5-dioxo-4-(4-hydroxyphenyl)-4-methylimidazolidin-1-yl]-2-trifluoromethylbenzonitrile 1H-NMR (MeOD): δ 2.21 (s, 3H, Me); 2.66 (s, 3H, COMe); 6.87 (d, 2 HAr); 7.33 (d, 2 HAr); 8.07 and 8.20 (AB, 2 HAr); 8.23 (s, 1 HAr).
LC/MS Gradient 1: Rt: 4.69 min; 331− (M−MeCONCO−H)−

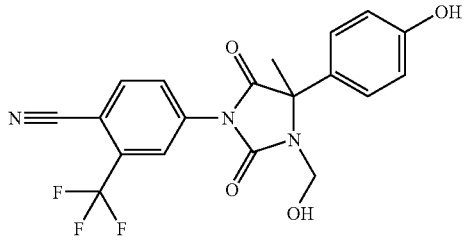

Example 228-1

4-[2,5-dioxo-3-hydroxymethyl-4-(4-hydroxyphenyl)-4-methylimidazolidin-1-yl]-2-trifluoromethylbenzonitrile 1H-NMR (CDCl3): δ 1.92 (s, 3H, Me); 5.2 et 6.02 (2d, 2H, CH2O); 6.82 (d, 2 HAr); 7.14 (d, 2 HAr); 7.88 (d, 1 HAr); 7.92 (dd, 1 HAr); 8.03 (d, 1 HAr).

Example 228-2

4-[2,5-dioxo-3-formyl-4-(4-hydroxyphenyl)-4-methylimidazolidin-1-yl]-2-trifluoromethylbenzonitrile $^1$H-NMR (CDCl$_3$): δ 2.12 (s, 3H, Me); 3.42 (s, 1H, OH); 6.8 (d, 2H$_{Ar}$); 7.2 (d, 2H$_{Ar}$); 7.86 (dd, 1H$_{Ar}$); 7.91 (d, 1H$_{Ar}$); 7.99 (d, 1H$_{Ar}$); 9.22 (s, 1H, CHO).
LC/MS Gradient 1: Rt: 2.9 min; 402− (M−H)−, 805 (2M−H)−

Example 229

4-[2,5-dioxo-4-(4-hydroxyphenyl)-3-(methoxycarbonyl)-4-methylimidazolidin-1-yl]-2-trifluoromethylbenzonitrile $^1$H-NMR (DMSO D$_6$): δ 2.11 (s, 3H, Me); 3.70 (s, 3H, OMe); 6.79 (d, 2H$_{Ar}$); 7.32 (d, 2H$_{Ar}$); 8.07 (d, 1H$_{Ar}$); 8.18 (s, 1H$_{Ar}$); 8.38 (d, 1H$_{Ar}$); 9.68 (s, 1H, OH).
LC/MS Gradient 1: Rt: 4.26 min; 331− (M−MeOCONCO−H)−

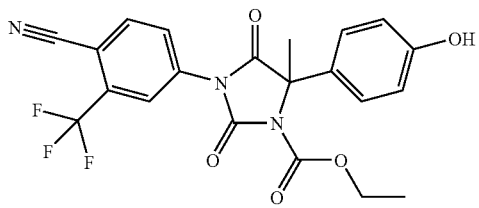

Example 230

4-[2,5-dioxo-3-(ethoxycarbonyl)-4-(4-hydroxyphenyl)-4-methylimidazolidin-1-yl]-2-trifluoromethylbenzonitrile 1H-NMR (DMSO D6): δ 1.08 (t, 3H, CH2CH3); 2.11 (s, 3H, Me); 4.12 (q, 2H, CH2CH3); 6.79 (d, 2 HAr); 7.32 (d, 2 HAr); 8.07 (d, 1 HAr); 8.18 (s, 1 HAr); 8.38 (d, 1 HAr); 9.68 (s, 1H, OH).
LC/MS Gradient 1: Rt: 4.37 min; 331− (M−EtOCONCO−H)−

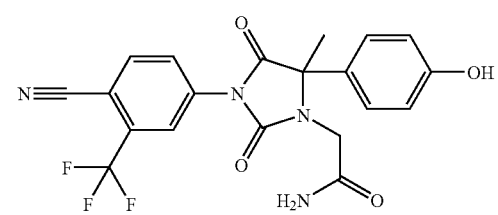

Example 231

4-[3-[(aminocarbonyl)methyl]-2,5-dioxo-4-(4-hydroxyphenyl)-4-methylimidazolidin-1-yl]-2-trifluoromethylbenzonitrile 1H-NMR (acetone D6): δ 2.78 (s, 3H, Me); 3.54 and 4.28 (2d, J=16.7 Hz, 2H, NCH2); 6.5 and 6.97 (2s, 2H, CONH2); 6.92 (d, 2 HAr); 7.36 (d, 2 HAr); 8.21 (m, 2 HAr); 8.33 (s, 1 HAr); 8.62 (s, 1H, OH).
LC/MS Gradient 1: Rt: 1.24 min; 431− (M−H)−

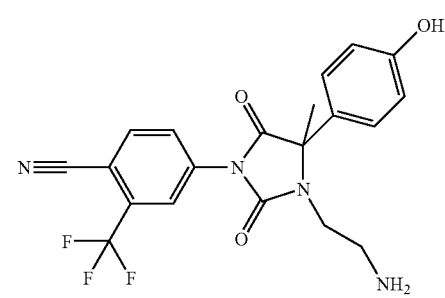

Example 232

4-[3-(2-aminoethyl)-2,5-dioxo-4-(4-hydroxyphenyl)-4-methylimidazolidin-1-yl]-2-trifluoromethylbenzonitrile 1H-NMR (CDCl3+2 drops of pyridine D5): δ 1.96 (s, 3H, Me); 2.91 (s, 2H, NH2); 3.15 and 4.02 (2m, 2H, NCH2); 3.57

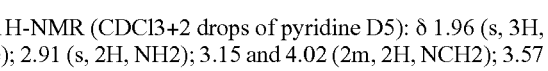

(m, 2H, CH2NH2); 6.85 (AB, 2 HAr); 7.07 (AB, 2 HAr); 8.2 (dd, 1 HAr); 7.91 (dd, 1 HAr); 8.05 (s, 1 HAr).

LC/MS Gradient 1: Rt: 0.88 min; 417– (M–H)–; 419+ (MH)+

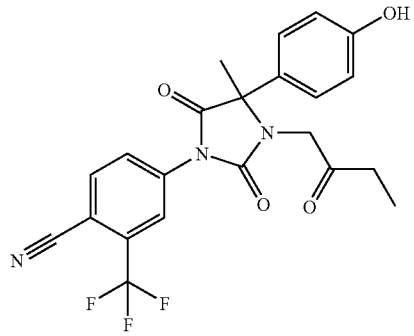

Example 233

4-[2,5-dioxo-4-(4-hydroxyphenyl)-4-methyl-3-(2-oxobutyl)imidazolidin-1-yl]-2-trifluoromethylbenzonitrile 1H-NMR (CDCl3): δ 1.12 (t, 3H, CH2CH3); 1.89 (s, 3H, Me); 2.40 (m, 2H, CH2CH3); 3.69 and 4.46 (2d, J=20 Hz, 2H, NCH2); 5.29 (s, 1H); 6.90 (d, 2 HAr); 7.25 (d, 2 HAr); 7.91 (d, 1 HAr); 8.02 (dd, 1 HAr); 8.18 (d, 1 HAr).

LC/MS Gradient 1: Rt: 1.21 min; 444– (M–H)–

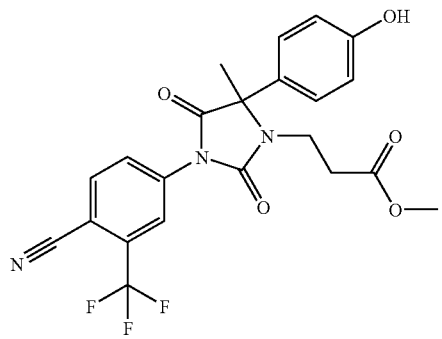

Example 234

4-[2,5-dioxo-4-(4-hydroxyphenyl)-3-[2-(methoxycarbonyl)ethyl]-4-methylimidazolidin-1-yl]-2-trifluoromethylbenzonitrile 1H-NMR (MeOD): δ 1.96 (s, 3H, Me); 2.52 to 2.70 (m, 2H, CH2CO); 3.48 and 3.68 (2m, 2H, CH2N); 3.62 (s, 3H, OMe); 6.87 (d, 2 HAr); 7.28 (d, 2 HAr); 8.10 (m, 2 HAr); 8.22 (s, 1 HAr).

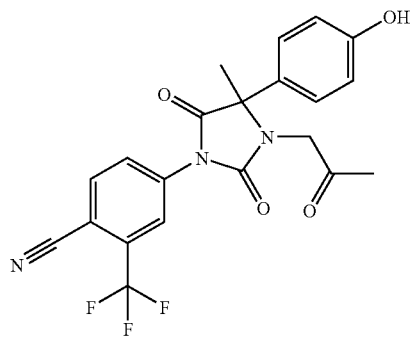

Example 235

4-[2,5-dioxo-4-(4-hydroxyphenyl)-4-methyl-3-(2-oxopropyl)imidazolidin-1-yl]-2-trifluoromethylbenzonitrile 1H-NMR (CDCl3): δ 1.88 (s, 3H, Me); 2.21 (s, 3H, MeCO); 3.70 and 4.48 (2d, 2H, J=20 Hz, NCH2CO); 6.89 (d, 2 HAr); 7.24 (d, 2 HAr); 7.92 (d, 1 HAr); 8.02 (dd, 1 HAr); 8.18 (d, 1 HAr).

LC/MS Gradient 1: Rt: 4.32 min; 430– (M–H)–

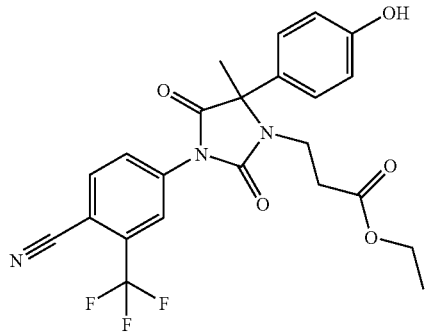

Example 236

4-[2,5-dioxo-3-[2-(ethoxycarbonyl)ethyl]-4-(4-hydroxyphenyl)-4-methylimidazolidin-1-yl]-2-trifluoromethylbenzonitrile 1H-NMR (CDCl3): δ 1.26 (t, 3H, CH2CH3); 1.96 (s, 3H, Me); 2.68 (m, 2H, CH2CO); 3.44 to 3.74 (2m, 2H, NCH2); 4.12 (q, 2H, OCH2); 6.89 (d, 2 HAr); 7.21 (d, 2 HAr); 7.92 (d, 1 HAr); 8.02 (dd, 1 HAr); 8.18 (d, 1 HAr).

LC/MS Gradient 1: Rt: 4.50 min; 474– (M–H)–

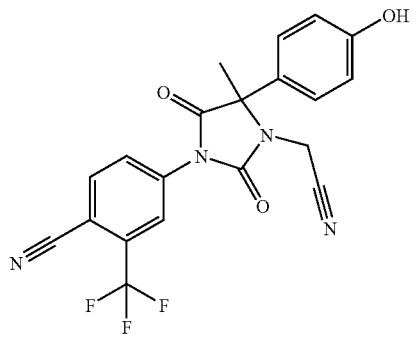

Example 237

4-[3-(cyanomethyl)-2,5-dioxo-4-(4-hydroxyphenyl)-4-methylimidazolidin-1-yl]-2-trifluoromethylbenzonitrile 1H-NMR (CDCl3): δ 2.11 (s, 3H, Me); 3.87 and 4.60 (2d, 2H, J=20 Hz, CH2N); 5.38 (s, 1H, OH); 6.84 (d, 2 HAr); 7.22 (d, 2 HAr); 8.0 (m, 2 HAr); 8.14 (s, 1 HAr).

LC/MS Gradient 1: Rt: 4.34 min; 413– (M–H)–

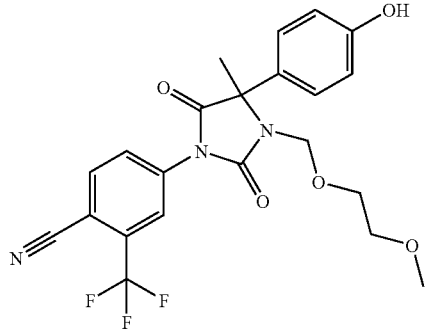

Example 238

4-[2,5-dioxo-4-(4-hydroxyphenyl)-3-[(2-methoxyethoxy)methyl]-4-methylimidazolidin-1-yl]-2-trifluoromethylbenzonitrile 1H-NMR (CDCl3): δ 2.05 (s, 3H, Me); 3.39 (s, 3H, MeO); 3.55 (t, 2H, CH2O); 3.74 and 3.82 (2m, 2H, CH2O); 4.50 and 5.27 (2d, 2H, J=13.3 Hz, NCH2O); 6.89 (d, 2 HAr); 7.21 (d, 2 HAr); 7.92 (d, 1 HAr); 8.02 (dd, 1 HAr); 8.17 (d, 1 HAr).

LC/MS Gradient 1: Rt: 5.45 min; no ionisation

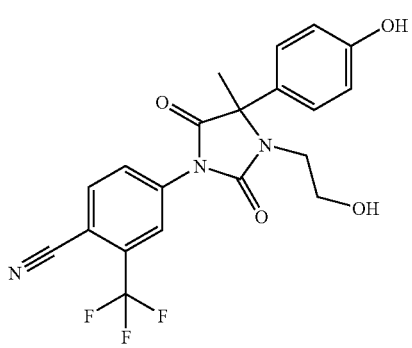

Example 239

4-[2,5-dioxo-3-(2-hydroxyethyl)-4-(4-hydroxyphenyl)-4-methylimidazolidin-1-yl]-2-trifluoromethylbenzonitrile 1H-NMR (CDCl3): δ 1.98 (s, 3H, Me); 3.30 and 3.60 (2m, 2H, CH2N); 3.82 (m, 2H, CH2O); 5.20 (s, 1H, OH); 6.90 (d, 2 HAr); 7.23 (d, 2 HAr); 7.92 (d, 1 HAr); 8.02 (dd, 1 HAr); 8.17 (d, 1 HAr).

LC/MS Gradient 1: Rt: 5.02 min; 418− (M−H)−

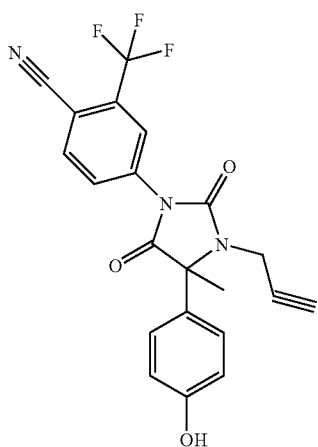

Example 240

4-[2,5-dioxo-4-(4-hydroxyphenyl)-4-methyl-3-(2-propynyl)imidazolidin-1-yl]-2-trifluoromethylbenzonitrile LC/MS Gradient 1: Rt: 3.70 min; 412− (M−H)−

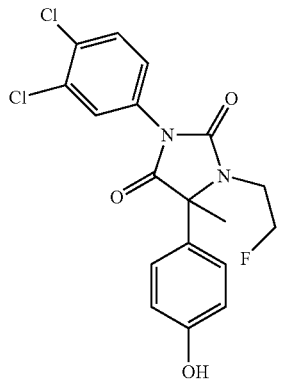

Example 241

1-(3,4-dichlorophenyl)-3-(2-fluoroethyl)-4-(4-hydroxyphenyl)-4-methylimidazolidine-2,5-dione LC/MS Gradient 1: Rt: 5.70 min; 514/516+ (MH+H2O)+

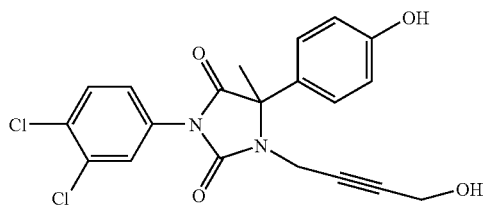

Example 242

1-(3,4-dichlorophenyl)-3-(4-hydroxy-2-butynyl)-4-(4-hydroxyphenyl)-4-methylimidazolidine-2,5-dione 500 mg 4-[1-(3,4-dichlorophenyl)-2,5-dioxo-4-(4-hydroxyphenyl)-4-methylimidazolidin-3-yl]-2-butynyl acetate (the product of Example 223) are dissolved in 10 mL of a 2 N ethanol/HCl mixture (70/30). The mixture is stirred under reflux for 3 hours then concentrated and dried under vacuum. 400 mg of a white solid are obtained (Yd=99%).

1H-RMN(CDCl3): δ 2.0 (s, 3H, Me); 3.82 and 4.4 (2d, 2H, J=20 Hz, NCH2); 4.2 (s, 2H, CH2OH); 6.8 (d, 2 HAr); 7.2 (d, 2 HAr); 7.4 (d, 1 HAr); 7.52 (d, 1 HAr); 7.68 (s, 1 HAr).

LC/MS Gradient 1: Rt: 4.4 min; 417/419− (M−H)−

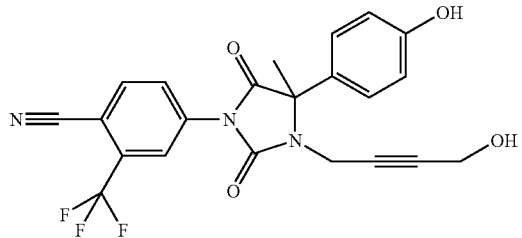

Example 243

4-[2,5-dioxo-3-(4-hydroxy-2-butynyl)-4-(4-hydroxyphenyl)-4-methylimidazolidinyl-1-yl]-2-trifluoromethylbenzonitrile The product is prepared by the procedure of Example 242, starting with 4-[3-(4-acetoxy-2-butynyl)-1-(4-cyano-3-trifluoromethylphenyl)-2,5-dioxo-4-methylimidazolidin-4-yl]phenyl and 1,1-dimethylethyl carbonate (the product of Example 218).

LC/MS Gradient 1: Rt: 4.32 min; 442– (M–H)–

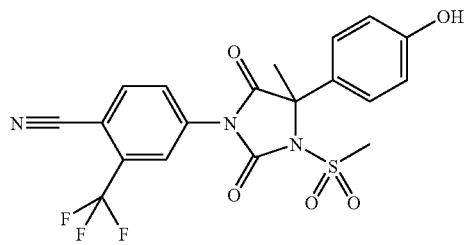

Example 243-1

4-[2,5-dioxo-4-(4-hydroxyphenyl)-4-methyl-3-(methylsulphonyl)imidazolidin-1-yl]-2-trifluoromethylbenzonitrile 236 mg of crude 4-[1-(4-cyano-3-trifluoromethylphenyl)-2,5-dioxo-4-methyl-3-(methylsulphonyl)imidazolidin-4-yl]phenyl and 1,1-dimethylethyl carbonate are stirred for 30 min in a mixture of 2 mL of dichloromethane and 1 mL of trifluoroacetic acid. The mixture is poured in an aqueous sodium bicarbonate solution and the product is extracted by ethyl acetate. The solution is dried over sodium sulphate, filtered and evaporated to give 120 mg of product. 55 mg of pure product are obtained by chromatography over silica gel (eluent dichloromethane/ethyl acetate 97/3) (Yd=39% for 2 steps).

1H-NMR (CDCl3): δ 2.30 (s, 3H, Me); 3.30 (s, 3H, SO2Me); 6.93 (d, 2 HAr); 7.35 (d, 2 HAr); 7.98 (AB, 2 HAr); 8.11 (s, 1 HAr).

LC/MS Gradient 1: Rt: 4.76 min; 905– (2M–H)–; 331–

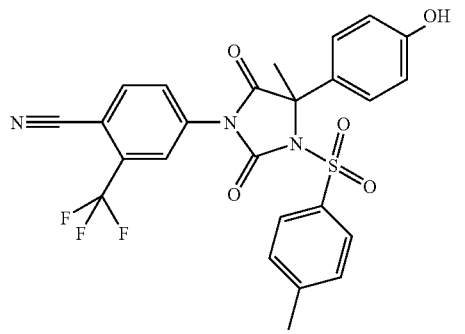

Example 243-2

4-[2,5-dioxo-4-(4-hydroxyphenyl)-4-methyl-3-[(4-methylphenyl)sulphonyl]imidazolidin-1-yl]-2-trifluoromethylbenzonitrile The procedure of Example 243-1 is applied with 4-[1-(4-cyano-3-trifluoromethylphenyl)-2,5-dioxo-4-methyl-3-[(4-methylphenyl)sulphonyl]imidazolidin-4-yl]phenyl and 1,1-dimethylethyl carbonate to produce 174 mg of crude product. 75 mg of pure product are obtained by chromatography over silica gel (eluent dichloromethane/ethyl acetate 97/3) in the form of a white solid (Yd=46% for 2 steps).

1H-NMR (CDCl3): δ 2.28 (s, 3H, Me); 2.37 (s, 3H, PhMe); 5.00 (sl, 1H, OH); 6.80 (d, 2 HAr); 7.18 (d, 2 HAr); 7.20 (d, 2 HAr); 7.57 (d, 2 HAr); 7.82 (AB, 2 HAr); 7.94 (s, 1 HAr).

LC/MS Gradient 1: Rt: 5.27 min; 530+ (MH)+; 331–

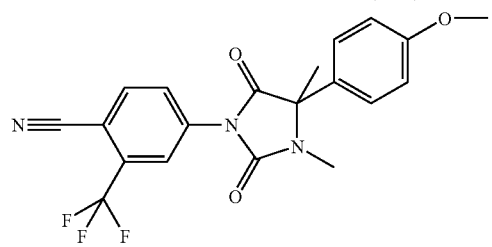

Example 340

4-[3,4-dimethyl-2,5-dioxo-4-(4-methoxyphenyl)imidazolidin-1-yl]-2-trifluoromethylbenzonitrile 1.2 g of 4-[3,4-dimethyl-2,5-dioxo-4-(4-hydroxyphenyl)imidazolidin-1-yl]-2-trifluoromethylbenzonitrile is dissolved in 30 mL of DMF. 637 mg of potassium carbonate are added at ambient temperature. After 20 min of stirring at ambient temperature, 0.45 mL of methyl iodide is added. After 2.5 hours at AT, the mixture is poured over a saturated aqueous sodium bicarbonate solution and subjected to extraction with ethyl acetate, the organic phase is washed with a saturated sodium chloride solution then dried over magnesium sulphate, filtered and evaporated. The yellow oil obtained is taken up several times with isopropyl ether and evaporated until crystallisation begins. After one night in the refrigerator, the solid is filtered, rinsed several times with isopropyl ether and dried under vacuum to yield 989 mg of white crystals (Yd=80%); Mp=117° C.

TLC: Fr=0.40 (50/50 heptane/ethyl acetate).

1H-NMR (MeOD): δ 1.9 (s, 3H, Me); 2.85 (s, 3H, NMe); 3.8 (s, 3H, OMe); 7.0 (d, 2 HAr); 7.31 (d, 2 HAr); 8.02 and 8.08 (AB, 2 HAr); 8.2 (s, 1 HAr).

LC/MS Gradient 1: Rt: 5.57 min; 445+ (MH+CH3CN)+

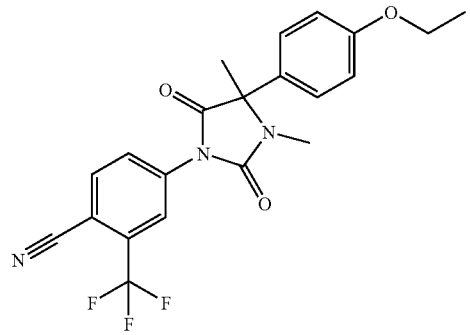

Example 341

4-[3,4-dimethyl-2,5-dioxo-4-(4-ethoxyphenyl)imidazolidin-1-yl]-2-trifluoromethylbenzonitrile Using the procedure of Example 340, starting from 1.2 g of 4-[3,4-dimethyl-2,5-dioxo-4-(4-hydroxyphenyl)imidazolidin-1-yl]-2-trifluoromethylbenzonitrile with ethyl iodide, 874 mg of product are obtained (Yd=68%); Mp=131.4° C.

1H-NMR (MeOD): δ 1.4 (t, J=7 Hz, 3H, CH3CH2); 1.95 (s, 3H, Me); 2.9 (s, 3H, NMe); 4.08 (q, J=7 Hz, 2H, CH3C H2); 7.0 (d, 2 HAr); 7.35 (d, 2 HAr); 8.05 and 8.1 (AB, 2 HAr); 8.2 (s, 1 HAr).

LC/MS Gradient 1: Rt: 5.86 min; 459+ (MH+CH3CN)+

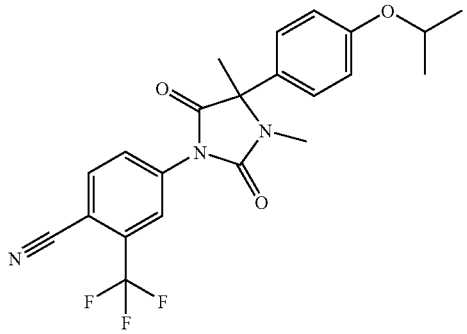

Example 342

4-[3,4-dimethyl-2,5-dioxo-4-[4-(1-methylethoxy) phenyl]imidazolidin-1-yl]-2-trifluoromethylbenzonitrile Using the procedure of Example 341, starting from 1.2 g of 4-[3,4-dimethyl-2,5-dioxo-4-(4-hydroxyphenyl)imidazolidin-1-yl]-2-trifluoromethylbenzonitrile and isopropyl iodide, 1.12 g of product is obtained (Yd=84%); Mp=113.9° C.

1H-NMR (MeOD): δ 1.8 (d, J=7 Hz, 6H, (CH3)2CH); 1.92 (s, 3H, Me); 2.9 (s, 3H, NMe); 4.63 (m, 1H, (CH3)2CH); 7.0 (d, 2 HAr); 7.3 (d, 2 HAr); 8.05 and 8.1 (AB, 2 HAr); 8.2 (s, 1 HAr).

LC/MS Gradient 1: Rt: 8.73 min; 473+ (MH+CH3CN)+

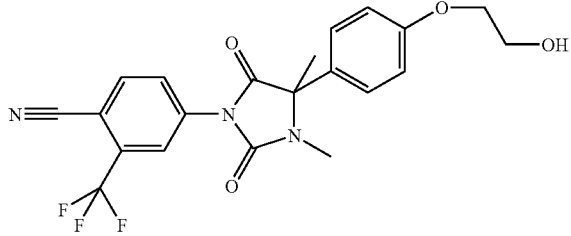

Example 343

3,4-dimethyl-2,5-dioxo-4-[4-(2-hydroxyethoxy)phenyl]imidazolidin-1-yl)-2-trifluoromethylbenzonitrile Stage 1

778 mg of 4-[3,4-dimethyl-2,5-dioxo-4-(4-hydroxyphenyl)imidazolidin-1-yl]-2-trifluoromethylbenzonitrile are dissolved in 20 mL of DMF. 414 mg of potassium carbonate are added, at ambient temperature. After 15 min of stirring, 2.35 mL of (2-bromoethoxy)terbutyldimethylsilane are added, then the mixture is heated for 36 hours at 40° C. The mixture is poured over a saturated aqueous sodium bicarbonate solution, extracted with ethyl acetate, the organic phase is washed with saturated sodium chloride solution then dried over sodium sulphate, filtered and evaporated to dryness. 2.77 g of a pale yellow oil of silylated derivative (quantitative Yd) is obtained and used directly in the following stage.

TLC: Fr=0.33 (50/50 heptane/ethyl acetate).

Stage 2

6 mL of 1 M tetrabutyl ammonium fluoride solution in THF is added to a solution of 2.77 g of 3,4-dimethyl-4-[4-[2-[(dimethyl-(2,2-dimethylethyl)silyl)oxy]ethoxy]phenyl]-2,5-dioxoimidazolidin-1-yl)-2-trifluoromethylbenzonitrile in 20 mL of THF at ambient temperature. After 2 hours at ambient temperature, a further 6 mL of tetrabutyl ammonium fluoride are added. After a total reaction time of 3 hours, the mixture is poured over a saturated aqueous potassium dihydrogen phosphate solution, extracted with ethyl acetate, the organic phase is washed with a saturated sodium chloride solution then dried over sodium sulphate, filtered and evaporated to dryness. The pale yellow oil obtained (1.94 g) is purified over a silica column with a 50/50 then 40/60 heptane/ethyl acetate mixture to yield an amorphous foam which crystallises in the heptane/isopropyl ether mixture. After centrifuging and drying, 722 mg of product are obtained in the form of a white powder (Yd=74%); Mp=120.2° C.

TLC: Fr=0.23 (30/70 heptane/ethyl acetate).

1H-NMR (CDCl3): δ 1.95 (s, 3H, Me); 2.95 (s, 3H, NMe); 4.0 and 4.1 (2sl, 4H, CH2O); 7.0 (d, 2 HAr); 7.3 (d, 2 HAr); 7.9 (d, 2 HAr); 8.0 (d, 2 HAr); 8.18 (s, 1 HAr).

LC/MS Gradient 1: Rt: 4.23 min; 477− (M−H+CH3CN)−

Intermediates

The products used as intermediates for preparing the compounds of Examples 1 to 343 may be prepared in the following manner:

Example A 4-hydroxy-2-butynyl acetate

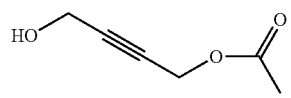

4.75 g of NaH, 55% in oil, are washed with anhydrous THF in a Woulff bottle equipped with a magnetic stirrer. 100 mL of THF are added, then 20 g of 2-butyne-1,4-diol dissolved in 200 mL of THF are added dropwise at 0° C. 10 mL of acetic anhydride are then added dropwise while maintaining the temperature at between 5 and 10° C. The mixture is stirred for 1 hour at AT then the THF is evaporated. The residue is taken up in water and the product is extracted with dichloromethane. After drying over magnesium sulphate and concentrating, 15.47 g of product in the form of a yellow liquid are obtained. After purification over a silica column with pure dichloromethane then 90/10 dichloromethane/ethyl acetate, 7.97 g of product are obtained (Yd=27%).

TLC: Fr=0.4 (90/10 dichloromethane/ethyl acetate)

1H-NMR (MeOD): 1.7 (s, 1H, OH); 2.1 (s, 3H, Me); 4.35 (s, 2H, CH2OH); 4.7 (s, 2H, CH2OCO).

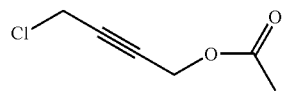

Example B 4-chloro-2-butynyl acetate 10 g of 4-hydroxy-2-butynyl acetate and 50 mL of dichloromethane are introduced into a flask. 10.3 mL of 1-chloro- N,N,2-trimethyl-1-propenylamine are progressively added. After stirring for 3 hours at ambient temperature the solvent is evaporated to yield 20 g of a yellow oil. The crude product is purified over a silica column with pure dichloromethane. 10.33 g of product are obtained (Yd=94%).

TLC: Fr=0.8 (dichloromethane)

Intermediates I (R1=H)

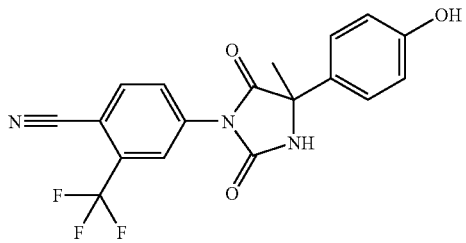

Example C

4-[2,5-dioxo-4-(4-hydroxyphenyl)-4-methylimidazolidin-1-yl]-2-trifluoromethylbenzonitrile This product is prepared as in Example 5, starting from 10.71 g of methyl 2-amino-2-(4-hydroxyphenyl)propionate using 4-cyano-3-trifluoromethylphenyl isocyanate. 16.83 g of product are obtained (Yd=82%).

1H-NMR (MeOD): δ 1.89 (s, 3H, Me); 6.85 (d, 2 HAr); 7.42 (d, 2 HAr); 8.08 (AB, 2 HAr); 8.19 (s, 1 HAr).

1H-NMR (CDCl3): δ 1.96 (s, 3H, Me); 6.09 (s, 1H, NH); 6.91 (d, 2 HAr); 7.42 (d, 2 HAr); 7.95 (m, 2 HAr); 8.11 (d, 1 HAr).

LC/MS Gradient 1: Rt: 3.57 min; 374− (M−H)−

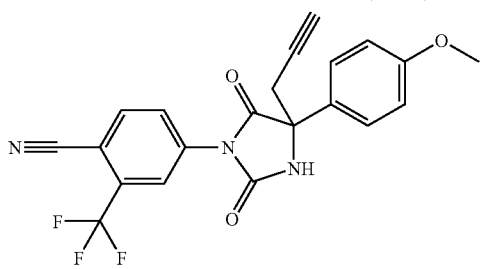

Example C-1

4-[2,5-dioxo-4-(4-methoxyphenyl)-4-(2-propynyl)imidazolidin-1-yl]-2-trifluoromethylbenzonitrile This product is prepared as in Example 5, starting from 250 mg of methyl 2-amino-2-(4-hydroxyphenyl)-4-pentynoate using 4-cyano-3-trifluoromethylphenyl isocyanate. 380 mg of product are obtained (Yd=86%).

1H-NMR (CDCl3): δ 2.14 (dd, 1H, ≡CH); 3.05 to 3.27 (AB, 2H, CH2); 3.85 (s, 3H, OMe); 6.41 (sl, 1H, NH); 6.99 (d, 2 HAr); 7.52 (d, 2 HAr); 7.95 (s, 2 HAr); 8.08 (s, 1 HAr).

LC/MS Gradient 1: Rt: 5.56 min; 412− (M−H)−

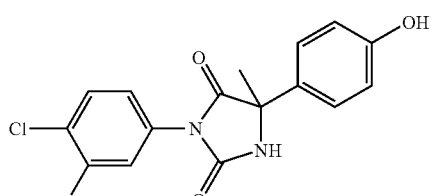

Example D 1-(3,4-dichlorophenyl)-4-(4-hydroxyphenyl)-4-methylimidazolidine-2,5-dione The procedure of Example C is used with 3,4-dichlorophenyl isocyanate starting from 10.4 g of methyl 2-amino-2-(4-hydroxyphenyl)propionate. After chromatography over silica and crystallisation in isopropyl ether, 19 g of product, a white solid, are obtained (quantitative Yd).

1H-NMR (CDCl3): δ 1.92 (s, 3H, Me); 6.1 (s, 1H, NH); 6.87 (d, 2 HAr); 7.35 (dl, 1 HAr); 7.40 (d, 2 HAr); 7.53 (d, 1 HAr); 7.62 (dl, 1 HAr);

LC/MS Gradient 1: Rt: 4.49 min; 349/351− (M−H)−; 392+ (MH+CH3CN)+

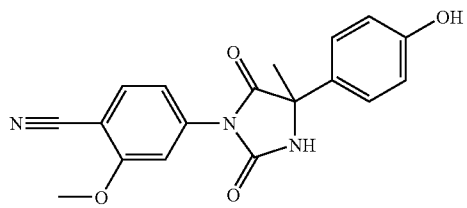

Example D-1

4-[4-(4-hydroxyphenyl)-4-methyl-2,5-dioxoimidazolidin-1-yl]-2-methoxybenzonitrile The procedure of Example C is used, with 4-cyano-3-methoxyphenyl isocyanate starting from 2.2 g of methyl 2-amino-2-(4-hydroxyphenyl)propionate. After chromatography over silica and evaporation of the solvents 3.6 g of product, a yellowish solid, is obtained (Yd=92%).

1H-NMR (CDCl3): δ 1.95 (s, 3H, Me); 3.95 (s, 3H, OMe); 6.07 (s, 1H, NH); 6.88 (d, 2 HAr); 7.21 (d, 2 HAr); 7.42 (d, 1 HAr); 7.53 (d, 1 HAr); 7.63 (dl, 1 HAr).

LC/MS Gradient 1: Rt: 4.24 min; 336− (M−H)−

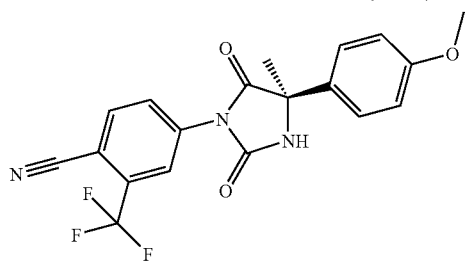

Example E (R)-4-[2,5-dioxo-4-(4-methoxyphenyl)-4-methylimidazolidin-1-yl]-2-trifluoromethylbenzonitrile 3.1 g of methyl(R)-2-amino-2-(4-methoxyphenyl)propionate are dissolved in 60 mL of THF under argon. 19 mL of a 1 M solution of 4-cyano-3-trifluoromethylphenyl isocyanate in THF are added. After 20 min at ambient temperature, 2 mL of triethylamine are added then the mixture is heated under reflux for 2 hours. The mixture is left to return to AT and evaporated to dryness, and the residue is purified by chromatography over silica while eluting with a heptane/ethyl acetate mixture (2/1). 5.5 g of product are obtained in the form of a white resin (Yd=92%).

[α]D=+26.4° (c=1%, MeOH).

TLC: Fr=0.1 (2/1 heptane/ethyl acetate).

1H-NMR (CDCl3): δ 1.96 (s, 3H, Me); 3.85 (s, 3H, OMe); 6.22 (s, 1H, NH); 6.96 (d, 2 HAr); 7.48 (d, 2 HAr); 7.92 (d, 1 HAr); 7.98 (dd, 1 HAr); 8.12 (d, 1 HAr).

LC/MS Gradient 1: Rt: 4.73 min; 388– (M–H)–; 390+ (MH)+

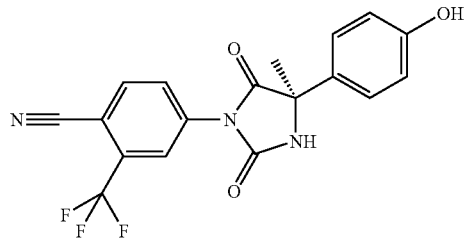

Example E-1

(R)-4-[4-(4-hydroxyphenyl)-4-methyl-2,5-dioxoimidazolidin-1-yl]-2-trifluoromethylbenzonitrile 5 g of (R)-4-[4-(4-methoxyphenyl)-4-methyl-2,5-dioxoimidazolidin-1-yl]-2-trifluoromethylbenzonitrile are dissolved in 50 mL of dichloromethane. 14 mL of boron trifluoride/dimethylsulphide complex are added and the mixture is stirred overnight at AT. It is then poured in an aqueous solution of sodium bicarbonate and the product is extracted with dichloromethane. After drying over magnesium sulphate then evaporation of the solvent, the crude product is purified over a silica gel column (eluent 50/50 heptane/ethyl acetate) to provide 3.5 g of a slightly brown solid.

1H-NMR (DMSO D6): δ 1.79 (s, 3H, Me); 6.80 (d, 2 HAr); 7.36 (d, 2 HAr); 8.03 (dd, 1 HAr); 8.20 (d, 1 HAr); 8.29 (d, 1 HAr); 9.36 (s, 1H, NH); 9.58 (s, 1H, OH).

LC/MS Gradient 1: Rt: 4.53 min; 374– (M–H)–

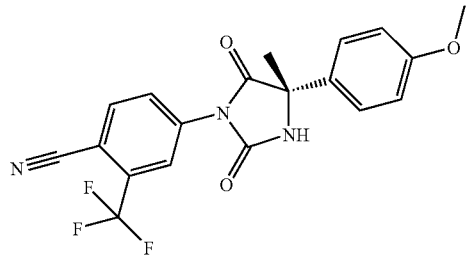

Example F (S)-4-[2,5-dioxo-4-(4-methoxyphenyl)-4-methylimidazolidin-1-yl]-2-trifluoromethylbenzonitrile Following the procedure of Example E, starting from 540 mg of methyl(S)-2-amino-2-(4-methoxyphenyl)propionate, 965 mg of product in the form of a white solid are obtained (Yd=96%).

[α]D=–26.4° (c=1%, MeOH).

1H-NMR (CDCl3): δ 1.9 (s, 3H, Me); 3.81 (s, 3H, OMe); 6.99 (d, 2 HAr); 7.53 (d, 2 HAr); 8.07 (AB, 2 HAr); 8.18 (s, 1 HAr).

LC/MS Gradient 1: Rt: 4.33 min; 388– (M–H)–; 431+ (MH+CH3CN)+

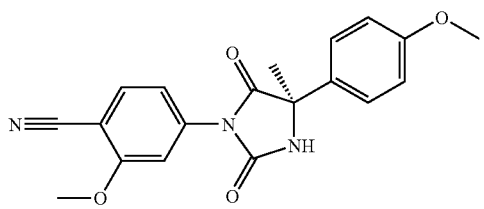

Example F-1

(R)-4-[2,5-dioxo-4-(4-methoxyphenyl)-4-methylimidazolidin-1-yl]-2-methoxybenzonitrile A solution of 1.56 g of 4-amino-2-methoxybenzonitrile in 22 mL of dioxane is added slowly (30 min) to a solution of 2.08 g of triphosgene in 22 mL of toluene. The mixture is stirred at AT for 0.25 hour and refluxed for 1.5 hour. It is then cooled to AT, filtered and evaporated to dryness. The crude product is diluted with 30 mL of THF and 2.1 g of methyl (R)-2-amino-2-(4-methoxyphenyl)propionate are added. The mixture is stirred at AT for 2 hours and evaporated to dryness. This crude product is diluted with 30 mL of dioxane and 1.4 mL of triethylamine is added. The mixture is refluxed for 2 hours and evaporated to dryness. The crude product is diluted with water and extracted with ethyl acetate. The organic layer is dried over magnesium sulphate, filtered and evaporated. The crude product is purified by chromatography over silica gel while eluting with 50/50 heptane/ethyl acetate. 3.4 g of a yellow solid are obtained (Yd=97%).

TLC: Fr=0.38 (50/50 heptane/ethyl acetate).

1H-NMR (CDCl3): δ 1.93 (s, 3H, Me); 3.84 and 3.94 (2s, 6H, 2OMe); 6.57 (s, 1H, NH); 6.97 (d, 2 HAr); 7.18 to 7.23 (m, 2 HAr); 7.48 (d, 2 HAr); 7.62 (d, 1 HAr).

LC/MS Gradient 1: Rt: 4.46 min; 350– (M–H)–

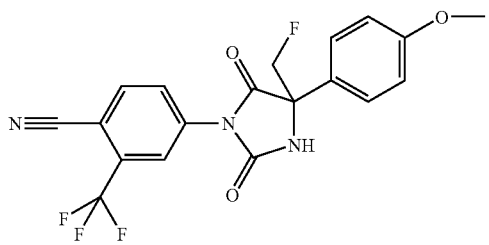

Example I

4-[2,5-dioxo-4-fluoromethyl-4-(4-methoxyphenyl) imidazolidin-1-yl]-2-trifluoromethylbenzonitrile 0.452 g of 5-fluoromethyl-5-(4-methoxyphenyl)imidazolidine-2,4-dione, 0.475 g of 4-bromo-2-trifluoromethylbenzonitrile and 0.163 g of cuprous oxide are heated to 150° C. in 1.9 mL of dimethylacetamide for 18 hours under nitrogen. After extractions with 50% ethyl acetate/ammonia then washing with a saturated aqueous sodium chloride solution and drying over sodium sulphate, the residue obtained by evaporation of the solvent is purified over a silica column with 100/0 to 65/35 heptane/ethyl acetate to yield 0.707 g of product (slightly yellow foam, Yd=91%).

TLC: Fr=0.36 (50/50 heptane/ethyl acetate).

1H-NMR (CDCl3): δ 3.85 (s, 3H, OMe); 4.6 and 5.1 (2dd, 2H, J=10 and 47 Hz, CH2F); 6.5 (sl, 1H, NH); 7.01 and 7.53 (AB, 4 HAr); 7.95 (m, 2 HAr); 8.09 (s, 1 HAr).

LC/MS Gradient 1: Rt: 3.71 min; 406– (M–H)–

Using the procedure of Example I, starting from the appropriate intermediate XI and 4-bromo-2-trifluoromethylbenzonitrile, the following products are obtained:

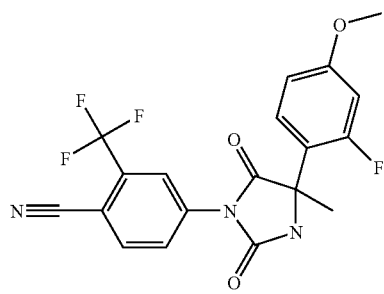

Example J

4-[2,5-dioxo-4-(2-fluoro-4-methoxyphenyl)-4-methylimidazolidin-1-yl]-2-trifluoromethylbenzonitrile
Yd=85%

1H-NMR (MeOD): δ 1.94 (s, 3H, Me); 3.82 (s, 3H, OMe); 6.66 and 6.78 (2 d 15/85, 1 HAr); 6.83 (d, 1 HAr); 7.45 and 7.52 (2 t 15/85, 1 HAr); 8.05 (d, 1 HAr); 8.13 (d, 1 HAr); 8.15 (s, 1 HAr).

LC/MS Gradient 1: Rt: 3.72 min; 406– (M–H)–

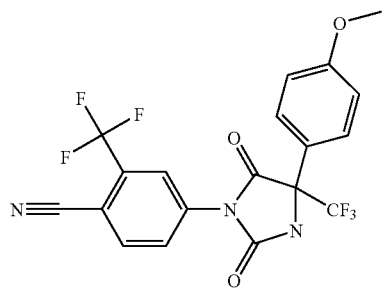

Example K

4-[2,5-dioxo-4-(4-methoxyphenyl)-4-trifluoromethylimidazolidin-1-yl]-2-trifluoromethylbenzonitrile
Yd=62%

1H-NMR (CDCl3): δ 3.00 (s, 1H, NH); 3.78 (s, 3H, OMe); 6.95 (d, 2 HAr); 7.32 (d, 2 HAr); 7.88 (s, 2 HAr); 8.02 (s, 1 HAr).

LC/MS Gradient 1: Rt: 3.91 min; 442– (M–H)–

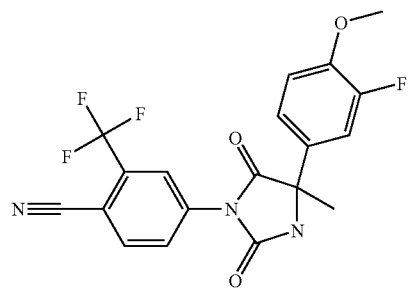

Example L

4-[2,5-dioxo-4-(3-fluoro-4-methoxyphenyl)-4-methylimidazolidin-1-yl]-2-trifluoromethylbenzonitrile
Yd=87%

1H-NMR (MeOD): δ 1.89 (s, 3H, Me); 3.88 (s, 3H, OMe); 7.15 (t, 1 HAr); 7.38 (m, 2 HAr); 8.08 (AB, 2 HAr); 8.18 (s, 1 HAr).

LC/MS Gradient 1: Rt: 5.14 min; 406– (M–H)–

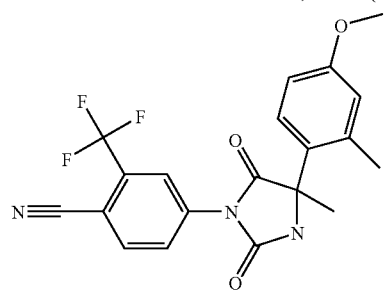

Example M

4-[2,5-dioxo-4-(4-methoxy-2-methylphenyl)-4-methylimidazolidin-1-yl]-2-trifluoromethylbenzonitrile
Yd=80%

1H-NMR (MeOD): δ 2.0 (s, 3H, Me); 2.29 (s, 3H, PhMe); 3.81 (s, 3H, OMe); 6.83 (m, 2 HAr); 7.53 (d, 1 HAr); 8.13 (AB, 2 HAr); 8.21 (s, 1 HAr).

LC/MS Gradient 1: Rt: 5.31 min; 402– (M–H)–

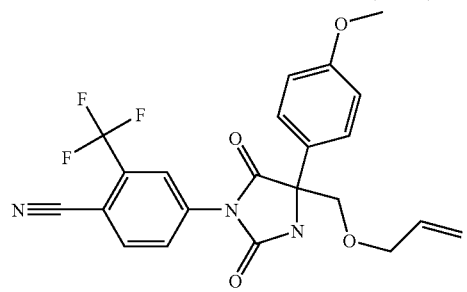

Example N

4-[2,5-dioxo-4-(4-methoxyphenyl)-4-[(2-propenyloxy)methyl]imidazolidin-1-yl]-2-trifluoromethylbenzonitrile Yd=71%

1H-NMR (CDCl3): δ 3.85 (s, 3H, OMe); 3.77 and 4.17 (2d, 2H, CH2O); 4.07 (d, 2H, CH2OCH=); 5.21 (d, 1H, C H2=CH); 5.26 (d, 1H, CH2=CH); 5.85 (m, 1H, CH2=CH); 6.13 (s, 1H, NH); 6.98 (d, 2 HAr); 7.53 (d, 2 HAr); 7.94 (m, 2 HAr); 8.08 (1 HAr).

LC/MS Gradient 1: Rt: 3.56 min; 444– (M–H)–

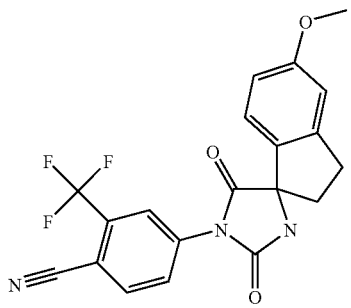

Example O

4-[2',3'-dihydro-2,5-dioxo-5'-methoxyspiro(imidazolidin-4,1'(1H)inden)-1-yl]-2-trifluoromethylbenzonitrile; quantitative Yd 1H-NMR (CDCl3): δ 2.40, 2.86, 3.12 and 3.28 (4 m, 4H, les CH2); 3.82 (s, 3H, OCH3); 5.88 (sl, 1H, NH); 6.85 (d, 1 HAr); 6.89 (s, 1 HAr); 7.12 (d, 1 HAr); 7.92 (d, 1 HAr); 8.02 (d, 1 HAr); 8.18 (s, 1 HAr).

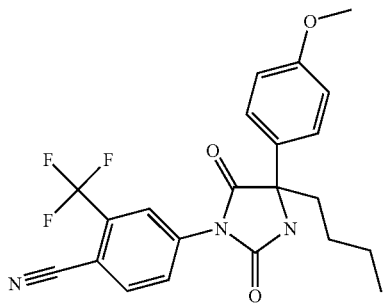

Example P

4-[4-butyl-2,5-dioxo-4-(4-methoxyphenyl)imidazolidin-1-yl]-2-trifluoromethylbenzonitrile Yd=53%

1H-NMR (CDCl3): δ 0.91 (t, 3H, CH3CH2); 1.27 and 1.38 (2m, 4H, CH3CH2CH2); 2.18 and 2.31 (2m, 2H, CH2C); 3.84 (s, 3H, OCH3); 6.0 (s, 1H, NH); 6.98 (d, 2 HAr); 7.5 (d, 2 HAr); 7.94 (AB, 2 HAr); 8.1 (s, 1 HAr).

LC/MS Gradient 1: Rt: 5.37 min; 473+ (MH+CH3CN)+

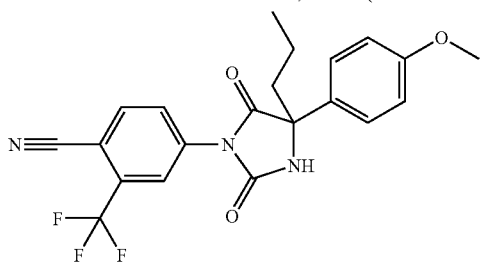

Example P-1

4-[4-propyl-2,5-dioxo-4-(4-methoxyphenyl)imidazolidin-1-yl]-2-trifluoromethylbenzonitrile Yd=91%

1H-NMR (CDCl3): δ 1.0 (t, 3H, Me); 1.35 (m, 2H, CH2); 2.15 et 2.3 (2m, 2H, CH2); 3.82 (s, 3H, OMe); 6.45 (s, 1H, NH); 6.98 (d, 2 HAr); 7.5 (d, 2 HAr); 7.91 (d, 1 HAr); 7.95 (dd, 1 HAr); 8.1 (d, 1 HAr).

LC/MS Gradient 1: Rt: 5.4 min; 416– (M–H)–

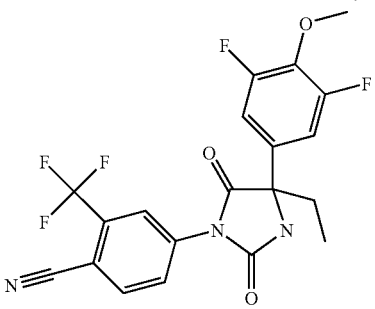

Example Q

4-[2,5-dioxo-4-ethyl-4-(3,5-difluoro-4-methoxyphenyl)imidazolidin-1-yl]-2-trifluoromethylbenzonitrile Yd=67%

LC/MS Gradient 1: Rt: 6.16 min; 438– (M–H)–

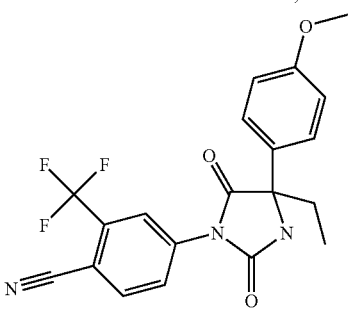

Example R

4-[2,5-dioxo-4-ethyl-4-(4-methoxyphenyl)imidazolidin-1-yl]-2-trifluoromethylbenzonitrile Yd=84%

1H-NMR (MeOD): δ 0.94 (t, 3H, CH3 Et); 1.84 and 2.04 (2 m, 2H, CH2 Et); 3.79 (s, 3H, OMe); 6.96 (d, 2 HAr); 7.51 (d, 2 HAr); 7.98 (dd, 1 HAr); 8.07 (d, 1 HAr); 8.11 (s, 1 HAr).

LC/MS Gradient 1: Rt: 5.49 min; 402– (M–H)–

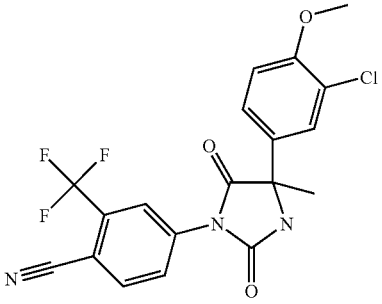

Example S

4-[4-(3-chloro-4-methoxyphenyl)-2,5-dioxo-4-methylimidazolidin-1-yl]-2-trifluoromethylbenzonitrile
Yd=65%

1H-NMR (CDCl3): δ 1.97 (s, 3H, Me); 3.94 (s, 3H, OMe); 6.23 (sl, 1H, NH); 6.96 and 7.0 (2d 10/90, 1 HAr); 7.43 and 7.49 (2 dl 90/10, 1 HAr); 7.58 and 7.74 (2 sl 90/10, 1 HAr); 7.96 (AB, 2 HAr); 8.11 (sl, 1 HAr).
LC/MS Gradient 1: Rt: 5.53 min; 422/424− (M−H)−

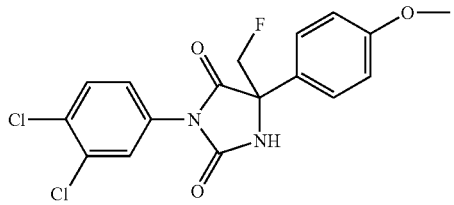

Example T

1-(3,4-dichlorophenyl)-4-fluoromethyl-4-(4-methoxyphenyl)imidazolidine-2,5-dione 0.917 g of 4-fluoromethyl-4-(4-methoxyphenyl)imidazolidine-2,5-dione and 1.06 g of 1,2-dichloro-4-iodobenzene are heated to 150° C. with 0.33 g of cuprous oxide in 3.85 mL of dimethylacetamide for 21 hours under nitrogen. After extraction with 50% ethyl acetate/ammonia then washing with a saturated aqueous sodium chloride solution, drying over sodium sulphate and concentration, the residue (brown oil, 1.52 g) is purified over a silica column with 100/0 to 70/30 heptane/ethyl acetate to yield 0.984 g of product (beige powder, Yd=67%).
TLC: Fr=0.51 (50/50 heptane/ethyl acetate).
1H-NMR (CDCl3): δ 3.75 (s, 3H, OMe); 4.48 and 4.97 (2dd, J=13 and 61 Hz, 2H, CH2F); 6.67 (s, 1H, CONH); 6.90 (d, 2 HAr); 7.25 (dd, 1 HAr); 7.45 (m, 3 HAr); 7.52 (d, 1 HAr).
LC/MS Gradient 1: Rt: 6.32 min; 381/383− (M−H)−

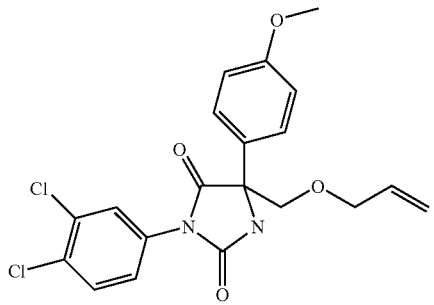

Example U

1-(3,4-dichlorophenyl)-4-(4-methoxyphenyl)-4-[(2-propenyloxy)methyl]imidazolidine-2,5-dione The procedure of Example T is used with 4-(4-methoxyphenyl)-4-[(2-propenyloxy)methyl]imidazolidine-2,5-dione and 1,2-dichloro-4-iodobenzene; Yd=60%.
1H-NMR (DMSO D6): δ 3.83 (s, 3H, OMe); 3.76 and 4.13 (2d, 2H, CH2); 4.07 (d, 2H, OCH2CH=); 5.21 (d, 1H, CH=CH2); 5.25 (d, 1H, CH=CH2); 5.85 (m, 1H, C H=CH2); 6.18 (s, 1H, NH); 6.86 (d, 2 HAr); 7.32 (d, 1 HAr); 7.53 (m, 3 HAr); 7.60 (s, 1 HAr).
LC/MS Gradient 1: Rt: 3.72 min; 462+ (MH+CH3CN)+
Intermediates II

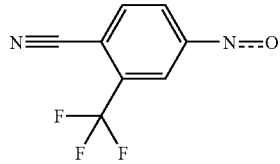

Example V

4-cyano-3-trifluoromethylphenyl isocyanate 21.16 g of triphosgene are dissolved in 100 mL of anhydrous toluene in a 500 mL four-neck bottle equipped with a nitrogen intake, a magnetic stirrer, a condenser and a guard filled with 2 N sodium hydroxide. A solution of 20 g of 4-amino-2-trifluoromethylbenzonitrile in 125 mL of anhydrous dioxan is added dropwise at ambient temperature in 1 hour 30 min. The mixture is heated to 110° C. Pronounced release of gas for 1 hour then appearance of an insoluble brown substance. After 2 hours under reflux, stirring is maintained overnight at AT. The insoluble matter is filtered and rinsed with toluene. The filtrate is concentrated in order to obtain 21.8 g of expected product (Yd=96%). The product is stored in solution in THF (2 M) in a refrigerator.
TLC: Product deposited in solution in methanol: Fr=0.45 (50/50 heptane/ethyl acetate).

Examples W to Z and AA to AO

The above methodology is used to prepare the following products (the product is deposited in solution in methanol for the TLCs):
W: 4-cyanonaphthyl isocyanate; Fr=0.38 (60/40 heptane/ethyl acetate).
X: 4-chloronaphthyl isocyanate; Fr=0.8 (60/40 petroleum ether/ethyl acetate).
Y: 7-cyanoindan-4-yl isocyanate; Fr=0.62 (60/40 petroleum ether/ethyl acetate).
Z: 4-cyano-5,6,7,8-tetrahydronaphthyl isocyanate; Fr=0.79 (30/70 heptane/ethyl acetate).
AA: 4-cyano-2,3-ethylenedioxyphenyl isocyanate; Fr=0.48 (30/70 heptane/ethyl acetate).
AB: 4-cyano-2-methylphenyl isocyanate; Fr=0.58 (40/60 heptane/ethyl acetate).
AC: 4-cyano-2-ethylphenyl isocyanate; Fr=0.28 (30/70 heptane/ethyl acetate).
AD: 2-methyl-4-nitrophenyl isocyanate; Fr=0.25 (40/60 heptane/ethyl acetate).
AE: 4-chloro-2-methylphenyl isocyanate; Fr=0.33 (40/60 heptane/ethyl acetate).
AF: 4-bromo-2-methylphenyl isocyanate; Fr=0.3 (40/60 heptane/ethyl acetate).
AG: 4-bromo-2-trifluoromethylphenyl isocyanate; Fr=0.45 (40/60 heptane/ethyl acetate).
AH: 2-chloro-4-trifluoromethylphenyl isocyanate; Fr=0.45 (40/60 heptane/ethyl acetate).
AI: 2,3,4-trichlorophenol isocyanate; Fr=0.43 (40/60 heptane/ethyl acetate).
AJ: 4-trifluoromethoxyphenyl isocyanate; Fr=0.35 (40/60 heptane/ethyl acetate).

AK: 3-chloro-4-cyano-2-methylphenyl isocyanate; Fr=0.41 (50/50 heptane/ethyl acetate).

AL: 4-cyano-2-methyl-3-trifluoromethylphenyl isocyanate; Fr=0.53 (50/50 heptane/ethyl acetate).

AM: 4-cyano-3-methoxyphenyl isocyanate; Fr=0.31 (50/50 heptane/ethyl acetate).

AN: 4-cyano-3-trifluoromethylphenyl isothiocyanate

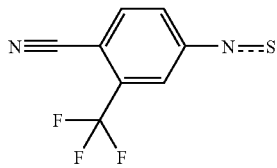

100 mL of water and 4.5 mL of thiophosgene are introduced into a 250 mL four-neck bottle equipped with a nitrogen intake, a magnetic stirrer, a condenser and a guard filled with sodium hypochlorite solution (40 mL of 47-50% Javel water, 50 mL of 10 N aqueous sodium hydroxide and 910 mL of distilled water) at ambient temperature (release of gas; heterogeneous orange solution). 9.5 g of 4-amino-2-trifluoromethylbenzonitrile are added in three batches at ambient temperature. After 3 hours of vigorous stirring at ambient temperature, the product is extracted with ethyl acetate. It is washed with an aqueous 2 N hydrochloric acid solution and a saturated aqueous NaCl solution, and the organic phases are dried over magnesium sulphate. The residue is concentrated and purified (12 g) over a silica column with 90/10 heptane/ethyl acetate. 10 g of a pale yellow solid are obtained after concentration and drying (Yd=86%).

TLC: Fr=0.8 (50/50 heptane/ethyl acetate).

1H-NMR (CDCl3): δ 7.5 (m, 1H); 7.6 (s, 1H); 7.89 (d, 1H).

Intermediates III

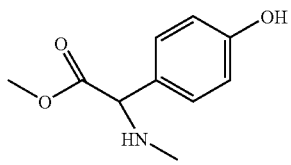

Example AP

Methyl 2-(4-hydroxyphenyl)-2-methylaminoacetate 4 g of methyl 2-(4-acetoxyphenyl)-2-bromo acetate are dissolved in 50 mL of THF in a 250 mL flask equipped with a magnetic stirrer. 25 mL of methylamine (33% in ethanol) are added: exothermic reaction. After 3 hours of stirring at ambient temperature, the insoluble matter is filtered then the filtrate is concentrated. The residue is purified over a silica column with pure ethyl acetate to yield 2.3 g of expected product (oil, Yd=86%).

1H-NMR (DMSO D6): δ 2.2 (s, 3H, NMe); 3.6 (s, 3H, OMe); 4.12 (s, 1H, NCHCO); 6.7 (d, 2 HAr); 7.15 (d, 2 HAr).

Examples AQ to AZ and BA to BD

Similar methodology is used in order to obtain the following products, by reacting the appropriate amine with methyl 2-(4-acetoxyphenyl)-2-bromo acetate:

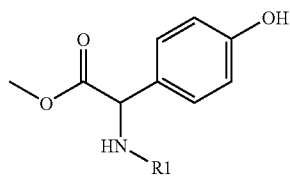

AQ: Methyl 2-(4-hydroxyphenyl)-2-propylaminoacetate

1H-NMR (CDCl3): 0.90 (t, 3H, Me); 1.60 (m, 2H, CCH2C); 2.55 (m, 2H, NCH2); 3.7 (s, 3H, OMe); 4.3 (s, 1H, NCHCO); 6.6 (d, 2 HAr); 7.15 (d, 2 HAr).

AR: Methyl 2-(4-hydroxyphenyl)-2-(2-propenyl)aminoacetate

1H-NMR (CDCl3): 3.2 (m, 2H, NCH2); 3.7 (s, 3H, OMe); 4.38 (s, 1H, NCHCO); 5.2 (m, 2H, CH2=CH); 5.9 (m, 1H, CH2=CH); 6.7 (d, 2 HAr); 7.15 (d, 2 HAr).

AS: Methyl 2-(4-hydroxyphenyl)-2-(2-propynyl)aminoacetate

1H-NMR (CDCl3): 2.3 (sl, 1H, HC≡); 3.4 (split AB, 2H, CH2N); 3.7 (s, 3H, OMe); 4.6 (s, 1H, NCHCO); 6.8 (d, 2 HAr); 7.22 (d, 2 HAr).

AT: Methyl 2-[2-(ethoxycarbonyl)ethyl]amino-2-(4-hydroxyphenyl)acetate

1H-NMR (DMSO D6): 1.18 (t, 3H, CH3CH2); 2.8 (m, 2H, CH2CO); 2.9 and 3.05 (2m, 2H, NCH2); 3.7 (s, 3H, OCH3); 4.05 (q, 2H, OCH2); 5.2 (s, 1H, NCHCO); 6.85 (d, 2 HAr); 7.35 (d, 2 HAr).

AU: Methyl 2-(3-ethoxypropyl)amino-2-(4-hydroxyphenyl)acetate

1H-NMR (CDCl3): 1.2 (t, 3H, CH3CH2); 1.8 (m, 2H, CH2); 2.65 (m, 2H, NCH2); 3.5 (m, 4H, OCH2); 3.7 (s, 3H, OMe); 4.3 (s, 1H, NCHCO); 6.6 (d, 2 HAr); 7.1 (d, 2 HAr).

AV: Methyl 2-(cyanomethyl)amino-2-(4-hydroxyphenyl)acetate

1H-NMR (CDCl3): 3.4 and 3.68 (2d, 2H, J=17 Hz, CH2CN); 3.7 (s, 3H, OMe); 4.5 (s, 1H, NCHCO); 6.8 (d, 2 HAr); 7.15 (d, 1 HAr).

AW: Methyl 2-(4-hydroxyphenyl)-2-[(3,4-methylenedioxy)phenyl]methylaminoacetate

1H-NMR (CDCl3): 3.65 (d, 2H, J=3.5 Hz, NCH2); 3.7 (s, 3H, OMe); 4.3 (s, 1H, NCHCO); 5.95 (s, 2H, OCH2O); 6.72 (m, 4 HAr); 6.85 (s, 1 HAr); 7.2 (d, 2 HAr).

AX: Methyl 2-(4-hydroxyphenyl)-2-[(4-hydroxy-3-methoxy)phenyl]methylaminoacetate 1H-NMR (DMSO D6): 3.5 (s, 2H, NCH2); 3.6 (s, 3H, PhOMe); 3.72 (s, 3H, OMe); 4.2 (s, 1H, NCHCO); 6.68 (m, 4 HAr); 6.8 (s, 1 HAr); 7.15 (d, 2 HAr).

AY: Methyl 2-(dimethylamino)ethylamino-2-(4-hydroxyphenyl)acetate

1H-NMR (CDCl3): 2.3 (s, 6H, NMe2); 2.5, 2.6 and 2.7 (3m, 4H, 2 CH2N); 3.7 (s, 3H, OMe); 4.3 (s, 1H, NCHCO); 6.55 (d, 2 HAr); 7.05 (d, 2 HAr).

AZ: Methyl 2-[(2-cyanoethyl)amino]-2-(4-hydroxyphenyl)acetate

1H-NMR (CDCl3): 2.5 (t, 2H, CH2CN); 2.81 and 2.95 (2m, 2H, NCH2); 3.7 (s, 3H, OMe); 4.9 (s, 1H, NCHCO); 6.8 (d, 2 HAr); 7.2 (d, 2 HAr).

BA: Methyl 2-(4-hydroxybutyl)amino-2-(4-hydroxyphenyl)acetate

1H-NMR (CDCl3): δ 1.7 (m, 2H, CH2CH2N); 2.15 (m, 2H, CH2CH2O); 3.15 (m, 2H, CH2N); 3.7 (s, 3H, OMe); 4.1 (m, 2H, CH2O); 5.42 (d, 1H, NCHCO); 6.75 (d, 2 HAr); 7.2 (d, 1 HAr).

BB: Methyl 2-(2-hydroxyethyl)amino-2-(4-hydroxyphenyl)acetate

1H-NMR (CDCl3): δ 2.75 (m, 2H, NCH2); 3.65 (m, 2H, CH2O); 3.7 (s, 3H, OMe); 4.32 (s, 1H, NCHCO); 6.7 (d, 2 HAr); 7.2 (d, 1 HAr).

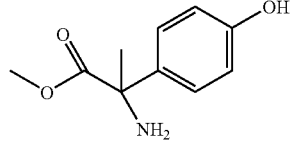

BC: Methyl 2-amino-2-(4-hydroxyphenyl)propionate 10 g of methyl 2-(4-acetoxyphenyl)-2-bromopropionate, 50 mL of THF and 30 mL of ethanol are introduced into a Woulff bottle at ambient temperature. The mixture is saturated with gaseous ammonia and stirred for one night at ambient temperature. The insoluble matter is filtered and purified over a silica column with 90/10 dichloromethane/methanol to yield the product (5 g; Yd=77%).

1H-RMN (CDCl3): δ 1.7 (s, 3H, Me); 3.7 (s, 3H, OMe); 6.7 (d, 2 HAr); 7.25 (d, 1 HAr).

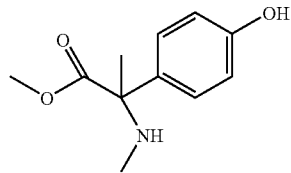

BD: Methyl 2-(4-hydroxyphenyl)-2-methylaminopropionate 8.12 g of methyl 2-(4-acetoxyphenyl)-2-bromopropionate and 160 mL of THF are introduced into a flask at ambient temperature. 40 mL of a saturated solution of methylamine in ethanol are added. The mixture becomes pale yellow with formation of an insoluble substance. After 30 min at ambient temperature, the mixture is filtered, rinsed with THF and concentrated. The residue (yellow oil, 9.1 g) is purified over a silica column while eluting with 95/5 dichloromethane/methanol to yield a pale yellow oil which crystallises in isopropyl ether. After filtration and drying, the product is obtained (2.46 g in the form of a white powder and 2 g in the form of a pale yellow oil; Yd=79%).

TLC: Fr=0.25 (95/5 dichloromethane/methanol).

1H-NMR (CDCl3): δ 1.65 (s, 3H, Me); 2.3 (s, 3H, NMe2); 3.7 (s, 3H, OMe); 6.8 (d, 2 HAr); 7.22 (d, 2 HAr).

LC/MS Gradient 1: Rt: 1.01 min; 179+ (M−MeNH)+

Examples BE to BG

Using similar methodology and starting from methyl 2-(4-acetoxyphenyl)-2-bromopropionate and the appropriate amine, the following products are prepared:

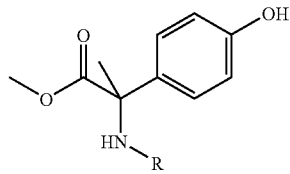

BE: Methyl 2-(4-hydroxyphenyl)-2-(2-propynyl)aminopropionate

LC/MS Gradient 1: Rt: 1.09 min; 234+ (MH)+

BF: Methyl 2-(4-hydroxybutyl)amino-2-(4-hydroxyphenyl)propionate

1H-NMR (CDCl3): δ 1.60 (m, 2H, CH2CH2N); 1.70 (s, 3H, Me); 1.80 (m, 2H, CH2CH2O); 2.60 (m, 2H, CH2N); 3.65 (m, 2H, CH2O); 3.76 (s, 3H, OMe); 6.69 (d, 2 HAr); 7.15 (d, 2 HAr).

LC/MS Gradient 1: Rt: 1.02 min; 266− (M−H)−

BG: Methyl 2-(4-hydroxyphenyl)-2-(2-propenyl)aminopropionate

1H-NMR (MeOD): δ 1.55 (s, 3H, Me); 2.91 (t, 1H, CH2N); 3.59 (s, 3H, OMe); 4.96 (d, J=10 Hz, 1H, C=CH2); 5.04 (d, J=15 Hz, 1H, C=CH2); 5.8 (m, 1H, CH=C); 6.65 (d, 2 HAr); 7.13 (d, 2 HAr).

LC/MS Gradient 1: Rt: 0.91 min; 236+ (MH)+

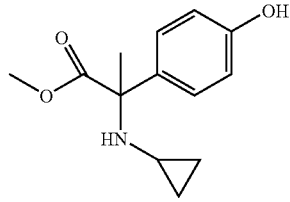

BG-1

Methyl 2-(4-hydroxyphenyl)-2-cyclopropylaminoacetate

1H-NMR (DMSO D6): δ 0.25 and 0.4 (2m, 4H, 2 CH2); 1.55 (s, 3H, Me); 1.8 (m, 1H, CHN); 3.05 (sl, 1H, NH); 3.65

(s, 3H, OMe); 6.7 (d, 2 HAr); 7.15 (d, 2 HAr); 9.35 (s, 1H, OH).

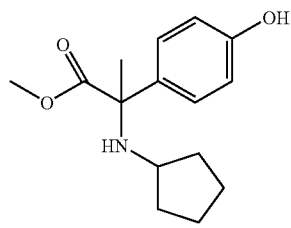

BG-2

Methyl 2-(4-hydroxyphenyl)-2-cyclopentylaminoacetate

1H-NMR (DMSO D6): δ 1.22 and 1.38 (2m, 4H, 2 CH2); 1.48 (s, 3H, Me); 1.58 and 1.7 (2m, 4H, 2 CH2CHN); 2.28 (sl, 1H, NH); 2.84 (m, 1H, CHN); 3.6 (s, 3H, OMe); 6.7 (d, 2 HAr); 7.18 (d, 2 HAr); 9.33 (s, 1H, OH).

Examples BH to BO

The following amino esters are also prepared by similar methodology:
BH: Methyl 2-[2-(ethoxycarbonyl)ethyl]amino-2-(4-hydroxyphenyl)propionate;
BI: Methyl 2-[(2-cyanoethyl)amino]-2-(4-hydroxyphenyl)propionate;
BJ: Methyl 2-(2-hydroxyethyl)amino-2-(4-hydroxyphenyl)propionate;
BK: Methyl 2-(4-hydroxyphenyl)-2-(3-hydroxypropyl)aminopropionate;
BL: Methyl 2-(4-hydroxyphenyl)-2-(4-methoxyphenyl)aminopropionate;

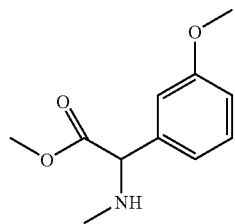

BM: Methyl 2-(3-methoxyphenyl)-2-methylaminoacetate

Starting from 14.5 g of methyl 2-bromo-2-(3-methoxyphenyl)acetate, 7.5 g of product are prepared by the process used above when preparing methyl 2-(4-hydroxyphenyl)-2-methylaminopropionate (yellow oil; Yd=65%).
1H-RMN (CDCl3): δ 2.4 (s, 3H, NMe); 3.7 (s, 3H, OMe); 3.8 (s, 3H, COOMe); 4.75 (s, 1H, NCHCO); 6.85 (dd, 1 HAr); 6.96 (m, 2 HAr); 7.27 (m, 1 HAr).

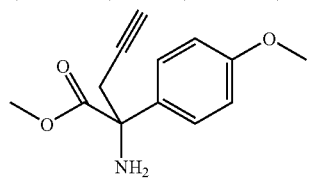

Example BM-1

Methyl 2-amino-2-(4-hydroxyphenyl)-4-pentynoate

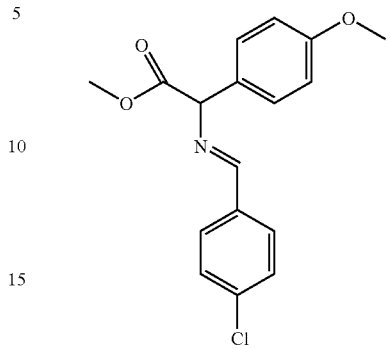

Stage 1

Methyl 2-[(4-chlorophenyl)methylene]amino-2-(4-methoxyphenyl)acetate 998 mg of methyl 2-amino-2-(4-methoxyphenyl)acetate (prepared according to M. A. Sierra Rodrigez et al, Int. Pat. Appl. WO 02/102762) are dissolved in 30 mL of dichloromethane. 1 g of magnesium sulphate is added along with 717 mg of 4-chlorobenzaldehyde. The mixture is stirred at AT for 21 hours, the solid is filtered off, the filtrate is washed with dichloromethane then the solvent is dried over magnesium sulphate and evaporated to produce 1.65 g of an oil. The crude product is purified by chromatography over silica gel while eluting with the 90/10/1 then 80/20/1 heptane/ethyl acetate/triethylamine mixture. 1.24 g of colourless oil is obtained which crystallises on cooling (Yd=76%).
1H-NMR (CDCl3): δ 3.75 and 3.82 (2s, 6H, 2OMe); 5.18 (s, 1H, NCHCO); 6.93 (d, 2 HAr); 7.43 (AB, 4 HAr); 7.78 (d, 2 HAr); 8.29 (s, 1H, N=CH).

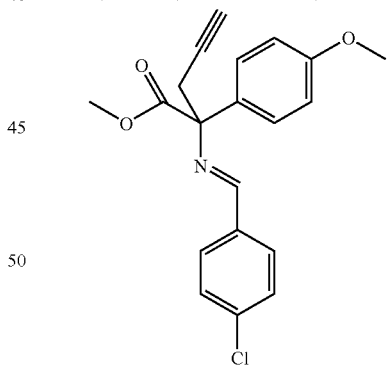

Stage 2

Methyl 2-[(4-chlorophenyl)methylene]amino-2-(4-methoxyphenyl)-4-pentynoate

A solution of 1.24 g of the compound prepared in Stage 1, 0.53 mL of propargyl bromide and 132 mg of tetrabutyl ammonium hydrogenosulphate in 12.5 mL of dichloromethane is added to 9 mL of a 10 N aqueous sodium hydroxide solution. The mixture is vigorously stirred at AT for 1 hour then it is diluted with water and the product is extracted with dichloromethane. The solvent is dried over magnesium sulphate and evaporated to produce 1.68 g of a yellow oil which is purified by chromatography over silica gel while eluting with the 85/5/1 heptane/ethyl acetate/triethylamine mixture. 962 mg of slightly yellow oil is obtained (Yd=69%).

1H-NMR (CDCl3): δ 2.00 (s, 1H, CH); 3.08 and 3.27 (AB, 2H, CH2); 3.79 and 3.84 (2s, 6H, 2OMe); 6.93 (d, 2 HAr); 7.43 (d, 4 HAr); 7.08 (d, 2 HAr); 8.25 (s, 1H, N=CH).

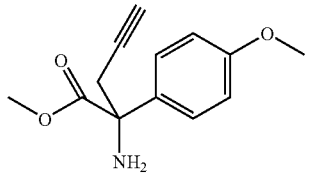

Stage 3

Methyl 2-amino-2-(4-methoxyphenyl)-4-pentynoate 962 mg of the compound prepared in Stage 2 are stirred at AT in 14 mL of ethyl ether and 3.5 mL of 1 N hydrochloric acid for 18 hours. The mixture is diluted with water and the product is extracted with ethyl acetate. The solvent is dried over magnesium sulphate and evaporated to produce 584 mg of product, in the form of colourless oil (Yd=92%).

1H-NMR (CDCl3): δ 2.08 (s, 1H, CH); 2.50 (sl, 1H, NH2); 2.82 and 3.15 (AB, 2H, CH2); 3.77 and 3.82 (2s, 6H, 2OMe); 6.90 (d, 2 HAr); 7.47 (d, 2 HAr).

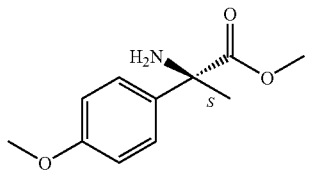

BO:
Methyl(S)-2-amino-2-(4-methoxyphenyl)propionate

The preparation of ethyl(S)-2-amino-2-(4-methoxyphenyl)propionate is described by W. N. Washburn et al. in Bioorg. Med. Chem. Letters, 14 (2004), 3525-3529 and by P. T. W. Cheng et al. in U.S. Pat. No. 5,770,615. Methyl(S)-2-amino-2-(4-methoxyphenyl)propionate is prepared by adapting this method.

With this method, starting from 4.3 g of (RS)-2-acetylamino-2-(4-methoxyphenyl)-propanoic acid, using (S)-(+)-α-methylbenzylamine for resolution and a saturated solution of hydrogen chloride in methanol (instead of hydrochloric ethanol), 3 g of product are obtained in the form of white crystals (Yd=77%).

[α]D=+40.3° (c=1%, MeOH).
TLC: Fr=0.50 (ethyl acetate).
1H-NMR (MeOD): δ 1.70 (s, 3H, Me); 3.69 (s, 3H, MeOCO); 3.80 (s, 3H, MeOPh); 6.90 (d, 2 HAr); 7.40 (d, 2 HAr).
LC/MS Gradient 1: Rt: 0.81 min; 194+ (MH−NH3)+

Methyl(R)-2-amino-2-(4-methoxyphenyl)propionate

The process for preparing the enantiomer S is used, resolution being conducted with R)-(+)-α-methylbenzylamine.

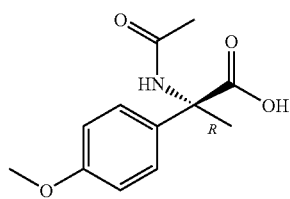

Stage 1

(R)-2-acetylamino-2-(4-methoxyphenyl)propanoic acid 14.17 mL of (R)-(+)-α-methylbenzylamine are added to 26 g of (RS)-2-acetylamino-2-(4-methoxyphenyl)propanoic acid in suspension in 1300 mL of ethanol. The mixture is left for 15 hours at AT with magnetic stirring and a few seeds are added. Crystallisation of the expected product is accelerated. After an additional 24 hours the insoluble matter is filtered, rinsed with a little ethanol then washed with ether. The mixture is dried under vacuum and 13 g of crystals are obtained and suspended in 200 mL of water. An aqueous 2 N hydrochloric acid solution is added until a pH of 1 is reached, then the mixture is stirred for 45 min at ambient temperature, and the insoluble matter is filtered and rinsed with a small amount of water. After drying under vacuum, 8 g of product are obtained in the form of a white solid (Yd=30.7%).

[α]D=−88.0° (c=0.4%, phosphate buffer pH 7).
1H-NMR (MeOD): δ 1.90 (s, 3H, Me); 2.00 (s, 3H, MeCO); 3.80 (s, 3H, MeO); 6.90 (d, 2 HAr); 7.45 (d, 2 HAr).
LC/MS Gradient 1: Rt: 1.22 min; 260+ (M++Na)+

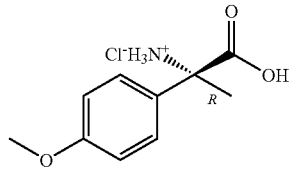

Stage 2

(R)-1-carboxy-1-(4-methoxyphenyl)ethyl ammonium hydrochloride 7.8 g of (R)-2-acetylamino-2-(4-methoxyphenyl)propanoic acid are suspended in 90 mL of an aqueous 4 N hydrochloric acid solution. The mixture is heated under reflux for 3 hours (solubilisation of the product formed) then left to return to AT and evaporated to dryness by taking up with ethanol. The mixture is dried under vacuum in order to obtain 7.6 g of product in the form of a white solid (quantitative Yd).

[α]D=−71.2° (c=1%, HCl 1N).
1H-RMN (D2O): δ 1.90 (s, 3H, Me); 3.78 (s, 3H, MeO); 7.00 (d, 2 HAr); 7.40 (d, 2 HAr).
LC/MS Gradient 1: Rt: 0.84 min; 194− (MH−HCl)−

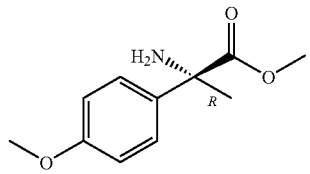

Stage 3

Methyl(R)-2-amino-2-(4-methoxyphenyl)propionate 7.6 g of (R)-1-carboxy-1-(4-methoxyphenyl)ethyl ammonium hydrochloride are dissolved in 90 mL of methanol. The solution is cooled to 0° C. and is saturated with gaseous hydrogen chloride for 20 min. It is then stirred for 1 hour at AT, then under reflux of methanol for 15 hours. After evaporation to dryness, the product is taken up with a saturated aqueous sodium bicarbonate solution then extracted with ethyl acetate. The organic phases are dried over magnesium sulphate, filtered and concentrated to dryness. The residue is purified by chromatography over silica while eluting with a 1/1 heptane/ethyl acetate mixture then with pure ethyl acetate to yield 5.8 g of product in the form of white crystals (Yd=84%).

[α]D=−39.3° (c=1%, MeOH).

TLC: Fr=0.50 (ethyl acetate)

1H-NMR (MeOD): δ 1.70 (s, 3H, Me); 3.67 (s, 2H, MeOCO); 3.78 (s, 3H, MeOPh); 6.93 (d, 2 HAr); 7.42 (d, 2 HAr).

LC/MS Gradient 1: Rt: 0.81 min; 194+ (MH−NH3)+

BO-1

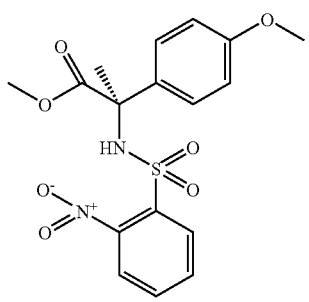

Stage 1

Methyl(R)-2-(4-methoxyphenyl)-2-(2-nitrophenyl)sulphonylaminopropionate 2.2 g of (2-nitrophenyl)sulphonyl chloride are added to a solution of 1.6 g of methyl(R)-2-amino-2-(4-methoxyphenyl)propionate in 50 mL of pyridine. The mixture is stirred at AT for 0.25 h then refluxed for 1.5 h. After cooling at AT, the mixture is filtered and evaporated to dryness. The crude product is diluted with water and extracted with ethyl acetate. The organic layer is dried over magnesium sulphate, filtered and evaporated. The crude product is purified by chromatography over silica gel while eluting with 70/30 heptane/ethyl acetate. 1.2 g of yellow oil is obtained (Yd=40%).

TLC: Fr=0.55 (50/50 heptane/ethyl acetate).

1H-NMR (CDCl3): δ 2.13 (s, 3H, Me); 3.71 (s, 3H, OMe); 3.73 (s, 3H, OMe); 6.56 (d, 2 HAr); 7.17 (d, 2 HAr); 7.20 (dd, 1 HAr); 7.28 (dt, 1 HAr); 7.33 (s, 1H, NH); 7.53 (td, 1 HAr); 7.76 (dd, 1 HAr).

LC/MS Gradient 1: Rt: 5.03 min; 393− (M−H)−

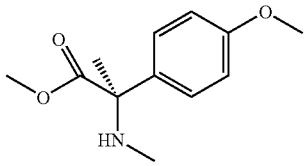

Stage 2

Methyl(R)-2-(4-methoxyphenyl)-2-methylaminopropionate 168 mg of sodium hydride (50% dispersion in mineral oil) are added to a solution of 1.2 g of methyl(R)-2-(4-methoxyphenyl)-2-(2-nitrophenyl)sulphonylaminopropionate and 0.23 mL of iodomethane in 20 mL of N,N-dimethylacetamide. The mixture is stirred at AT for 3 hours, evaporated to dryness, diluted with water and extracted with ethyl acetate. The organic layer is dried over magnesium sulphate, filtered and evaporated to dryness. 3.2 g of potassium carbonate and 0.48 mL of thiophenol are added to the crude product diluted with 20 mL of N,N-dimethylacetamide. The mixture is stirred at AT for 2 h, evaporated to dryness, diluted with water and extracted with ethyl acetate. The organic layer is dried over magnesium sulphate, filtered and evaporated to dryness. The crude product is purified by chromatography over silica gel while eluting with 50/50 heptane/ethyl acetate. 1.2 g of a yellow oil is obtained (Yd=85%).

TLC: Fr=0.15 (50/50 heptane/ethyl acetate).

1H-NMR (CDCl3): δ 2.13 (s, 3H, Me); 2.29 (s, 3H, NMe); 3.72 (s, 3H, OMe); 3.81 (s, 3H, OMe); 6.87 (d, 2 HAr); 7.36 (d, 2 HAr).

LC/MS Gradient 1: Rt: 0.90 min; no ionisation

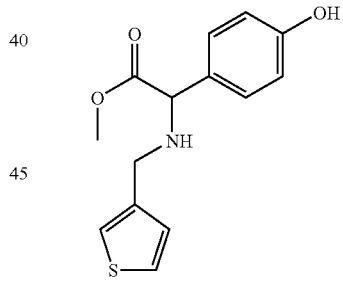

BP: Methyl 2-(4-hydroxyphenyl)-2-[(thiophen-3-yl)methylamino]acetate 5 g of methyl(R)-amino-(4-hydroxyphenyl)acetate hydrochloride and 100 mL of anhydrous ethyl acetate (thick suspension) are introduced at ambient temperature into a 500 mL Woulff bottle equipped with a nitrogen intake, a magnetic stirrer and a condenser. 3.1 mL of triethylamine, some magnesium sulphate and 3 g of thiophene-3-carbaldehyde are added. After 4 hours under reflux, the white solid is filtered, washed with ethyl acetate and dried under vacuum. The product is taken up in 100 mL of anhydrous dichloromethane. 14 g of sodium triacetoxy borohydride are added and the mixture is stirred at ambient temperature for 2 hours. 100 mL of methanol are added then the reaction mixture is concentrated. The product is extracted with ethyl acetate. It is washed with water then the organic phases are dried over magnesium sulphate. The mixture is concentrated, and the residue is purified over a silica column with 50/50 heptane/ethyl acetate. After concentration and crystallisation in isopropanol, a white solid is obtained (2.35 g; Yd=37%).

1H-NMR (CDCl3): δ 3.7 (s, 3H, OMe); 3.8 (s, 2H, NCH2); 4.35 (s, 1H, NCHCO); 6.62 (m, 2 HAr); 7.08 (d, 2 HAr); 7.15 and 7.2 (2d, H2 and H5 thiophene); 7.30 (m, H3 thiophene).

BO: 1,1-dimethylethyl 2,3-dihydro-5-methoxy-1-methyl-1H-isoindolecarboxylate

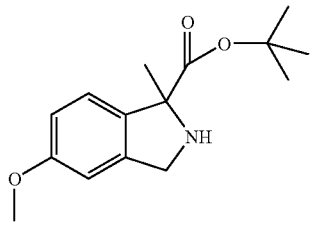

This product is prepared by the method described for the preparation of 1,1-dimethylethyl 2,3-dihydro-1-methyl-2-[(phenylmethoxy)carbonyl]-1H-isoindolecarboxylate and described by O. Gaertzen and L. Buchwald, J. Org. Chem. 67 (2002) 465-475.

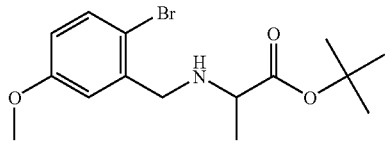

Stage 1

1,1-dimethylethyl 2-[[(2-bromo-5-methoxyphenyl)methyl]amino]propionate 1.09 g of terbutyl(L)-alaninate is dissolved in 8 mL of DMF under nitrogen at ambient temperature. 2.07 g of potassium carbonate are added then 1.68 g of benzyl bromide in solution in 4 mL of DMF are added dropwise. The reaction mixture is stirred for 20 hours at AT, then treated with water and extracted with ethyl acetate. The organic phase is washed with a saturated aqueous sodium chloride solution, dried over sodium sulphate and concentrated. The residue is purified over a silica column with 85/15 heptane/ethyl acetate to yield 1.37 g of a colourless oil (Yd=67%).

TLC: Fr=0.6 (50/50 heptane/ethyl acetate).

1H-NMR (CDCl3): δ 1.32 (d, 3H, Me); 1.49 (s, 9H, tBu); 3.3 (q, 1H, NCHCO); 3.78 and 3.90 (AB, 2H, CH2N); 3.8 (s, 3H, OMe); 6.68 (dd, 1 HAr); 7.07 (sl, 1 HAr); 7.4 (d, 1 HAr).

LC/MS Gradient 1: Rt: 2.66 min; 288/290+ (MH−tBu)+

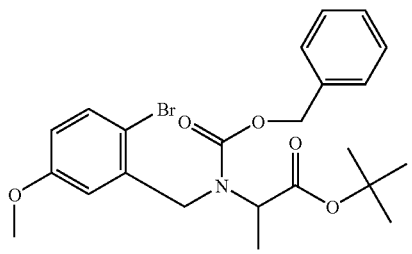

Stage 2

1,1-dimethylethyl 2-[[(2-bromo-5-methoxyphenyl)methyl][(phenylmethoxy)carbonyl]-amino]propionate 0.83 mL of diisopropylethyl amine is added to 1.36 g of 1,1-dimethylethyl 2-[[(2-bromo-5-methoxyphenyl)methyl]amino]propionate dissolved in 5 mL of dichloromethane at ambient temperature under nitrogen. 0.62 mL of benzyloxycarbonyl chloroformate is then added dropwise. After one night at ambient temperature, 0.3 mL of benzyloxycarbonyl chloroformate and 0.4 mL of diisopropylethyl amine are added again and the mixture is stirred at ambient temperature for a further 2 hours. The reaction mixture is treated with water, then extracted with ethyl acetate. The organic phase is washed with a saturated aqueous sodium chloride solution, dried over sodium sulphate and concentrated. The residue is purified over a silica column with 90/10 heptane/ethyl acetate to yield 1.72 g of a colourless oil (Yd=91%).

TLC: Fr=0.3 (90/10 heptane/ethyl acetate).

LC/MS Gradient 1: Rt: 4.71 min; 378/380+ (MH−Me2C=CH2−CO2)+; 500/502+ (M+Na)+

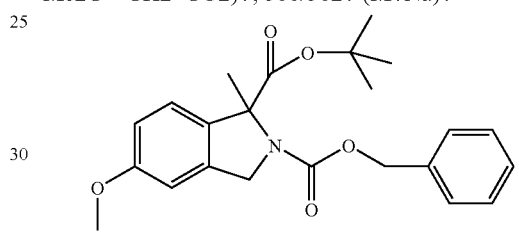

Stage 3

1,1-dimethylethyl 2,3-dihydro-5-methoxy-1-methyl-2-[(phenylmethoxy)carbonyl]-1H-isoindolecarboxylate 10 mL of dioxan are added to a mixture of 479 mg of lithium terbutylate, 62 mg of tris (dibenzylideneacetone)dipalladium and 57 mg of 2-diphenylphosphino-2'-dimethylamino-biphenyl at ambient temperature under argon. 1.43 g of 1,1-dimethylethyl 2-[[(2-bromo-5-methoxyphenyl)methyl][(phenylmethoxy)carbonyl]amino]propionate dissolved in 5 mL of dioxan are then added and the mixture is stirred for 24 hours at 90° C. After filtration over Clarcel, rinsing with diethyl ether and concentration, the residue is purified over a silica column with 90/10 heptane/ethyl acetate to yield 0.688 g of a slightly yellow oil (Yd=58%).

TLC: Fr=0.5 (50/50 heptane/ethyl acetate).

LC/MS Gradient 1: Rt: 4.12 min; 298+ (MH−tBuOCO)+; 342+ (MH−tBu)+; 420+ (M+Na)+

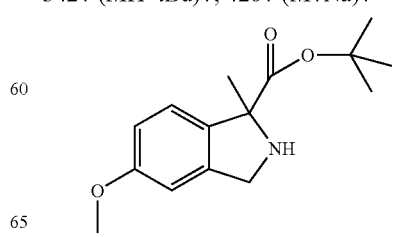

Stage 4

1,1-dimethylethyl 2,3-dihydro-5-methoxy-1-methyl-1H-isoindolecarboxylate 595 mg of 1,1-dimethylethyl 2,3-dihydro-5-methoxy-1-methyl-2-[(phenylmethoxy) carbonyl]-1H-isoindolecarboxylate are placed in 15 mL of ethanol in the presence of 150 mg of palladium (10% on charcoal). The mixture is hydrogenated at atmospheric pressure and ambient temperature while stirring. After 16 hours of reaction, the catalyst is filtered over Clarcel and the filtrate is evaporated. The residue is purified over a silica column with 80/20 to 50/50 heptane/ethyl acetate to yield 371 mg of product in the form of an oil (Yd=94%).

TLC: Fr=0.2 (50/50 heptane/ethyl acetate).

1H-NMR (CDCl3): δ 1.45 (s, 9H, tBu); 1.61 (s, 3H, Me); 4.2 and 4.35 (AB, J=13 Hz, 2H, CH2N); 3.8 (s, 3H, OMe); 6.72 (s, 1 HAr); 6.8 (dl, 1 HAr); 7.29 (d, 1 HAr).

LC/MS Gradient 1: Rt: 2.20 min; 208+ (MH–Me2C═CH2)

Intermediates VII

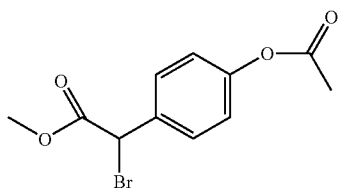

Example BR

Methyl 2-(4-acetoxyphenyl)-2-bromoacetate 9.5 g of NBS and 0.7 g of AIBN are added to a solution of 10 g of methyl(4-acetoxyphenyl)acetate in 100 mL of carbon tetrachloride in a 500 mL flask equipped with a magnetic stirrer and a condenser. After 16 hours under reflux, the mixture is filtered, the solid is washed with dichloromethane then the filtrate is concentrated. The residue is purified over a silica column with pure dichloromethane to yield 13 mg of expected product (oil, Yd=95%).

1H-NMR (CDCl3): δ 2.3 (s, 3H, COCH3); 3.8 (s, 3H, OMe); 5.4 (s, 1H, CHBr); 7.1 (d, 2 HAr); 7.6 (d, 2 HAr).

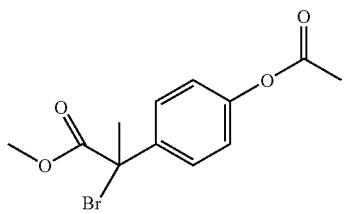

Example BS

Methyl 2-(4-acetoxyphenyl)-2-bromopropionate 42.3 g of methyl 2-(4-acetoxyphenyl)propionate and 500 mL of tetrachloromethane are introduced at ambient temperature into a Woulff bottle equipped with a condenser. 32.04 g of N-bromosuccinimide and 2.95 g of azoisobutyronitrile are added. The mixture is heated under reflux (intense red colouring, and release of bromine then decolouration. The solution becomes pale yellow). After 7 hours under reflux, the reaction is incomplete and 13.35 g of NBS and 1.23 g of azoisobutyronitrile are added, then heating under reflux is continued overnight. The mixture is filtered, rinsed with dichloromethane and concentrated. The residue is purified (brown oil, 85 g) over a silica column with 70/30 dichloromethane/heptane to yield 48.24 g of a yellow oil (Yd=100%).

TLC: Fr=0.42 (90/10 dichloromethane/heptane).

1H-NMR (MeOD): δ 2.3 (s, 6H, Me and CH3CO); 3.8 (s, 3H, OMe); 7.1 (d, 2 HAr); 7.6 (d, 2 HAr).

LC/MS Gradient 1: Rt: 1.05 min; 179+ (MH–Br–MeCO)+; 328+

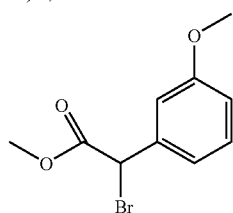

Example BT

Methyl 2-bromo-2-(3-methoxyphenyl)acetate

Starting from 10 g of methyl 2-(3-methoxyphenyl)acetate, 14.5 g of product are prepared by the method used to prepare methyl 2-(4-acetoxyphenyl)-2-bromopropionate (yellow oil; Yd=100%).

TLC: Fr:=0.5 (50/50 dichloromethane/cyclohexane).

1H-NMR (CDCl3): δ 3.8 (s, 3H, OMe); 3.85 (s, 3H, COOMe); 5.35 (s, 1H, CHBr); 6.9 (dd, 1 HAr); 7.1 (d, 1 HAr); 7.12 (s, 1 HAr); 7.27 (m, 1 HAr).

Intermediates IX

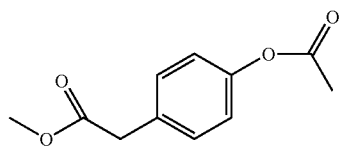

Example BU

Methyl(4-acetoxyphenyl)acetate 41.5 g of K2CO3 are added to a solution of 40 g of methyl (4-hydroxyphenyl)acetate in 800 mL of anhydrous THF in a 2 L flask equipped with a magnetic stirrer, under nitrogen. 27 mL of acetic anhydride are then added at 9° C. After 1 hour of stirring at 44° C., the insoluble matter is filtered. It is washed with THF and the filtrate is concentrated to yield 53 g of expected product (white solid). The crude product is used directly for preparing the corresponding intermediate VII.

1H-NMR (CDCl3): δ 2.3 (s, 3H, COCH3); 3.62 (s, 2H, CH2); 3.7 (s, 3H, OMe); 7.1 (d, 2 HAr); 7.6 (d, 2 HAr).

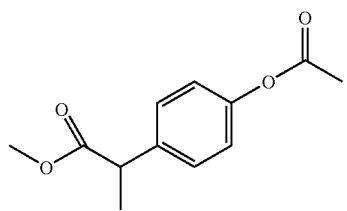

Example BV

Methyl 2-(4-acetoxyphenyl)propionate 25 g of 2-(4-hydroxyphenyl)propanoic acid and 500 mL of methanol are introduced into a four neck bottle at ambient temperature. 25 mL of thionyl chloride are added dropwise for 15 min at 0° C., exothermic reaction. After 3 hours 30 min at 0° C., the mixture is concentrated, extracted with ethyl acetate, washed with water and dried over magnesium sulphate. After concentration, 34.7 g of methyl 2-(4-hydroxyphenyl)propionate (brown oil, Yd>100%) are obtained and are used directly for preparing the corresponding intermediate VII.

TLC: Fr=0.73 (40/60 heptane/ethyl acetate)
1H-NMR (CDCl3): δ 1.5 (d, 3H, Me); 3.55 (m, 4H, CHCO and OMe); 6.7 (d, 2 HAr); 7.05 (d, 2 HAr).

34.7 g of the previous product and 450 mL of THF are introduced into a 1 L four neck bottle at ambient temperature. 31.05 g of K2CO3 are added, then 21 mL of acetic anhydride are added dropwise for 10 min at 0° C., exothermic reaction. After one night at ambient temperature, the mixture is filtered and rinsed with THF, and the filtrate is concentrated to yield 42.3 g of product (colourless oil; Yd=100%).

TLC: Fr=0.29 (80/20 dichloromethane/ethyl acetate).
1H-NMR (CDCl3): δ 1.5 (d, 3H, Me); 2.3 (s, 3H, COCH3); 3.67 (s, 3H, OMe); 3.72 (q, 1H, CHCH3); 7.05 (d, 2 HAr); 7.31 (d, 2 HAr).
LC/MS Gradient 1: Rt: 4.67 min; 223+ (MH+)+; 240+ (M+H2O)+; 264+ (M+CH3CN)+

Intermediates (X)

Example BW

2-fluoro-1-(4-methoxyphenyl)ethanone 2 g of 4-methoxyacetophenone and 9.51 g of 1-chloromethyl-4-fluoro-1,4-diazoniabicyclo[2,2,2]octane bis(tetrafluoroborate) (F-TEDA-BF4, Selectfluor®) are dissolved in 67 mL of methanol and heated for 24 hours under reflux under nitrogen. After evaporation, the residue is taken up in 200 mL of ethyl acetate, washed with 200 mL of water then with a saturated aqueous sodium chloride solution and dried over sodium sulphate. After concentration, the product is purified over a 200 g silica column with 95/5 to 89/11 heptane/ethyl acetate to yield 1.49 g of a white solid (Yd=74%).

TLC: Fr=0.26 (80/20 heptane/ethyl acetate).
1H-NMR (CDCl3): δ 3.83 (s, 3H, OMe); 5.40 (d, J=60 Hz, 2H, CH2F); 6.9 (d, J=10 Hz, 2 HAr); 7.83 (d, J=10 Hz, 2 HAr).
LC/MS Gradient 2: Rt: 1.16 min; 169+ (MH)+

Example BX

1-(4-methoxyphenyl)-2-(2-propenyloxy)ethanone

This product is prepared in the manner described in J. Org. Chem. (1983), 48, 2520-2527 and in J. Org. Chem. (1995), 60, 872-882.

Intermediates (XI)

Example BY

4-fluoromethyl-4-(4-methoxyphenyl)imidazolidine-2,5-dione 0.98 g of 2-fluoro-1-(4-methoxyphenyl)ethanone, 0.759 g of potassium cyanide and 2.66 g of ammonium carbonate are heated to 55° C. for 3 hours in 23 mL of a 50/50 ethanol/water mixture. 2.66 g of ammonium carbonate are added and heating is continued for 16 hours. The reaction mixture is diluted with water and extracted with ethyl acetate. The organic solution is washed with a saturated aqueous sodium chloride solution, then dried over sodium sulphate and evaporated to yield 1.35 g of product (whitish yellow solid, Yd=97%).

TLC: Fr=0.1 (60/40 heptane/ethyl acetate).
1H-NMR (DMSO D6): δ 3.77 (s, 3H, OMe); 4.45 and 4.93 (2dd, J=13 and 47 Hz, CH2F); 7.0 (d, J=12.5 Hz, 2 HAr); 7.48 (d, J=12.5 Hz, 2 HAr); 8.81 and 10.96 (2s, 2H, NHs).
LC/MS Gradient 2: Rt: 1.12 min; no ionisation

Examples BZ and CA to CI

Similar methodology applied to the appropriate intermediates X and with the stated reaction time leads to the following products:

BZ: 4-(2-fluoro-4-methoxyphenyl)-4-methylimidazolidine-2,5-dione

Reaction time: 169 hours; Yd=91%.
1H-NMR (DMSO D6): δ 1.67 (s, 3H, Me); 3.77 (s, 3H, OMe); 6.81 (ddd, 2 HAr); 7.40 (t, 2 HAr); 8.25 (s, 1H, CONH); 10.88 (s, 1H, CONHCO).
LC/MS Gradient 2: Rt: 1.10 min; 237− (M−H)−

CA: 4-(4-methoxyphenyl)-4-trifluoromethylimidazolidine-2,5-dione

Reaction time: 18 hours; Yd=50%.
1H-NMR (MeOD): δ 3.83 (s, 3H, OMe); 7.02 (d, 2 HAr); 7.53 (d, 2 HAr).
LC/MS Gradient 1: Rt: 2.54 min; 273− (M−H)−

CB: 4-(3-fluoro-4-methoxyphenyl)-4-methylimidazolidine-2,5-dione

Reaction time: 86 hours; Yd=96%.

1H-NMR (DMSO D6): δ 1.63 (s, 3H, Me); 3.83 (s, 3H, OMe); 7.23 (m, 3 HAr); 8.59 (s, 1H, CONH); 10.79 (s, 1H, CONHCO).
LC/MS Gradient 2: Rt: 1.42 min; 237– (M–H)–

CC: 4-Methyl-4-(2-methyl-4-methoxyphenyl)imidazolidine-2,5-dione

Reaction time: 118 hours; Yd=53%.
1H-NMR (DMSO D6): 1.71 (s, 3H, Me); 2.20 (s, 3H, PhMe); 3.73 (s, 3H, OMe); 6.77 (s, 2 HAr); 7.36 (d, 1 HAr); 8.20 (s, 1H, CONH); 10.88 (s, 1H, CONHCO).
LC/MS Gradient 2: Rt: 1.22 min; 233– (M–H)–

CD: 4-(4-methoxyphenyl)-4-[(2-propenyloxy)methyl]imidazolidine-2,5-dione

Reaction time: 26 hours; Yd=79%.
1H-NMR (MeOD): δ 3.69 (s, 3H, OMe); 3.48 and 3.95 (2d, 2H, J=10 Hz, CH2O); 3.95 (d, 2H, OCH2CH=); 5.05 and 5.18 (2d, 2H, CH2=CH); 5.78 (m, 1H, CH2=CH); 6.85 (d, 2 HAr); 7.37 (d, 2 HAr).
LC/MS Gradient 1: Rt: 2.26 min; 318+ (MH+CH3CN)+

CE: 2',3'-dihydro-5'-methoxyspiro(imidazolidin-4,1'(1H)inden)-2,5-dione

Reaction time: 60 hours; Yd=10%.
1H-NMR (DMSO D6): δ 2.15 and 2.55 (2m, 2H, CH2); 2.97 (m, 2H, CH2Ph); 3.75 (s, 3H, OMe); 6.8 (dd, 1 HAr); 6.9 (sl; 1 HAr); 7.05 (d, 1 HAr); 8.3 (s, 1H, NH).

CF: 7-(3,5-difluoro-4-methoxyphenyl)-4-ethylimidazolidine-2,5-dione

Reaction time: 5 days; Yd=86%.
1H-NMR (DMSO D6): δ 0.8 (t, 3H, CH3-CH2); 1.8-1.9 and 1.99-2.1 (2m, 2H, CH2); 3.9 (s, 3H, OMe); 7.2-7.3 (m, 2 HAr); 8.65 (s, 1H, NH).
LC/MS Gradient 2: Rt: 1.09 min; no ionisation CG: 4-ethyl-4-(4-methoxyphenyl)imidazolidine-2,5-dione Reaction time: 98 hours; Yd=96%.
1H-NMR (DMSO D6): δ 0.8 (t, 3H, CH3 Et); 1.84 and 2.04 (2m, 2H, CH2 Et); 3.74 (s, 3H, OMe); 6.95 (d, 2 HAr); 7.40 (d, 2 HAr); 8.59 (s, 1H, CONH); 10.79 (s, 1H, CONHCO).
LC/MS Gradient 2: Rt: 1.29 min; 233– (M–H)–

CH: 4-(3-Chloro-4-methoxyphenyl)-4-methylimidazolidine-2,5-dione

Reaction time: 6 days; Yd=95%.
1H-NMR (MeOD): δ 1.62 (s, 3H, Me); 3.79 (s, 3H, OMe); 6.99 (d, 1 HAr); 7.32 (d, 1 HAr); 7.40 (s, 1H, NH).
LC/MS Gradient 2: Rt: 1.44 min; 253– (M–H)–

CI: 4-butyl-4-(4-methoxyphenyl)imidazolidine-2,5-dione

Reaction time: 4 days; Yd=39%.
LC/MS Gradient 2: Rt: 1.28 min; 304+ (MH+CH3CN)+

CJ: 4-(4-methoxyphenyl)-4-propylimidazolidine-2,5-dione

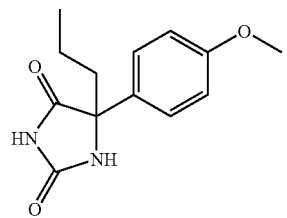

Reaction time: 18 hours; Yd=91%.
1H-NMR (DMSO D6): δ 0.88 (t, 3H, Me); 1.2 (m, 2H, CH2); 1.8 and 1.95 (2m, 2H, CH2); 3.73 (s, 3H, OMe); 6.93 (d, 2 HAr); 7.4 (d, 2 HAr); 8.58 (s, 1H, NH); 10.7 (sl, 1H, NH).

All publications, including but not limited to patents and patent applications, cited in this specification are herein incorporated by reference as if each individual publication were specifically and individually indicated to be incorporated by reference herein as though fully set forth.

From the foregoing description, various modifications and changes in the compositions and methods of this invention will occur to those skilled in the art. All such modifications coming within the scope of the appended claims are intended to be included therein.

It should be understood that factors such as the differential cell penetration capacity of the various compounds can contribute to discrepancies between the activity of the compounds in the in vitro biochemical and cellular assays.

At least some of the chemical names of compounds of the invention as given and set forth in this application, may have been generated on an automated basis by use of a commercially available chemical naming software program, and have not been independently verified. Representative programs performing this function include the Lexichem naming tool sold by Open Eye Software, Inc. and the Autonom Software tool sold by MDL, Inc. In the instance where the indicated chemical name and the depicted structure differ, the depicted structure will control.

The invention claimed is:
1. A compound of formula (I):

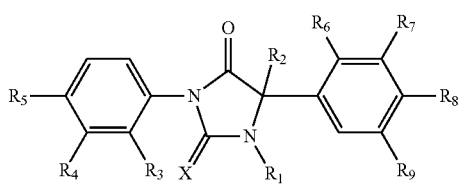

wherein
X is O or S,
R₁ represents acyl, aldehyde, cycloalkyl group or is a straight or branched alkyl, alkenyl, alkynyl, hydroxyalkyl, hydroxyalkenyl, hydroxyalkynyl, haloalkyl, haloalkenyl, or haloalkynyl group; alkylsulphonyl; arylsulphonyl optionally substituted by one or more substituents, which may be the same or different, selected from the group b as defined below; alkylenedioxy groups; alkoxycarbonyl; aralkoxycarbonyl; aryloxycarbonyl; alkoxycarbonylalkyl; aralkoxycarbonylalkyl; aryloxycarbonylalkyl; trifluoromethyl; a straight or branched alkyl group substituted with an aryl group, a cycloalkyl or heterocyclyl group, alkoxy, alkoxy-substituted alkoxy, alkylthio and the oxidised sulphoxide and sulphone forms thereof, alkylenedioxy groups; cyano, amino, alkylamino, aralkylamino, arylamino, dialkylamino, diaralkylamino, diarylamino, acylamino, trifluoromethylcarbonylamino, fluoroalkylcarbonylamino, diacylamino, aminocarbonyl, alkylaminocarbonyl, dialkylaminocarbonyl, or oxo group; and wherein any cycloalkyl or heterocyclyl groups or any aryl component is mono- or bi-cyclic and is optionally substituted by one or more substituents, which may be the same or different, selected from the group b,
wherein the group b consists of: halogen atoms; hydroxyl; aldehyde groups; straight and branched alkyl, alkenyl, alkynyl, hydroxyalkyl, hydroxyalkenyl, hydroxyalkynyl, haloalkyl, haloalkenyl, and haloalkynyl groups; straight and branched alkoxyl groups; straight and branched thioalkyl and alkylthio groups; alkoxycarbonyl; hydroxycarbonylalkyl; alkoxycarbonylalkyl; perfluoroalkyl; perfluoroalkoxy; —CN; acyl; amino, alkylamino, dialkylamino, acylamino groups; alkyl groups substituted with an amino, alkylamino, dialkylamino, acylamino, or diacylamino group; CONH₂; alkylamido groups; alkylthio and the oxidised sulphoxide and sulphone forms thereof; alkylenedioxy groups; and sulphonamide or alkylsulphonamide groups;
R₂ represents a hydrogen atom, a straight or branched alkyl group, hydroxyalkyl, haloalkyl, alkenyl, or alkynyl group; alkoxy- or alkenyloxy-substituted alkyl; alkylcarbonyl; alkoxycarbonylalkyl; or trifluoromethyl group;
R₃ and R₄, which may be the same or different, each represents a hydrogen atom, a halogen atom, a hydroxyl group, trifluoromethyl, a straight or branched alkyl, alkenyl, alkynyl, hydroxyalkyl, haloalkyl, haloalkenyl, or haloalkynyl group; a straight or branched alkoxyl group; or a straight or branched alkylthio group, or R₃ and R₄, together, represent an, optionally aromatic or heterocyclic, ring having the carbons to which they are attached forming a part of said ring, and being optionally further substituted by substituents b, R₅ represents a hydrogen atom, a halogen atom, trifluoromethyl, —CN, or an —NO₂ group; provided that not all of R₃, R₄, and R₅ represents H,
R₆ and R₉ are the same or different, and each represents hydrogen, halogen, hydroxyl; a straight or branched alkyl group, hydroxyalkyl, haloalkyl, alkenyl, or alkynyl group; a straight or branched alkoxyl group; or a straight or branched thioalkyl group;
R₇ and R₈ are the same or different, and each represents hydrogen, halogen, hydroxyl, sulphydryl; a straight and branched alkoxyl group optionally substituted by one or more hydroxyl groups and/or halogen atoms; a straight or branched alkylthio group optionally substituted by one or more hydroxyl groups and/or halogen atoms; and wherein at least one of R₇ and R₈ is a hydroxyl; a sulphydryl; a straight or branched alkoxyl group; a straight or branched alkylthio group;
or R₇, R₈ and R₉ are as defined, and R₆ is $C_{1-3}$-alkyl or, together with either R₁ or R₂, represents a methylene, ethylene, ethenylene, propylene, or propenylene linking group, optionally substituted by one or more methyl, trifluoromethyl, hydroxyl or halogen atoms, and wherein any alkyl components contain from 1 to 6 carbon atoms, unless otherwise specified, and any alkenyl or alkynyl components contain from 2 to 6 carbon atoms, and are optionally substituted by at least one halogen atom or hydroxy group, and wherein any aryl component is optionally a heteroaryl group,
provided that, when X is O, R₁ is alkyl, and R₂ is hydrogen, then at least one of R₇ and R₈ is a hydroxyl, or a sulphydryl,
and pharmaceutically acceptable salts and esters thereof.

2. A compound according to claim 1, wherein
R₁ represents acyl, aldehyde, cycloalkyl group or is a straight or branched alkyl, alkenyl, alkynyl, hydroxyalkyl, hydroxyalkenyl, hydroxyalkynyl, haloalkyl, haloalkenyl, or haloalkynyl group; alkoxycarbonyl; aralkoxycarbonyl; aryloxycarbonyl; alkoxycarbonylalkyl; aralkoxycarbonylalkyl; aryloxycarbonylalkyl; trifluoromethyl; a straight or branched alkyl group substituted with an aryl group, a cycloalkyl or heterocyclyl group, alkoxy, alkoxy-substituted alkoxy, alkylthio, cyano, amino, alkylamino, aralkylamino, arylamino, dialkylamino, diaralkylamino, diarylamino, acylamino, trifluoromethylcarbonylamino, fluoroalkylcarbonylamino, diacylamino, aminocarbonyl, alkylaminocarbonyl, dialkylaminocarbonyl, or oxo group; and wherein any cycloalkyl or heterocyclyl groups or any aryl component is mono- or bi-cyclic and is optionally substituted by one or more substituents, which may be the same or different, selected from the group b as defined, and
R₃ and R₄, which may be the same or different, each represents a hydrogen atom, a halogen atom, trifluoromethyl, a straight or branched alkyl, alkenyl, alkynyl, hydroxyalkyl, haloalkyl, haloalkenyl, or haloalkynyl group; a straight or branched alkoxyl group; or a straight or branched alkylthio group, or R₃ and R₄, together, represent an, optionally aromatic or heterocyclic, ring having the carbons to which they are attached forming a part of said ring, and being optionally further substituted by substituents b.

3. A compound according to claim 2, wherein X is O.
4. A compound according to claim 2, wherein R₂ is a hydrogen atom, a straight or branched alkyl group, hydroxyalkyl, haloalkyl, or trifluoromethyl group.

5. A compound according to claim 2, wherein one of $R_7$ and $R_8$ is a hydroxyl.

6. A compound according to claim 5, wherein $R_8$ is —OH.

7. A compound according to claim 2, wherein $R_4$ is halogen, trifluoromethyl, or a straight or branched alkyl or alkoxyl group.

8. A compound according to claim 2, wherein $R_5$ is halogen, —NO$_2$, or —CN.

9. A compound according to claim 2, wherein $R_4$ is trifluoromethyl and $R_5$ is —CN.

10. A compound selected from:
1-(3,4-dichlorophenyl)-4-(4-hydroxyphenyl)-3-methylimidazolidine-2,5-dione,
1-(3,4-dichlorophenyl)-4-(4-hydroxyphenyl)-3-(2-propenyl)imidazolidine-2,5-dione,
4-[2,5-dioxo-4-(4-hydroxyphenyl)-3-(2-propynyl)imidazolidin-1-yl]-2-trifluoromethylbenzonitrile,
4-[3,4-dimethyl-2,5-dioxo-4-(4-hydroxyphenyl)imidazolidin-1-yl]-2-trifluoromethyl-benzonitrile,
4-[2,5-dioxo-4-(4-hydroxyphenyl)-4-methyl-3-(2-propynyl)-imidazolidin-1-yl]-2-trifluoromethylbenzonitrile,
4-[4-(4-hydroxyphenyl)-4-methyl-5-oxo-3-(2-propenyl)-2-thioxoimidazolidin-1-yl]-2-trifluoromethylbenzonitrile,
2-chloro-4-[3,4-dimethyl-2,5-dioxo-4-(4-hydroxyphenyl)imidazolidin-1-yl]-3-methyl-benzonitrile,
4-[3,4-dimethyl-2,5-dioxo-4-(4-hydroxyphenyl)imidazolidin-1-yl]-2-methoxy-benzonitrile,
(R)-4-[3,4-dimethyl-2,5-dioxo-4-(4-hydroxyphenyl)imidazolidin-1-yl]-2-trifluoromethylbenzonitrile,
1-(3,4-dichlorophenyl)-4-hydroxymethyl-4-(4-hydroxyphenyl)-3-methyl-imidazolidine-2,5-dione,
4-[4-hydroxymethyl-4-(4-hydroxyphenyl)-3-methyl-2,5-dioxoimidazolidin-1-yl]-2-trifluoromethylbenzonitrile,
4-[4-fluoromethyl-4-(4-hydroxyphenyl)-3-methyl-2,5-dioxoimidazolidin-1-yl]-2-trifluoromethylbenzonitrile,
4-[3-(2-butynyl)-4-(4-hydroxyphenyl)-4-methyl-2,5-dioxo-imidazolidin-1-yl]-2-trifluoromethyl-benzonitrile,
4-[4-(4-hydroxyphenyl)-3-methoxymethyl-4-methyl-2,5-dioxoimidazolidin-1-yl]-2-trifluoromethylbenzonitrile,
(R)-4-[3,4-dimethyl-2,5-dioxo-4-(4-hydroxyphenyl)imidazolidin-1-yl]-2-methoxybenzonitrile,
(R)-4-[4-fluoromethyl-4-(4-hydroxyphenyl)-3-methyl-2,5-dioxoimidazolidin-1-yl]-2-trifluoromethylbenzonitrile,
4-[2,5-dioxo-4-(4-hydroxyphenyl)-3-methoxymethyl-4-methylimidazolidin-1-yl]-2-trifluoromethylbenzonitrile, and
(R)-4-[2,5-dioxo-4-(4-hydroxyphenyl)-3-methoxymethyl-4-methylimidazolidin-1-yl]-2-trifluoromethyl-benzonitrile.

11. A pharmaceutical composition comprising a pharmaceutically acceptable carrier and a pharmaceutically effective amount of a compound according to claim 1.

12. The pharmaceutical composition of claim 11, wherein the carrier is selected from a parenteral carrier, an oral carrier and a topical carrier.

13. A method of treatment of a condition selected from cachexia, osteoporosis, sarcopenia, a decline in libido and/or sexual dysfunction, and prostate cancer and/or hyperplasia, comprising administering to a subject a therapeutically effective amount of a compound of formula (I):

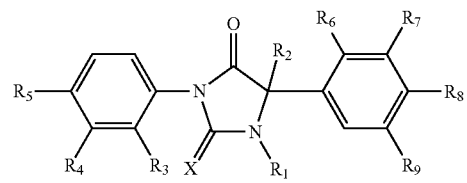

wherein
X is O or S,
$R_1$ represents acyl, aldehyde, cycloalkyl group or is a straight or branched alkyl, alkenyl, alkynyl, hydroxyalkyl, hydroxyalkenyl, hydroxyalkynyl, haloalkyl, haloalkenyl, or haloalkynyl group; alkylsulphonyl; arylsulphonyl optionally substituted by one or more substituents, which may be the same or different, selected from the group b as defined below; alkylenedioxy groups; alkoxycarbonyl; aralkoxycarbonyl; aryloxycarbonyl; alkoxycarbonylalkyl; aralkoxycarbonylalkyl; aryloxycarbonylalkyl; trifluoromethyl; a straight or branched alkyl group substituted with an aryl group, a cycloalkyl or heterocyclyl group, alkoxy, alkoxy-substituted alkoxy, alkylthio and the oxidised sulphoxide and sulphone forms thereof, alkylenedioxy groups; cyano, amino, alkylamino, aralkylamino, arylamino, dialkylamino, diaralkylamino, diarylamino, acylamino, trifluoromethylcarbonylamino, fluoroalkylcarbonylamino, diacylamino, aminocarbonyl, alkylaminocarbonyl, dialkylaminocarbonyl, or oxo group; and wherein any cycloalkyl or heterocyclyl groups or any aryl component is mono- or bi-cyclic and is optionally substituted by one or more substituents, which may be the same or different, selected from the group b,
wherein the group b consists of: halogen atoms; hydroxyl; aldehyde groups; straight and branched alkyl, alkenyl, alkynyl, hydroxyalkyl, hydroxyalkenyl, hydroxyalkynyl, haloalkyl, haloalkenyl, and haloalkynyl groups; straight and branched alkoxyl groups; straight and branched thioalkyl and alkylthio groups; alkoxycarbonyl; hydroxycarbonylalkyl; alkoxycarbonylalkyl; perfluoroalkyl; perfluoroalkoxy; —CN; acyl; amino, alkylamino, dialkylamino, acylamino groups; alkyl groups substituted with an amino, alkylamino, dialkylamino, acylamino, or diacylamino group; CONH$_2$; alkylamido groups; alkylthio and the oxidised sulphoxide and sulphone forms thereof; alkylenedioxy groups; and sulphonamide or alkylsulphonamide groups;
$R_2$ represents a hydrogen atom, a straight or branched alkyl group, hydroxyalkyl, haloalkyl, alkenyl, or alkynyl group; alkoxy- or alkenyloxy-substituted alkyl; alkylcarbonyl; alkoxycarbonylalkyl; or trifluoromethyl group;
$R_3$ and $R_4$, which may be the same or different, each represents a hydrogen atom, a halogen atom, a hydroxyl group, trifluoromethyl, a straight or branched alkyl, alkenyl, alkynyl, hydroxyalkyl, haloalkyl, haloalkenyl, or haloalkynyl group; a straight or branched alkoxyl group; or a straight or branched alkylthio group, or $R_3$ and $R_4$, together, represent an, optionally aromatic or heterocyclic, ring having the carbons to which they are attached forming a part of said ring, and being optionally further substituted by substituents b,
$R_5$ represents a hydrogen atom, a halogen atom, trifluoromethyl, —CN, or an —NO$_2$ group; provided that not all of $R_3$, $R_4$, and $R_5$ represents H, R$_6$ and R$_9$ are the same or different, and each represents hydrogen, halogen, hydroxyl; a straight or branched alkyl group, hydroxyalkyl, haloalkyl, alkenyl, or alkynyl group; a straight or branched alkoxyl group; or a straight or branched thioalkyl group;

R$_7$ and R$_8$ are the same or different, and each represents hydrogen, halogen, hydroxyl, sulphydryl; a straight and branched alkoxyl group optionally substituted by one or more hydroxyl groups and/or halogen atoms; a straight or branched alkylthio group optionally substituted by one or more hydroxyl groups and/or halogen atoms; and wherein at least one of R$_7$ and R$_8$ is a hydroxyl; a straight or branched alkoxyl group; a straight or branched alkylthio group;

or R$_7$, R$_8$ and R$_9$ are as defined, and R$_6$ is C$_{1-3}$-alkyl or, together with either R$_1$ or R$_2$, represents a methylene, ethylene, ethenylene, propylene, or propenylene linking group, optionally substituted by one or more methyl, trifluoromethyl, hydroxyl or halogen atoms, and wherein any alkyl components contain from 1 to 6 carbon atoms, unless otherwise specified, and any alkenyl or alkynyl components contain from 2 to 6 carbon atoms, and are optionally substituted by at least one halogen atom or hydroxy group, and wherein any aryl component is optionally a heteroaryl group, and pharmaceutically acceptable salts and esters thereof.

14. The method according to claim 13, wherein the condition is selected from cachexia, osteoporosis, sarcopenia, a decline in libido and/or sexual dysfunction.

15. The method according to claim 13, wherein the condition is selected from prostate cancer and/or hyperplasia.

16. A method according to claim 13, for the therapy of muscle loss induced by chronic treatment with glucocorticoids.

17. A method of treatment of cachexia, osteoporosis, sarcopenia, a decline in libido and/or sexual dysfunction, comprising administering to a subject, a therapeutically effective amount of a compound as recited in claim 13.

18. A method of treatment of prostate cancer and/or hyperplasia, comprising administering to a subject, a therapeutically effective amount of a compound as recited in claim 13.

19. A method of treatment of a disease associated with cachexia, osteoporosis, sarcopenia, a decline in libido and/or sexual dysfunction, and prostate cancer and/or hyperplasia, comprising administering to a subject a therapeutically effective amount of a pharmaceutical composition according to claim 11.

* * * * *